US009464137B2

(12) United States Patent
Satomaa et al.

(10) Patent No.: US 9,464,137 B2
(45) Date of Patent: Oct. 11, 2016

(54) GLYCOPROTEIN

(71) Applicant: Glykos Finland Oy, Helsinki (FI)

(72) Inventors: Tero Satomaa, Helsinki (FI); Juhani Saarinen, Helsinki (FI); Jari Natunen, Vantaa (FI); Anja Vilkman, Klaukkala (FI); Heidi Virtanen, Helsinki (FI); Jukka Hiltunen, Helsinki (FI)

(73) Assignee: Glykos Finland Oy, Helsinki (FI)

( * ) Notice: Subject to any disclaimer, the term of this patent is extended or adjusted under 35 U.S.C. 154(b) by 0 days.

(21) Appl. No.: 14/365,022

(22) PCT Filed: Dec. 13, 2012

(86) PCT No.: PCT/FI2012/051239
§ 371 (c)(1),
(2) Date: Jun. 12, 2014

(87) PCT Pub. No.: WO2013/087993
PCT Pub. Date: Jun. 20, 2013

(65) Prior Publication Data
US 2015/0191544 A1 Jul. 9, 2015

Related U.S. Application Data

(60) Provisional application No. 61/569,900, filed on Dec. 13, 2011, provisional application No. 61/569,906, filed on Dec. 13, 2011.

(30) Foreign Application Priority Data

Dec. 13, 2011 (FI) ..................... 20116264

(51) Int. Cl.
*C07K 16/28* (2006.01)
*A61K 47/48* (2006.01)
*C07K 16/24* (2006.01)
*C07K 16/00* (2006.01)
*A61K 39/00* (2006.01)

(52) U.S. Cl.
CPC ..... *C07K 16/2863* (2013.01); *A61K 47/48092* (2013.01); *C07K 16/00* (2013.01); *C07K 16/244* (2013.01); *A61K 2039/505* (2013.01); *C07K 2317/41* (2013.01); *C07K 2317/52* (2013.01); *C07K 2317/72* (2013.01); *C07K 2317/732* (2013.01)

(58) Field of Classification Search
None
See application file for complete search history.

(56) References Cited

U.S. PATENT DOCUMENTS

| 4,946,778 | A  | 8/1990 | Ladner et al. |
| 6,946,292 | B2 | 9/2005 | Kanda et al. |
| 7,393,683 | B2 | 7/2008 | Kanda et al. |

| 2003/0157108 | A1 | 8/2003 | Presta |
| 2009/0136525 | A1 | 5/2009 | Gerngross et al. |
| 2011/0047657 | A1 | 2/2011 | Von Schaewen et al. |
| 2011/0092374 | A1 | 4/2011 | Callewaert et al. |

FOREIGN PATENT DOCUMENTS

| WO | WO 2007/084672 A2 | 7/2007 |
| WO | WO 2008/121876 A2 | 10/2008 |

OTHER PUBLICATIONS

International Search Report for corresponding International Patent Application No. PCT/FI2012/051239 mailed May 13, 2013.
Finnish Search Report for corresponding Finnish Patent Application No. 20116264 mailed Oct. 2, 2012.
Abès, R. et al., "Impact of Glycosylation on Effector Functions of Therapeutic IgG", *Pharmaceuticals*, 3: 146-157 (2010).
IUPAC-IUBMB JCBN, "Nomenclature of glycolipids", *Carbohydrate Research*, 312: 167-175 (1998).
Cole, S. et al., "The EBV-Hybridoma Technique and Its Application to Human Lung Cancer", *Monoclonal Antibodies and Cancer Therapy*, 77-96 (1985).
Mizushima, T. et al., "Structural basis for improved efficacy of therapeutic antibodies on defucosylation of their Fc glycans", *Genes to Cells*, 6(11): 1161-1173 (2006).
IUPAC-IUB JCBN Chester, M., "Nomenclature of glycolipids", *Eur. J. Biochem.*, 257: 293-298 (1998).
Ohyama, C. et al., "Molecular Cloning and Expression of GDP-$_D$-mannose-4,6-dehydratase, a Key Enzyme for Fucose Metabolism Defective in Lec13 Cells", *Jour Biol. Chem.*, 273(23): 14582-14587 (1998).
Takeda, S. et al., "Construction of chimaeric processed immunoglobulin genes containing mouse variable and human constant region sequences", *Nature*, 314: 452-454 (1985).
Jenkins, N. et al., "Getting the glycosylation right: Implications for the biotechnology industry", *Nature Biotechnol.*, 14: 975-981 (1996).
Kohler et al., "Continuous cultures of fused cells secreting antibody of predefined specificity", *Nature*, 256: 495-497 (1975).
Kozbor, D. et al., "The production of monoclonal antibodies from human lymphocytes", *Immunology Today*, 4: 72-79 (1983).
Neuberger, M. et al., "Recombinant antibodies possessing novel effector functions", *Nature*, 312: 604-608 (1984).
Satomaa, T. et al., "Analysis of the Human Cancer Glycome Identifies a Novel Group of Tumor-Associated N-Acetylglucosamine Glycan Antigens", *Cancer Research*, 69: 5811-5819 (2009).

(Continued)

*Primary Examiner* — Brian J Gangle
*Assistant Examiner* — Andrea McCollum
(74) *Attorney, Agent, or Firm* — Merchant & Gould P.C.

(57) ABSTRACT

The invention relates to a composition comprising a glycoprotein comprising the Fc domain of an antibody, or a fragment thereof, comprising an Asn (asparagine) residue and an oligosaccharide structure attached thereto, wherein said oligosaccharide structure has a structure according to formula I; and wherein at least 20% of the oligosaccharide structures attached to glycoprotein in the composition consist of oligosaccharide structures according to formula (I).

10 Claims, 3 Drawing Sheets

(56) References Cited

OTHER PUBLICATIONS

Butler, M. et al., "Detailed glycan analysis of serum glycoproteins of patients with congenital disorders of glycosylation indicates the specific defective glycan processing step and provides an insight into pathogenesis", *Glycobiology*, 13(9): 601-622 (2003).
Chen, X. et al., "The effect of Fc glycan forms on human IgG2 antibody clearance in humans", *Glycobiology*, 19(3): 240-249 (2009).
Morrison, S. et al., "Chimeric human antibody molecules: Mouse antigen-binding domains with human constant region domains", *Proc. Natl. Acad. Sci. USA*, 81: 6851-6855 (1984).
Raju, T., "Terminal sugars of Fc glycans influence antibody effector functions of IgGs", *Current Opinion in Immunology*, 20(4): 471-478 (2008).
Bowie, J. et al., "Deciphering the Message in Protein Sequences: Tolerance to Amino Acid Substitutions", *Science*, 247: 1306-1310 (1990).
Cote, R. et al., "Generation of human monoclonal antibodies reactive with cellular antigens", *Proc. Natl. Acad. Sci. USA*, 80: 2026-2030 (1983).
IUPAC-IUBMB JCBN, "Nomenclature of Carbohydrates", *Carbohydrate Res.*, 297: 1-91 (1997).
Forthal, D. et al., "Fc-Glycosylation Influences Fcγ Receptor Binding and Cell-Mediated Anti-HIV Activity of Monoclonal Antibody 2G12", *J. Immunology*, 185(11): 6876-6882 (2010).
Kanda, Y. et al., "Comparison of biological activity among nonfucosylated therapeutic IgG1 antibodies with three different N-linked Fc oligosaccharides: the high-mannose, hybrid, and complex types", *Glycobiology*, 17(1): 104-118 (2006).
Cumming, D., "Glycosylation of recombinant protein therapeutics: control and functional implications", *Glycobiology*, 1(2): 115-130 (1991).
Roda, J. et al., "Interleukin-21 Enhances NK Cell Activation in Response to Antibody-Coated Targets", *J. Immunol*, 177: 120-129 (2006).
Shinkawa, T. et al., "The Absence of Fucose but Not the Presence of Galactose or Bisecting N-Acetylglucosamine of Human IgG1 Complex-type Antibody-dependent Cellular Cytotoxicity", *J. Biol. Chem.*, 278(5): 3466-3473 (2003).
Tojo, S. et al., "A Chromatographic Approach for Elevating the Antibody-Dependent Cellular Cytotoxicity of Antibody Composites", *Biol. Pharm. Bull.*, 32(9): 1604-1608 (2009).
Ferrara, C. et al., "Modulation of Therapeutic Antibody Effector Functions of Glycosylation Engineering: Influence of Golgi Enzyme Localization Domain and Co-Expression of Heterologous β1, 4-N-acetylglucosaminyltransferase III and Golgi α-mannosidase II", *Biotechnology & Bioengineering*, 93(5): 851-861 (2006).
Niwa, R. et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma", *Cancer Research*, 64: 2127-2133 (2004).
Niwa, R. et al., "IgG subclass-independent improvement of antibody-dependent cellular cytotoxicity by fucose removal from $Asn^{297}$-linked oligosaccharides", *J. Immun. Methods*, 306: 151-160 (2005).
Shields, R. et al., "Lack of Fucose on Human IgG1 N-Linked Oligosaccharide Improves Binding to Human FcγRIII and Antibody-dependent Cellular Toxicity", *J. Biol. Chem.*, 277(30): 26733-26740 (2002).
Iida, S. et al., "Nonfucosylated Therapeutic IgG1 Antibody Can Evade the Inhibitory Effect of Serum Immunoglobulin G on Antibody-Dependent Cellular Cytotoxicity through its High Binding to FcγRIIIa", *Clin. Canc. Res.*, 12(9): 2879-2887 (2006).
Kanda, Y. et al., "Comparison of Cell Lines for Stable Production of Fucose-Negative Antibodies with Enhanced ADCC", *Biotechnology & Bioengineering, Wiley & Sons*, 94(4): 680-688 (2006).
Satoh, M. et al., "Non-fucosylated therapeutic antibodies as next-generation therapeutic antibodies", *Exp. Opin. Biol. Therapy*, 6(11): 1161-1173 (2006).
Matsumiya, S. et al., "Structural Comparison of Fucosylated and Nonfucosylated Fc Fragments of Human Immunoglobulin G1", *J. Mole. Biol.*, 368: 767-779 (2007).
Ip, C. et al., "Structural Characterization of the N-Glycans of a Humanized Anti-CD18 Murine Immunoglobulin G", *Arch. Biochem. & Biophys.*, 308(2): 387-399 (1994).
Ripka, J. et al., "Lectin-Resistant CHO Cells: Selection of Four New Pea Lectin-Resistant Phenotypes", *Somatic Cell and Molecular Genetics*, 12(1): 51-62 (1986).
Ripka, J. et al., "Two Chinese Hamster Ovary Glycosylation Mutants Affected in the Conversion of GDP-Mannose to GDP-Fucose", *Arch. Biochem. & Biophys.*, 249(2): 533-545 (1986).

SEQUENCE LISTING

```
<160> NUMBER OF SEQ ID NOS: 25

<210> SEQ ID NO 1
<211> LENGTH: 1144
<212> TYPE: PRT
<213> ORGANISM: Homo sapiens

<400> SEQUENCE: 1

Met Lys Leu Ser Arg Gln Phe Thr Val Phe Gly Ser Ala Ile Phe Cys
1               5                   10                  15

Val Val Ile Phe Ser Leu Tyr Leu Met Leu Asp Arg Gly His Leu Asp
            20                  25                  30

Tyr Pro Arg Asn Pro Arg Arg Glu Gly Ser Phe Pro Gln Gly Gln Leu
        35                  40                  45

Ser Met Leu Gln Glu Lys Ile Asp His Leu Glu Arg Leu Leu Ala Glu
    50                  55                  60
```

-continued

```
Asn Asn Glu Ile Ile Ser Asn Ile Arg Asp Ser Val Ile Asn Leu Ser
 65                  70                  75                  80

Glu Ser Val Glu Asp Gly Pro Lys Ser Gln Ser Asn Phe Ser Gln
             85                  90                  95

Gly Ala Gly Ser His Leu Leu Pro Ser Gln Leu Ser Leu Ser Val Asp
            100                 105                 110

Thr Ala Asp Cys Leu Phe Ala Ser Gln Ser Gly Ser His Asn Ser Asp
            115                 120                 125

Val Gln Met Leu Asp Val Tyr Ser Leu Ile Ser Phe Asp Asn Pro Asp
        130                 135                 140

Gly Gly Val Trp Lys Gln Gly Phe Asp Ile Thr Tyr Glu Ser Asn Glu
145                 150                 155                 160

Trp Asp Thr Glu Pro Leu Gln Val Phe Val Pro His Ser His Asn
                165                 170                 175

Asp Pro Gly Trp Leu Lys Thr Phe Asn Asp Tyr Phe Arg Asp Lys Thr
                180                 185                 190

Gln Tyr Ile Phe Asn Asn Met Val Leu Lys Leu Lys Glu Asp Ser Arg
            195                 200                 205

Arg Lys Phe Ile Trp Ser Glu Ile Ser Tyr Leu Ser Lys Trp Trp Asp
        210                 215                 220

Ile Ile Asp Ile Gln Lys Lys Asp Ala Val Lys Ser Leu Ile Glu Asn
225                 230                 235                 240

Gly Gln Leu Glu Ile Val Thr Gly Gly Trp Val Met Pro Asp Glu Ala
                245                 250                 255

Thr Pro His Tyr Phe Ala Leu Ile Asp Gln Leu Ile Glu Gly His Gln
            260                 265                 270

Trp Leu Glu Asn Asn Ile Gly Val Lys Pro Arg Ser Gly Trp Ala Ile
        275                 280                 285

Asp Pro Phe Gly His Ser Pro Thr Met Ala Tyr Leu Leu Asn Arg Ala
        290                 295                 300

Gly Leu Ser His Met Leu Ile Gln Arg Val His Tyr Ala Val Lys Lys
305                 310                 315                 320

His Phe Ala Leu His Lys Thr Leu Glu Phe Phe Trp Arg Gln Asn Trp
                325                 330                 335

Asp Leu Gly Ser Val Thr Asp Ile Leu Cys His Met Met Pro Phe Tyr
            340                 345                 350

Ser Tyr Asp Ile Pro His Thr Cys Gly Pro Asp Pro Lys Ile Cys Cys
        355                 360                 365

Gln Phe Asp Phe Lys Arg Leu Pro Gly Gly Arg Phe Gly Cys Pro Trp
        370                 375                 380

Gly Val Pro Pro Glu Thr Ile His Pro Gly Asn Val Gln Ser Arg Ala
385                 390                 395                 400

Arg Met Leu Leu Asp Gln Tyr Arg Lys Lys Ser Lys Leu Phe Arg Thr
                405                 410                 415

Lys Val Leu Leu Ala Pro Leu Gly Asp Asp Phe Arg Tyr Cys Glu Tyr
            420                 425                 430

Thr Glu Trp Asp Leu Gln Phe Lys Asn Tyr Gln Gln Leu Phe Asp Tyr
        435                 440                 445

Met Asn Ser Gln Ser Lys Phe Lys Val Lys Ile Gln Phe Gly Thr Leu
        450                 455                 460

Ser Asp Phe Phe Asp Ala Leu Asp Lys Ala Asp Glu Thr Gln Arg Asp
465                 470                 475                 480

Lys Gly Gln Ser Met Phe Pro Val Leu Ser Gly Asp Phe Phe Thr Tyr
```

```
                    485                 490                 495
Ala Asp Arg Asp Asp His Tyr Trp Ser Gly Tyr Phe Thr Ser Arg Pro
                        500                 505                 510

Phe Tyr Lys Arg Met Asp Arg Ile Met Glu Ser His Leu Arg Ala Ala
                    515                 520                 525

Glu Ile Leu Tyr Tyr Phe Ala Leu Arg Gln Ala His Lys Tyr Lys Ile
                530                 535                 540

Asn Lys Phe Leu Ser Ser Ser Leu Tyr Thr Ala Leu Thr Glu Ala Arg
545                 550                 555                 560

Arg Asn Leu Gly Leu Phe Gln His His Asp Ala Ile Thr Gly Thr Ala
                        565                 570                 575

Lys Asp Trp Val Val Asp Tyr Gly Thr Arg Leu Phe His Ser Leu
                    580                 585                 590

Met Val Leu Glu Lys Ile Ile Gly Asn Ser Ala Phe Leu Leu Ile Leu
                595                 600                 605

Lys Asp Lys Leu Thr Tyr Asp Ser Tyr Ser Pro Asp Thr Phe Leu Glu
                610                 615                 620

Met Asp Leu Lys Gln Lys Ser Gln Asp Ser Leu Pro Gln Lys Asn Ile
625                 630                 635                 640

Ile Arg Leu Ser Ala Glu Pro Arg Tyr Leu Val Tyr Asn Pro Leu
                        645                 650                 655

Glu Gln Asp Arg Ile Ser Leu Val Ser Val Tyr Val Ser Ser Pro Thr
                    660                 665                 670

Val Gln Val Phe Ser Ala Ser Gly Lys Pro Val Glu Val Gln Val Ser
                675                 680                 685

Ala Val Trp Asp Thr Ala Asn Thr Ile Ser Glu Thr Ala Tyr Glu Ile
                690                 695                 700

Ser Phe Arg Ala His Ile Pro Pro Leu Gly Leu Lys Val Tyr Lys Ile
705                 710                 715                 720

Leu Glu Ser Ala Ser Ser Asn Ser His Leu Ala Asp Tyr Val Leu Tyr
                        725                 730                 735

Lys Asn Lys Val Glu Asp Ser Gly Ile Phe Thr Ile Lys Asn Met Ile
                    740                 745                 750

Asn Thr Glu Glu Gly Ile Thr Leu Glu Asn Ser Phe Val Leu Leu Arg
                755                 760                 765

Phe Asp Gln Thr Gly Leu Met Lys Gln Met Met Thr Lys Glu Asp Gly
                770                 775                 780

Lys His His Glu Val Asn Val Gln Phe Ser Trp Tyr Gly Thr Thr Ile
785                 790                 795                 800

Lys Arg Asp Lys Ser Gly Ala Tyr Leu Phe Leu Pro Asp Gly Asn Ala
                        805                 810                 815

Lys Pro Tyr Val Tyr Thr Thr Pro Pro Phe Val Arg Val Thr His Gly
                    820                 825                 830

Arg Ile Tyr Ser Glu Val Thr Cys Phe Phe Asp His Val Thr His Arg
                835                 840                 845

Val Arg Leu Tyr His Ile Gln Gly Ile Glu Gly Gln Ser Val Glu Val
                850                 855                 860

Ser Asn Ile Val Asp Ile Arg Lys Val Tyr Asn Arg Glu Ile Ala Met
865                 870                 875                 880

Lys Ile Ser Ser Asp Ile Lys Ser Gln Asn Arg Phe Tyr Thr Asp Leu
                        885                 890                 895

Asn Gly Tyr Gln Ile Gln Pro Arg Met Thr Leu Ser Lys Leu Pro Leu
                    900                 905                 910
```

Gln Ala Asn Val Tyr Pro Met Thr Thr Met Ala Tyr Ile Gln Asp Ala
        915                 920                 925

Lys His Arg Leu Thr Leu Leu Ser Ala Gln Ser Leu Gly Val Ser Ser
        930                 935                 940

Leu Asn Ser Gly Gln Ile Glu Val Ile Met Asp Arg Arg Leu Met Gln
945                 950                 955                 960

Asp Asp Asn Arg Gly Leu Glu Gln Gly Ile Gln Asp Asn Lys Ile Thr
                965                 970                 975

Ala Asn Leu Phe Arg Ile Leu Leu Glu Lys Arg Ser Ala Val Asn Thr
            980                 985                 990

Glu Glu Glu Lys Lys Ser Val Ser Tyr Pro Ser Leu Leu Ser His Ile
            995                1000                1005

Thr Ser Ser Leu Met Asn His Pro Val Ile Pro Met Ala Asn Lys
    1010                1015                1020

Phe Ser Ser Pro Thr Leu Glu Leu Gln Gly Glu Phe Ser Pro Leu
    1025                1030                1035

Gln Ser Ser Leu Pro Cys Asp Ile His Leu Val Asn Leu Arg Thr
    1040                1045                1050

Ile Gln Ser Lys Val Gly Asn Gly His Ser Asn Glu Ala Ala Leu
    1055                1060                1065

Ile Leu His Arg Lys Gly Phe Asp Cys Arg Phe Ser Ser Lys Gly
    1070                1075                1080

Thr Gly Leu Phe Cys Ser Thr Thr Gln Gly Lys Ile Leu Val Gln
    1085                1090                1095

Lys Leu Leu Asn Lys Phe Ile Val Glu Ser Leu Thr Pro Ser Ser
    1100                1105                1110

Leu Ser Leu Met His Ser Pro Pro Gly Thr Gln Asn Ile Ser Glu
    1115                1120                1125

Ile Asn Leu Ser Pro Met Glu Ile Ser Thr Phe Arg Ile Gln Leu
    1130                1135                1140

Arg

<210> SEQ ID NO 2
<211> LENGTH: 1150
<212> TYPE: PRT
<213> ORGANISM: Homo sapiens

<400> SEQUENCE: 2

Met Lys Leu Lys Lys Gln Val Thr Val Cys Gly Ala Ala Ile Phe Cys
1               5                   10                  15

Val Ala Val Phe Ser Leu Tyr Leu Met Leu Asp Arg Val Gln His Asp
            20                  25                  30

Pro Thr Arg His Gln Asn Gly Gly Asn Phe Pro Arg Ser Gln Ile Ser
        35                  40                  45

Val Leu Gln Asn Arg Ile Glu Gln Leu Glu Gln Leu Leu Glu Glu Asn
    50                  55                  60

His Glu Ile Ile Ser His Ile Lys Asp Ser Val Leu Glu Leu Thr Ala
65                  70                  75                  80

Asn Ala Glu Gly Pro Pro Ala Met Leu Pro Tyr Tyr Thr Val Asn Gly
                85                  90                  95

Ser Trp Val Val Pro Pro Glu Pro Arg Pro Ser Phe Phe Ser Ile Ser
            100                 105                 110

Pro Gln Asp Cys Gln Phe Ala Leu Gly Gly Arg Gly Gln Lys Pro Glu
        115                 120                 125

-continued

```
Leu Gln Met Leu Thr Val Ser Glu Glu Leu Pro Phe Asp Asn Val Asp
    130                 135                 140

Gly Gly Val Trp Arg Gln Gly Phe Asp Ile Ser Tyr Asp Pro His Asp
145                 150                 155                 160

Trp Asp Ala Glu Asp Leu Gln Val Phe Val Pro His Ser His Asn
                    165                 170                 175

Asp Pro Gly Trp Ile Lys Thr Phe Asp Lys Tyr Tyr Thr Glu Gln Thr
                180                 185                 190

Gln His Ile Leu Asn Ser Met Val Ser Lys Leu Gln Glu Asp Pro Arg
            195                 200                 205

Arg Arg Phe Leu Trp Ala Glu Val Ser Phe Phe Ala Lys Trp Trp Asp
210                 215                 220

Asn Ile Asn Val Gln Lys Arg Ala Ala Val Arg Arg Leu Val Gly Asn
225                 230                 235                 240

Gly Gln Leu Glu Ile Ala Thr Gly Gly Trp Val Met Pro Asp Glu Ala
                245                 250                 255

Asn Ser His Tyr Phe Ala Leu Ile Asp Gln Leu Ile Glu Gly His Gln
            260                 265                 270

Trp Leu Glu Arg Asn Leu Gly Ala Thr Pro Arg Ser Gly Trp Ala Val
    275                 280                 285

Asp Pro Phe Gly Tyr Ser Ser Thr Met Pro Tyr Leu Leu Arg Arg Ala
290                 295                 300

Asn Leu Thr Ser Met Leu Ile Gln Arg Val His Tyr Ala Ile Lys Lys
305                 310                 315                 320

His Phe Ala Ala Thr His Ser Leu Glu Phe Met Trp Arg Gln Thr Trp
                325                 330                 335

Asp Ser Asp Ser Ser Thr Asp Ile Phe Cys His Met Met Pro Phe Tyr
            340                 345                 350

Ser Tyr Asp Val Pro His Thr Cys Gly Pro Asp Pro Lys Ile Cys Cys
    355                 360                 365

Gln Phe Asp Phe Lys Arg Leu Pro Gly Gly Arg Ile Asn Cys Pro Trp
370                 375                 380

Lys Val Pro Pro Arg Ala Ile Thr Glu Ala Asn Val Ala Glu Arg Ala
385                 390                 395                 400

Ala Leu Leu Leu Asp Gln Tyr Arg Lys Lys Ser Gln Leu Phe Arg Ser
                405                 410                 415

Asn Val Leu Leu Val Pro Leu Gly Asp Asp Phe Arg Tyr Asp Lys Pro
            420                 425                 430

Gln Glu Trp Asp Ala Gln Phe Phe Asn Tyr Gln Arg Leu Phe Asp Phe
    435                 440                 445

Phe Asn Ser Arg Pro Asn Leu His Val Gln Ala Gln Phe Gly Thr Leu
450                 455                 460

Ser Asp Tyr Phe Asp Ala Leu Tyr Lys Arg Thr Gly Val Glu Pro Gly
465                 470                 475                 480

Ala Arg Pro Pro Gly Phe Pro Val Leu Ser Gly Asp Phe Phe Ser Tyr
                485                 490                 495

Ala Asp Arg Glu Asp His Tyr Trp Thr Gly Tyr Tyr Thr Ser Arg Pro
            500                 505                 510

Phe Tyr Lys Ser Leu Asp Arg Val Leu Glu Ala His Leu Arg Gly Ala
    515                 520                 525

Glu Val Leu Tyr Ser Leu Ala Ala Ala His Ala Arg Arg Ser Gly Leu
530                 535                 540
```

```
Ala Gly Arg Tyr Pro Leu Ser Asp Phe Thr Leu Thr Glu Ala Arg
545                 550                 555                 560

Arg Thr Leu Gly Leu Phe Gln His His Asp Ala Ile Thr Gly Thr Ala
                565                 570                 575

Lys Glu Ala Val Val Val Asp Tyr Gly Val Arg Leu Leu Arg Ser Leu
            580                 585                 590

Val Asn Leu Lys Gln Val Ile Ile His Ala Ala His Tyr Leu Val Leu
        595                 600                 605

Gly Asp Lys Glu Thr Tyr His Phe Asp Pro Glu Ala Pro Phe Leu Gln
    610                 615                 620

Val Asp Thr Arg Leu Ser His Asp Ala Leu Pro Glu Arg Thr Val
625                 630                 635                 640

Ile Gln Leu Asp Ser Ser Pro Arg Phe Val Val Leu Phe Asn Pro Leu
                645                 650                 655

Glu Gln Glu Arg Phe Ser Met Val Ser Leu Leu Val Asn Ser Pro Arg
                660                 665                 670

Val Arg Val Leu Ser Glu Glu Gly Gln Pro Leu Ala Val Gln Ile Ser
            675                 680                 685

Ala His Trp Ser Ser Ala Thr Glu Ala Val Pro Asp Val Tyr Gln Val
    690                 695                 700

Ser Val Pro Val Arg Leu Pro Ala Leu Gly Leu Gly Val Leu Gln Leu
705                 710                 715                 720

Gln Leu Gly Leu Asp Gly His Arg Thr Leu Pro Ser Ser Val Arg Ile
                725                 730                 735

Tyr Leu His Gly Arg Gln Leu Ser Val Ser Arg His Glu Ala Phe Pro
                740                 745                 750

Leu Arg Val Ile Asp Ser Gly Thr Ser Asp Phe Ala Leu Ser Asn Arg
            755                 760                 765

Tyr Met Gln Val Trp Phe Ser Gly Leu Thr Gly Leu Leu Lys Ser Ile
    770                 775                 780

Arg Arg Val Asp Glu Glu His Glu Gln Gln Val Asp Met Gln Val Leu
785                 790                 795                 800

Val Tyr Gly Thr Arg Thr Ser Lys Asp Lys Ser Gly Ala Tyr Leu Phe
                805                 810                 815

Leu Pro Asp Gly Glu Ala Lys Pro Tyr Val Pro Lys Glu Pro Pro Val
            820                 825                 830

Leu Arg Val Thr Glu Gly Pro Phe Phe Ser Glu Val Ala Tyr Tyr
                835                 840                 845

Glu His Ile His Gln Ala Val Arg Leu Tyr Asn Leu Pro Gly Val Glu
    850                 855                 860

Gly Leu Ser Leu Asp Ile Ser Ser Leu Val Asp Ile Arg Asp Tyr Val
865                 870                 875                 880

Asn Lys Glu Leu Ala Leu His Ile His Thr Asp Ile Asp Ser Gln Gly
                885                 890                 895

Ile Phe Phe Thr Asp Leu Asn Gly Phe Gln Val Gln Pro Arg Arg Tyr
                900                 905                 910

Leu Lys Lys Leu Pro Leu Gln Ala Asn Phe Tyr Pro Met Pro Val Met
            915                 920                 925

Ala Tyr Ile Gln Asp Ala Gln Lys Arg Leu Thr His Thr Ala Gln
    930                 935                 940

Ala Leu Gly Val Ser Ser Leu Lys Asp Gly Gln Leu Glu Val Ile Leu
945                 950                 955                 960

Asp Arg Arg Leu Met Gln Asp Asp Asn Arg Gly Leu Gly Gln Gly Leu
```

-continued

```
                    965                 970                 975
Lys Asp Asn Lys Arg Thr Cys Asn Arg Phe Arg Leu Leu Glu Arg
            980                 985                 990
Arg Thr Val Gly Ser Glu Val Gln Asp Ser His Ser Thr Ser Tyr Pro
        995                1000                1005
Ser Leu Leu Ser His Leu Thr Ser Met Tyr Leu Asn Ala Pro Ala
       1010                1015                1020
Leu Ala Leu Pro Val Ala Arg Met Gln Leu Pro Gly Pro Gly Leu
       1025                1030                1035
Arg Ser Phe His Pro Leu Ala Ser Ser Leu Pro Cys Asp Phe His
       1040                1045                1050
Leu Leu Asn Leu Arg Thr Leu Gln Ala Glu Glu Asp Thr Leu Pro
       1055                1060                1065
Ser Ala Glu Thr Ala Leu Ile Leu His Arg Lys Gly Phe Asp Cys
       1070                1075                1080
Gly Leu Glu Ala Lys Asn Leu Gly Phe Asn Cys Thr Thr Ser Gln
       1085                1090                1095
Gly Lys Val Ala Leu Gly Ser Leu Phe His Gly Leu Asp Val Val
       1100                1105                1110
Phe Leu Gln Pro Thr Ser Leu Thr Leu Leu Tyr Pro Leu Ala Ser
       1115                1120                1125
Pro Ser Asn Ser Thr Asp Val Tyr Leu Glu Pro Met Glu Ile Ala
       1130                1135                1140
Thr Phe Arg Leu Arg Leu Gly
       1145                1150

<210> SEQ ID NO 3
<211> LENGTH: 1150
<212> TYPE: PRT
<213> ORGANISM: Mus musculus

<400> SEQUENCE: 3

Met Lys Leu Ser Arg Gln Phe Thr Val Phe Gly Ser Ala Ile Phe Cys
1               5                  10                  15
Val Val Ile Phe Ser Leu Tyr Leu Met Leu Asp Arg Gly His Leu Asp
            20                  25                  30
Tyr Pro Arg Gly Pro Arg Gln Glu Gly Ser Phe Pro Gln Gly Gln Leu
        35                  40                  45
Ser Ile Leu Gln Glu Lys Ile Asp His Leu Glu Arg Leu Leu Ala Glu
    50                  55                  60
Asn Asn Glu Ile Ile Ser Asn Ile Arg Asp Ser Val Ile Asn Leu Ser
65                  70                  75                  80
Glu Ser Val Glu Asp Gly Pro Arg Gly Ser Pro Gly Asn Ala Ser Gln
            85                  90                  95
Gly Ser Ile His Leu His Ser Pro Gln Leu Ala Leu Gln Ala Asp Pro
        100                 105                 110
Arg Asp Cys Leu Phe Ala Ser Gln Ser Gly Ser Gln Pro Arg Asp Val
    115                 120                 125
Gln Met Leu Asp Val Tyr Asp Leu Ile Pro Phe Asp Asn Pro Asp Gly
130                 135                 140
Gly Val Trp Lys Gln Gly Phe Asp Ile Lys Tyr Glu Ala Asp Glu Trp
145                 150                 155                 160
Asp His Glu Pro Leu Gln Val Phe Val Val Pro His Ser His Asn Asp
            165                 170                 175
```

-continued

```
Pro Gly Trp Leu Lys Thr Phe Asn Asp Tyr Phe Arg Asp Lys Thr Gln
            180                 185                 190
Tyr Ile Phe Asn Asn Met Val Leu Lys Leu Lys Glu Asp Ser Ser Arg
        195                 200                 205
Lys Phe Met Trp Ser Glu Ile Ser Tyr Leu Ala Lys Trp Trp Asp Ile
    210                 215                 220
Ile Asp Ile Pro Lys Lys Glu Ala Val Lys Ser Leu Leu Gln Asn Gly
225                 230                 235                 240
Gln Leu Glu Ile Val Thr Gly Gly Trp Val Met Pro Asp Glu Ala Thr
                245                 250                 255
Pro His Tyr Phe Ala Leu Ile Asp Gln Leu Ile Glu Gly His Gln Trp
            260                 265                 270
Leu Glu Lys Asn Leu Gly Val Lys Pro Arg Ser Gly Trp Ala Ile Asp
        275                 280                 285
Pro Phe Gly His Ser Pro Thr Met Ala Tyr Leu Leu Lys Arg Ala Gly
    290                 295                 300
Phe Ser His Met Leu Ile Gln Arg Val His Tyr Ala Ile Lys Lys His
305                 310                 315                 320
Phe Ser Leu His Lys Thr Leu Glu Phe Phe Trp Arg Gln Asn Trp Asp
                325                 330                 335
Leu Gly Ser Ala Thr Asp Ile Leu Cys His Met Met Pro Phe Tyr Ser
            340                 345                 350
Tyr Asp Ile Pro His Thr Cys Gly Pro Asp Pro Lys Ile Cys Cys Gln
        355                 360                 365
Phe Asp Phe Lys Arg Leu Pro Gly Gly Arg Tyr Gly Cys Pro Trp Gly
    370                 375                 380
Val Pro Pro Glu Ala Ile Ser Pro Gly Asn Val Gln Ser Arg Ala Gln
385                 390                 395                 400
Met Leu Leu Asp Gln Tyr Arg Lys Lys Ser Lys Leu Phe Arg Thr Lys
                405                 410                 415
Val Leu Leu Ala Pro Leu Gly Asp Asp Phe Arg Phe Ser Glu Tyr Thr
            420                 425                 430
Glu Trp Asp Leu Gln Cys Arg Asn Tyr Glu Gln Leu Phe Ser Tyr Met
        435                 440                 445
Asn Ser Gln Pro His Leu Lys Val Lys Ile Gln Phe Gly Thr Leu Ser
    450                 455                 460
Asp Tyr Phe Asp Ala Leu Glu Lys Ala Val Ala Glu Lys Lys Ser
465                 470                 475                 480
Ser Gln Ser Val Phe Pro Ala Leu Ser Gly Asp Phe Phe Thr Tyr Ala
                485                 490                 495
Asp Arg Asp Asp His Tyr Trp Ser Gly Tyr Phe Thr Ser Arg Pro Phe
            500                 505                 510
Tyr Lys Arg Met Asp Arg Ile Met Glu Ser Arg Ile Arg Ala Ala Glu
        515                 520                 525
Ile Leu Tyr Gln Leu Ala Leu Lys Gln Ala Gln Lys Tyr Lys Ile Asn
    530                 535                 540
Lys Phe Leu Ser Ser Pro His Tyr Thr Thr Leu Thr Glu Ala Arg Arg
545                 550                 555                 560
Asn Leu Gly Leu Phe Gln His His Asp Ala Ile Thr Gly Thr Ala Lys
                565                 570                 575
Asp Trp Val Val Val Asp Tyr Gly Thr Arg Leu Phe Gln Ser Leu Asn
            580                 585                 590
Ser Leu Glu Lys Ile Ile Gly Asp Ser Ala Phe Leu Leu Ile Leu Lys
```

-continued

```
                595                 600                 605
Asp Lys Lys Leu Tyr Gln Ser Asp Pro Ser Lys Ala Phe Leu Glu Met
610                 615                 620

Asp Thr Lys Gln Ser Ser Gln Asp Ser Leu Pro Gln Lys Ile Ile Ile
625                 630                 635                 640

Gln Leu Ser Ala Gln Glu Pro Arg Tyr Leu Val Val Tyr Asn Pro Phe
                645                 650                 655

Glu Gln Glu Arg His Ser Val Val Ser Ile Arg Val Asn Ser Ala Thr
                660                 665                 670

Val Lys Val Leu Ser Asp Ser Gly Lys Pro Val Glu Val Gln Val Ser
                675                 680                 685

Ala Val Trp Asn Asp Met Arg Thr Ile Ser Gln Ala Ala Tyr Glu Val
690                 695                 700

Ser Phe Leu Ala His Ile Pro Pro Leu Gly Leu Lys Val Phe Lys Ile
705                 710                 715                 720

Leu Glu Ser Gln Ser Ser Ser His Leu Ala Asp Tyr Val Leu Tyr
                725                 730                 735

Asn Asn Asp Gly Leu Ala Glu Asn Gly Ile Phe His Val Lys Asn Met
                740                 745                 750

Val Asp Ala Gly Asp Ala Ile Thr Ile Glu Asn Pro Phe Leu Ala Ile
                755                 760                 765

Trp Phe Asp Arg Ser Gly Leu Met Glu Lys Val Arg Arg Lys Glu Asp
770                 775                 780

Ser Arg Gln His Glu Leu Lys Val Gln Phe Leu Trp Tyr Gly Thr Thr
785                 790                 795                 800

Asn Lys Arg Asp Lys Ser Gly Ala Tyr Leu Phe Leu Pro Asp Gly Gln
                805                 810                 815

Gly Gln Pro Tyr Val Ser Leu Arg Pro Pro Phe Val Arg Val Thr Arg
                820                 825                 830

Gly Arg Ile Tyr Ser Asp Val Thr Cys Phe Leu Glu His Val Thr His
                835                 840                 845

Lys Val Arg Leu Tyr Asn Ile Gln Gly Ile Glu Gly Gln Ser Met Glu
850                 855                 860

Val Ser Asn Ile Val Asn Ile Arg Asn Val His Asn Arg Glu Ile Val
865                 870                 875                 880

Met Arg Ile Ser Ser Lys Ile Asn Asn Gln Asn Arg Tyr Tyr Thr Asp
                885                 890                 895

Leu Asn Gly Tyr Gln Ile Gln Pro Arg Arg Thr Met Ser Lys Leu Pro
                900                 905                 910

Leu Gln Ala Asn Val Tyr Pro Met Cys Thr Met Ala Tyr Ile Gln Asp
                915                 920                 925

Ala Glu His Arg Leu Thr Leu Leu Ser Ala Gln Ser Leu Gly Ala Ser
                930                 935                 940

Ser Met Ala Ser Gly Gln Ile Glu Val Phe Met Asp Arg Arg Leu Met
945                 950                 955                 960

Gln Asp Asp Asn Arg Gly Leu Gly Gln Gly Val His Asp Asn Lys Ile
                965                 970                 975

Thr Ala Asn Leu Phe Arg Ile Leu Leu Glu Lys Arg Ser Ala Val Asn
                980                 985                 990

Met Glu Glu Glu Lys Lys Ser Pro  Val Ser Tyr Pro Ser  Leu Leu Ser
                995                 1000                 1005

His Met  Thr Ser Ser Phe Leu  Asn His Pro Phe Leu  Pro Met Val
                1010                 1015                 1020
```

-continued

Leu Ser Gly Gln Leu Pro Ser Pro Ala Phe Glu Leu Leu Ser Glu
    1025                1030                1035

Phe Pro Leu Leu Gln Ser Ser Leu Pro Cys Asp Ile His Leu Val
    1040                1045                1050

Asn Leu Arg Thr Ile Gln Ser Lys Met Gly Lys Gly Tyr Ser Asp
    1055                1060                1065

Glu Ala Ala Leu Ile Leu His Arg Lys Gly Phe Asp Cys Gln Phe
    1070                1075                1080

Ser Ser Arg Gly Ile Gly Leu Pro Cys Ser Thr Thr Gln Gly Lys
    1085                1090                1095

Met Ser Val Leu Lys Leu Phe Asn Lys Phe Ala Val Glu Ser Leu
    1100                1105                1110

Val Pro Ser Ser Leu Ser Leu Met His Ser Pro Pro Asp Ala Gln
    1115                1120                1125

Asn Met Ser Glu Val Ser Leu Ser Pro Met Glu Ile Ser Thr Phe
    1130                1135                1140

Arg Ile Arg Leu Arg Trp Thr
    1145                1150

<210> SEQ ID NO 4
<211> LENGTH: 1152
<212> TYPE: PRT
<213> ORGANISM: Mus musculus

<400> SEQUENCE: 4

Met Lys Leu Lys Lys Gln Val Thr Val Cys Gly Ala Ala Ile Phe Cys
1               5                   10                  15

Val Ala Val Phe Ser Leu Tyr Leu Met Leu Asp Arg Val Gln His Asp
                20                  25                  30

Pro Ala Arg His Gln Asn Gly Gly Asn Phe Pro Arg Ser Gln Ile Ser
            35                  40                  45

Val Leu Gln Asn Arg Ile Glu Gln Leu Glu Gln Leu Leu Glu Glu Asn
        50                  55                  60

His Asp Ile Ile Ser Arg Ile Lys Asp Ser Val Leu Glu Leu Thr Ala
65                  70                  75                  80

Asn Ala Glu Gly Pro Pro Ala Leu Leu Pro Tyr His Thr Ala Asn Gly
                85                  90                  95

Ser Trp Ala Val Leu Pro Glu Pro Arg Pro Ser Phe Phe Ser Val Ser
            100                 105                 110

Pro Gln Asp Cys Gln Phe Ala Leu Gly Gly Arg Gly Gln Lys Pro Glu
        115                 120                 125

Leu Gln Met Leu Thr Val Ser Glu Asp Leu Pro Phe Asp Asn Val Glu
    130                 135                 140

Gly Gly Val Trp Arg Gln Gly Phe Asp Ile Ser Tyr Ser Pro Asn Asp
145                 150                 155                 160

Trp Asp Thr Glu Asp Leu Gln Val Phe Val Pro His Ser His Asn
                165                 170                 175

Asp Pro Gly Trp Ile Lys Thr Phe Asp Lys Tyr Tyr Thr Glu Gln Thr
            180                 185                 190

Gln His Ile Leu Asn Ser Met Val Ser Lys Leu Gln Asp Pro Arg
        195                 200                 205

Arg Arg Phe Leu Trp Ala Glu Val Ser Phe Phe Ala Lys Trp Trp Asp
    210                 215                 220

Asn Ile Ser Ala Gln Lys Arg Ala Ala Val Arg Arg Leu Val Gly Asn

```
            225                 230                 235                 240
Gly Gln Leu Glu Ile Ala Thr Gly Gly Trp Val Met Pro Asp Glu Ala
                    245                 250                 255

Asn Ser His Tyr Phe Ala Leu Val Asp Gln Leu Ile Glu Gly His Gln
                260                 265                 270

Trp Leu Glu Arg Asn Leu Gly Ala Thr Pro Arg Ser Gly Trp Ala Val
            275                 280                 285

Asp Pro Phe Gly His Ser Ser Thr Met Pro Tyr Leu Leu Arg Arg Ala
        290                 295                 300

Asn Leu Thr Ser Met Leu Ile Gln Arg Val His Tyr Ala Ile Lys Lys
305                 310                 315                 320

His Phe Ala Ala Thr His Ser Leu Glu Phe Met Trp Arg Gln Met Trp
                    325                 330                 335

Asp Ser Asp Ser Thr Asp Ile Phe Cys His Met Met Pro Phe Tyr
                340                 345                 350

Ser Tyr Asp Val Pro His Thr Cys Gly Pro Asp Pro Lys Ile Cys Cys
            355                 360                 365

Gln Phe Asp Phe Lys Arg Leu Pro Gly Gly Arg Ile Asn Cys Pro Trp
        370                 375                 380

Lys Val Pro Pro Arg Ala Ile Thr Glu Ala Asn Val Ala Asp Arg Ala
385                 390                 395                 400

Ala Leu Leu Leu Asp Gln Tyr Arg Lys Lys Ser Arg Leu Phe Arg Ser
                    405                 410                 415

Asn Val Leu Leu Val Pro Leu Gly Asp Asp Phe Arg Tyr Asp Lys Pro
                420                 425                 430

Gln Glu Trp Asp Ala Gln Phe Phe Asn Tyr Gln Arg Leu Phe Asp Phe
            435                 440                 445

Leu Asn Ser Lys Pro Glu Phe His Val Gln Ala Gln Phe Gly Thr Leu
        450                 455                 460

Ser Glu Tyr Phe Asp Ala Leu Tyr Lys Arg Thr Gly Val Glu Pro Gly
465                 470                 475                 480

Ala Arg Pro Pro Gly Phe Pro Val Leu Ser Gly Asp Phe Phe Ser Tyr
                    485                 490                 495

Ala Asp Arg Glu Asp His Tyr Trp Thr Gly Tyr Tyr Thr Ser Arg Pro
                500                 505                 510

Phe Tyr Lys Ser Leu Asp Arg Val Leu Glu Ala His Leu Arg Gly Ala
            515                 520                 525

Glu Ile Leu Tyr Ser Leu Ala Leu Ala His Ala Arg Arg Ser Gly Leu
        530                 535                 540

Ala Gly Gln Tyr Pro Leu Ser Asp Phe Ala Leu Leu Thr Glu Ala Arg
545                 550                 555                 560

Arg Thr Leu Gly Leu Phe Gln His His Asp Ala Ile Thr Gly Thr Ala
                    565                 570                 575

Lys Glu Ala Val Val Val Asp Tyr Gly Val Arg Leu Leu Arg Ser Leu
                580                 585                 590

Val Ser Leu Lys Gln Val Ile Ile Asn Ala Ala His Tyr Leu Val Leu
            595                 600                 605

Gly Asp Gln Glu Thr Tyr Ser Phe Asp Pro Gly Thr Pro Phe Leu Gln
        610                 615                 620

Met Asp Asp Ser Arg Val Ser His Asp Ala Leu Pro Glu Arg Thr Val
625                 630                 635                 640

Ile Arg Leu Asp Ser Ser Pro Arg Phe Val Val Phe Asn Pro Leu
                    645                 650                 655
```

-continued

Glu Gln Glu Arg Leu Ser Val Ser Leu Val Asn Ser Pro Arg
            660                 665             670

Val Arg Val Leu Ser Glu Gly Gln Pro Leu Ser Val Gln Ile Ser
        675                 680             685

Val His Trp Ser Ser Ala Thr Asp Met Val Pro Asp Val Tyr Gln Val
    690                 695             700

Ser Val Pro Val Arg Leu Pro Gly Leu Gly Leu Val Leu Gln Leu
705                 710             715                 720

Gln Pro Asp Leu Asp Gly Pro Tyr Thr Leu Gln Ser Ser Val Arg Val
                725             730                 735

Tyr Leu Asn Gly Val Lys Leu Ser Ser Arg Gln Ser Ala Phe Pro
            740                 745             750

Val Arg Val Val Asp Ser Gly Ala Ser Asp Phe Ala Ile Ser Asn Arg
            755                 760             765

Tyr Met Gln Val Trp Phe Ser Gly Leu Thr Gly Leu Leu Lys Ser Ile
    770                 775             780

Arg Arg Val Asp Glu Glu Gln Glu Gln Gln Met Glu Leu Glu Phe Leu
785                 790             795                 800

Val Tyr Gly Thr Arg Thr Ser Lys Asp Lys Ser Gly Ala Tyr Leu Phe
            805                 810             815

Leu Pro Asp Ser Glu Ala Lys Pro Tyr Val Pro Lys Lys Pro Pro Val
            820                 825             830

Leu Arg Val Thr Glu Gly Pro Phe Phe Ser Glu Val Ala Val Tyr Tyr
            835                 840             845

Glu His Phe His Gln Val Ile Arg Leu Tyr Asn Leu Pro Gly Val Glu
    850                 855             860

Gly Leu Ser Leu Asp Met Ser Phe Gln Val Asp Ile Arg Asp Tyr Val
865                 870             875                 880

Asn Lys Glu Leu Ala Leu Arg Ile His Thr Asp Ile Asp Ser Gln Gly
                885             890                 895

Thr Phe Phe Thr Asp Leu Asn Gly Phe Gln Ile Gln Pro Arg Gln Tyr
                900             905                 910

Leu Lys Lys Leu Pro Leu Gln Ala Asn Phe Tyr Pro Met Pro Val Met
            915                 920             925

Ala Tyr Ile Gln Asp Ser Gln Arg Arg Leu Thr Leu His Thr Ala Gln
            930                 935             940

Ala Leu Gly Val Ser Ser Leu Gly Asn Gly Gln Leu Glu Val Ile Leu
945                 950             955                 960

Asp Arg Arg Leu Met Gln Asp Asp Asn Arg Gly Leu Gly Gln Gly Leu
                965             970                 975

Lys Asp Asn Lys Ile Thr Cys Asn Arg Phe Arg Leu Leu Leu Glu Arg
            980                 985             990

Arg Thr Thr Met Ser Pro Glu Val His Gln Glu Gln Glu Arg Ser Thr
            995                 1000            1005

Ser Tyr Pro Ser Leu Leu Ser His Leu Thr Ser Met Tyr Leu Ser
    1010                1015            1020

Thr Pro Pro Leu Val Leu Pro Val Ala Lys Arg Gln Gly Thr Ser
    1025                1030            1035

Pro Ala Leu Arg Ser Phe His Pro Leu Ala Ser Pro Leu Pro Cys
    1040                1045            1050

Asp Phe His Leu Leu Asn Leu Arg Met Leu Pro Ala Glu Asp Thr
    1055                1060            1065

-continued

```
Leu Pro Ala Thr Asp Ser Ala Leu Ile Leu His Arg Lys Gly Phe
    1070                1075                1080
Asp Cys Gly Leu Glu Ala Lys Asn Leu Gly Phe Asn Cys Thr Thr
    1085                1090                1095
Ser Gln Gly Lys Leu Ala Leu Gly Ser Leu Phe His Gly Leu Asp
    1100                1105                1110
Val Thr Phe Leu Gln Pro Thr Ser Leu Thr Leu Leu Tyr Pro Leu
    1115                1120                1125
Ala Ser Pro Ser Asn Ser Thr Asp Ile Ser Leu Glu Pro Met Glu
    1130                1135                1140
Ile Ser Thr Phe Arg Leu Arg Leu Gly
    1145                1150

<210> SEQ ID NO 5
<211> LENGTH: 1148
<212> TYPE: PRT
<213> ORGANISM: Rattus norvegicus

<400> SEQUENCE: 5

Met Lys Leu Ser Arg Gln Phe Thr Val Phe Gly Ser Ala Ile Phe Cys
1               5                   10                  15
Val Val Ile Phe Ser Leu Tyr Leu Met Leu Asp Arg Gly His Leu Asp
                20                  25                  30
Tyr Pro Arg Gly Pro Arg Gln Glu Gly Ser Phe Pro Gln Gly Gln Leu
            35                  40                  45
Ser Ile Leu Gln Glu Lys Ile Asp His Leu Glu Arg Leu Leu Ala Glu
        50                  55                  60
Asn Asn Glu Ile Ile Ser Asn Ile Arg Asp Ser Val Ile Asn Leu Ser
65                  70                  75                  80
Glu Ser Val Glu Asp Gly Pro Arg Gly Pro Ala Gly Asn Ala Ser Gln
                85                  90                  95
Gly Ser Ala His Leu His Ser Ala Gln Leu Ala Leu Gln Ala Asp Pro
            100                 105                 110
Lys Asp Cys Leu Phe Ala Ser Gln Ser Gly Asn Gln His Arg Asp Val
        115                 120                 125
Gln Met Leu Asp Val Tyr Asp Leu Ile Pro Phe Asp Asn Pro Asp Gly
    130                 135                 140
Gly Val Trp Lys Gln Gly Phe Asp Ile Lys Tyr Glu Ala Asp Glu Trp
145                 150                 155                 160
Asp Arg Glu Pro Leu Gln Val Phe Val Val Pro His Ser His Asn Asp
                165                 170                 175
Pro Gly Trp Leu Lys Thr Phe Asn Asp Tyr Phe Arg Asp Lys Thr Gln
            180                 185                 190
Tyr Ile Phe Asn Asn Met Val Leu Lys Leu Lys Glu Asp Ser Ser Arg
        195                 200                 205
Lys Phe Ile Trp Ser Glu Ile Ser Tyr Leu Ala Lys Trp Trp Asp Ile
    210                 215                 220
Ile Asp Asn Pro Lys Lys Glu Ala Val Lys Ser Leu Leu Gln Asn Gly
225                 230                 235                 240
Gln Leu Glu Ile Val Thr Gly Gly Trp Val Met Ala Asp Glu Ala Thr
                245                 250                 255
Thr His Tyr Phe Ala Leu Ile Asp Gln Leu Ile Glu Gly His Gln Trp
            260                 265                 270
Leu Glu Lys Asn Leu Gly Val Lys Pro Arg Ser Gly Trp Ala Ile Asp
        275                 280                 285
```

-continued

Pro Phe Gly His Ser Pro Thr Met Thr Tyr Leu Leu Lys Arg Ala Gly
    290                 295                 300

Phe Ser His Met Leu Ile Gln Arg Val His Tyr Ser Val Lys Lys His
305                 310                 315                 320

Phe Ser Leu Gln Lys Thr Leu Glu Phe Phe Trp Arg Gln Asn Trp Asp
                325                 330                 335

Leu Gly Ser Thr Thr Asp Ile Leu Cys His Met Met Pro Phe Tyr Ser
            340                 345                 350

Tyr Asp Ile Pro His Thr Cys Gly Pro Asp Pro Lys Ile Cys Cys Gln
        355                 360                 365

Phe Asp Phe Lys Arg Leu Pro Gly Gly Arg Tyr Gly Cys Pro Trp Gly
370                 375                 380

Val Pro Pro Glu Ala Ile Ser Pro Gly Asn Val Gln Ser Arg Ala Gln
385                 390                 395                 400

Met Leu Leu Asp Gln Tyr Arg Lys Lys Ser Lys Leu Phe Arg Thr Lys
                405                 410                 415

Val Leu Leu Ala Pro Leu Gly Asp Asp Phe Arg Phe Ser Glu Tyr Thr
            420                 425                 430

Glu Trp Asp Leu Gln Tyr Arg Asn Tyr Glu Gln Leu Phe Ser Tyr Met
        435                 440                 445

Asn Ser Gln Pro His Leu Lys Val Lys Ile Gln Phe Gly Thr Leu Ser
450                 455                 460

Asp Tyr Phe Asp Ala Leu Glu Lys Ser Val Ala Ala Glu Lys Lys Gly
465                 470                 475                 480

Gly Gln Ser Val Phe Pro Ala Leu Ser Gly Asp Phe Phe Thr Tyr Ala
                485                 490                 495

Asp Arg Asp Asp His Tyr Trp Ser Gly Tyr Phe Thr Ser Arg Pro Phe
            500                 505                 510

Tyr Lys Arg Met Asp Arg Ile Met Glu Ser Arg Leu Arg Thr Ala Glu
        515                 520                 525

Ile Leu Tyr His Leu Ala Leu Lys Gln Ala Gln Lys Tyr Lys Ile Asn
530                 535                 540

Lys Phe Leu Ser Ser Pro His Tyr Thr Thr Leu Thr Glu Ala Arg Arg
545                 550                 555                 560

Asn Leu Gly Leu Phe Gln His His Asp Ala Ile Thr Gly Thr Ala Lys
                565                 570                 575

Asp Trp Val Val Val Asp Tyr Gly Thr Arg Leu Phe Gln Ser Leu Asn
            580                 585                 590

Ser Leu Glu Lys Ile Ile Gly Asp Ser Ala Phe Leu Leu Ile Leu Lys
        595                 600                 605

Asp Lys Lys Leu Tyr Gln Ser Asp Pro Ser Lys Ala Phe Leu Glu Met
610                 615                 620

Asp Thr Lys Gln Ser Ser Gln Asp Ser Leu Pro Lys Lys Asn Ile Ile
625                 630                 635                 640

Gln Leu Ser Ala Gln Glu Pro Arg Tyr Leu Val Tyr Asn Pro Phe
                645                 650                 655

Glu Gln Glu Arg His Ser Val Val Ser Val Arg Val Asn Ser Ala Thr
            660                 665                 670

Val Lys Val Leu Ser Asp Leu Gly Lys Ala Val Glu Val Gln Val Ser
        675                 680                 685

Ala Val Trp Lys Asp Met Arg Thr Thr Ser Gln Ala Ala Tyr Glu Val
690                 695                 700

```
Ala Phe Leu Ala His Leu Pro Pro Leu Gly Leu Lys Val Tyr Lys Ile
705                 710                 715                 720

Leu Glu Ser Gln Ser Ser Ser His Leu Ala Asp Tyr Phe Leu Tyr
            725                 730                 735

Asn Asn Asp Gly Gln Ala Glu Ser Gly Ile Phe His Met Lys Asn Met
            740                 745                 750

Val Asp Ser Gly Asp Ala Ile Thr Ile Glu Asn Ser Phe Leu Thr Leu
            755                 760                 765

Gly Phe Asp Arg Ser Gly Leu Met Glu Lys Val Arg Arg Lys Glu Asp
            770                 775                 780

Asn Lys Gln Gln Glu Leu Lys Val Gln Phe Leu Trp Tyr Gly Thr Thr
785                 790                 795                 800

Asn Lys Arg Asp Lys Ser Gly Ala Tyr Leu Phe Leu Pro Asp Gly Gln
            805                 810                 815

Gly Gln Pro Tyr Val Ser Leu Arg Thr Pro Phe Val Arg Val Thr Arg
            820                 825                 830

Gly Arg Ile Tyr Ser Asp Val Thr Cys Phe Leu Glu His Val Thr His
            835                 840                 845

Lys Val Arg Leu Tyr His Ile Gln Gly Ile Glu Gly Gln Ser Met Glu
850                 855                 860

Val Ser Asn Ile Val Asp Ile Arg Ser Val His Asn Arg Glu Ile Val
865                 870                 875                 880

Met Arg Ile Ser Ser Lys Ile Asn Asn Gln Asn Arg Tyr Tyr Thr Asp
                885                 890                 895

Leu Asn Gly Tyr Gln Ile Gln Pro Arg Arg Thr Met Ala Lys Leu Pro
            900                 905                 910

Leu Gln Ala Asn Val Tyr Pro Met Ser Thr Met Ala Tyr Ile Gln Asp
            915                 920                 925

Ala Ala His Arg Leu Thr Leu Leu Ser Ala Gln Ser Leu Gly Ala Ser
930                 935                 940

Ser Met Ala Ser Gly Gln Ile Glu Val Phe Met Asp Arg Arg Leu Met
945                 950                 955                 960

Gln Asp Asp Asn Arg Gly Leu Gly Gln Gly Val His Asp Asn Lys Ile
            965                 970                 975

Thr Ala Asn Leu Phe Arg Ile Leu Leu Glu Lys Arg Asn Gly Met Asn
            980                 985                 990

Met Glu Glu Asp Lys Lys Ser Pro Val Ser Tyr Pro Ser Leu Leu Ser
            995                 1000                1005

His Met Thr Ser Ala Phe Leu Asn His Pro Phe Leu Pro Met Val
    1010                1015                1020

Leu Ser Gly Gln Leu Pro Ser Pro Ala Ile Glu Leu Leu Ser Glu
    1025                1030                1035

Phe Arg Leu Leu Gln Ser Ser Leu Pro Cys Asp Ile His Leu Val
    1040                1045                1050

Asn Leu Arg Thr Ile Gln Ser Lys Val Gly Lys Gly Tyr Ser Asp
    1055                1060                1065

Glu Ala Ala Leu Ile Leu His Arg Lys Val Phe Asp Cys Gln Leu
    1070                1075                1080

Ser Ser Arg Ala Met Gly Leu Pro Cys Ser Thr Thr Gln Gly Lys
    1085                1090                1095

Met Ser Ile Pro Lys Leu Phe Asn Asn Phe Ala Val Glu Ser Phe
    1100                1105                1110

Ile Pro Ser Ser Leu Ser Leu Met His Ser Pro Pro Asp Ala Gln
```

```
            1115                1120               1125

Asn Thr Ser Glu Val Ser Leu Ser Pro Met Glu Ile Ser Thr Ser
    1130                1135               1140

Arg Ile Arg Leu Arg
    1145

<210> SEQ ID NO 6
<211> LENGTH: 1164
<212> TYPE: PRT
<213> ORGANISM: Rattus norvegicus

<400> SEQUENCE: 6

Met Lys Leu Lys Lys Gln Val Thr Val Cys Gly Ala Ala Ile Phe Cys
1               5                   10                  15

Val Ala Val Phe Ser Leu Tyr Leu Met Leu Asp Arg Val Gln His Asp
            20                  25                  30

Pro Ala Arg His Gln Asn Gly Gly Asn Phe Pro Arg Ser Gln Ile Ser
        35                  40                  45

Val Leu Gln Asn Arg Ile Glu Gln Leu Glu Gln Leu Leu Glu Glu Asn
    50                  55                  60

His Glu Ile Ile Ser His Ile Lys Asp Ser Val Leu Glu Leu Thr Ala
65                  70                  75                  80

Asn Ala Glu Gly Pro Pro Ala Leu Leu Pro Tyr His Thr Ala Asn Gly
                85                  90                  95

Ser Trp Ala Val Leu Pro Glu Pro Arg Pro Ser Phe Ser Val Ser
            100                 105                 110

Pro Glu Asp Cys Gln Phe Ala Leu Gly Gly Arg Gly Gln Lys Pro Glu
        115                 120                 125

Leu Gln Met Leu Thr Val Ser Glu Asp Leu Pro Phe Asp Asn Val Glu
    130                 135                 140

Gly Gly Val Trp Arg Gln Gly Phe Asp Ile Ser Tyr Ser Pro Asn Asp
145                 150                 155                 160

Trp Asp Ala Glu Asp Leu Gln Val Phe Val Val Pro His Ser His Asn
                165                 170                 175

Asp Pro Gly Trp Ile Lys Thr Phe Asp Lys Tyr Tyr Thr Glu Gln Thr
            180                 185                 190

Gln His Ile Leu Asn Ser Met Val Ser Lys Leu Gln Glu Asp Pro Arg
        195                 200                 205

Arg Arg Phe Leu Trp Ala Glu Val Ser Phe Phe Ala Lys Trp Trp Asp
    210                 215                 220

Asn Ile Ser Ala Gln Lys Arg Ala Ala Val Arg Arg Leu Val Gly Asn
225                 230                 235                 240

Gly Gln Leu Glu Ile Ala Thr Gly Gly Trp Val Met Pro Asp Glu Ala
                245                 250                 255

Asn Ser His Tyr Phe Ala Leu Val Asp Gln Leu Ile Glu Gly His Gln
            260                 265                 270

Trp Leu Glu Arg Asn Leu Gly Ala Thr Pro Arg Ser Gly Trp Ala Val
        275                 280                 285

Asp Pro Phe Gly His Ser Ser Thr Met Pro Tyr Leu Leu Arg Arg Ala
    290                 295                 300

Asn Leu Thr Ser Met Leu Ile Gln Arg Val His Tyr Ala Ile Lys Lys
305                 310                 315                 320

His Phe Ala Ala Thr His Ser Leu Glu Phe Met Trp Arg Gln Thr Trp
                325                 330                 335
```

-continued

```
Asp Ser Asp Ser Ser Thr Asp Ile Phe Cys His Met Met Pro Phe Tyr
            340                 345                 350
Ser Tyr Asp Val Pro His Thr Cys Gly Pro Asp Pro Lys Ile Cys Cys
        355                 360                 365
Gln Phe Asp Phe Lys Arg Leu Pro Gly Gly Arg Ile Asn Cys Pro Trp
    370                 375                 380
Lys Val Pro Pro Arg Ala Ile Thr Glu Ala Asn Val Ala Asp Arg Ala
385                 390                 395                 400
Ala Leu Leu Leu Asp Gln Tyr Arg Lys Lys Ser Arg Leu Phe Arg Ser
                405                 410                 415
Ser Val Leu Leu Val Pro Leu Gly Asp Asp Phe Arg Tyr Asp Lys Pro
            420                 425                 430
Gln Glu Trp Asp Ala Gln Phe Phe Asn Tyr Gln Arg Leu Phe Asp Phe
        435                 440                 445
Leu Asn Ser Lys Pro Glu Phe His Val Gln Ala Gln Phe Gly Thr Leu
    450                 455                 460
Ser Glu Tyr Phe Asp Ala Leu Tyr Lys Arg Thr Gly Val Glu Pro Gly
465                 470                 475                 480
Ala Arg Pro Pro Gly Phe Pro Val Leu Ser Gly Asp Phe Phe Ser Tyr
                485                 490                 495
Ala Asp Arg Glu Asp His Tyr Trp Thr Gly Tyr Tyr Thr Ser Arg Pro
            500                 505                 510
Phe Tyr Lys Ser Leu Asp Arg Val Leu Glu Thr His Leu Arg Gly Ala
        515                 520                 525
Glu Val Leu Tyr Ser Leu Ala Leu Ala His Ala Arg Arg Ser Gly Leu
    530                 535                 540
Thr Gly Gln Tyr Pro Leu Ser Asp Tyr Ala Val Leu Thr Glu Ala Arg
545                 550                 555                 560
Arg Thr Leu Gly Leu Phe Gln His His Asp Ala Ile Thr Gly Thr Ala
                565                 570                 575
Lys Glu Ala Val Val Asp Tyr Gly Val Arg Leu Leu Arg Ser Leu
            580                 585                 590
Val Ser Leu Lys Gln Val Ile Ile Asn Ala Ala His Tyr Leu Val Leu
        595                 600                 605
Gly Asp Lys Glu Thr Tyr Ser Phe Asp Pro Arg Ala Pro Phe Leu Gln
    610                 615                 620
Met Asp Asp Ser Arg Val Ser His Asp Ala Leu Pro Glu Arg Thr Val
625                 630                 635                 640
Ile Arg Leu Asp Ser Ser Pro Arg Phe Val Val Phe Asn Pro Leu
                645                 650                 655
Glu Gln Glu Arg Leu Ser Val Val Ser Leu Leu Val Asn Ser Pro Arg
            660                 665                 670
Val Arg Val Leu Ser Glu Glu Gly Gln Pro Leu Ser Val Gln Ile Ser
        675                 680                 685
Val Gln Trp Ser Ser Ala Thr Asn Met Val Pro Asp Val Tyr Gln Val
    690                 695                 700
Ser Val Pro Val Arg Leu Pro Ala Leu Gly Leu Gly Val Leu Gln Leu
705                 710                 715                 720
Gln Pro Asp Leu Asp Gly Pro Tyr Thr Leu Gln Ser Ser Val His Val
                725                 730                 735
Tyr Leu Asn Gly Val Lys Leu Ser Val Ser Arg Gln Thr Thr Phe Pro
            740                 745                 750
Leu Arg Val Val Asp Ser Gly Thr Ser Asp Phe Ala Ile Ser Asn Arg
```

-continued

```
            755                 760                 765
Tyr Met Gln Val Trp Phe Ser Gly Leu Thr Gly Leu Leu Lys Ser Val
770                 775                 780
Arg Arg Val Asp Glu Glu Gln Glu Gln Gln Val Asp Met Lys Leu Phe
785                 790                 795                 800
Val Tyr Gly Thr Arg Thr Ser Lys Asp Lys Ser Gly Ala Tyr Leu Phe
                    805                 810                 815
Leu Pro Asp Asn Glu Ala Lys Pro Tyr Val Pro Lys Lys Pro Pro Val
                    820                 825                 830
Leu Arg Val Thr Glu Gly Pro Phe Phe Ser Glu Val Ala Ala Tyr Tyr
                    835                 840                 845
Glu His Phe His Gln Val Ile Arg Leu Tyr Asn Leu Pro Gly Val Glu
                    850                 855                 860
Gly Leu Ser Leu Asp Val Ser Phe Gln Val Asp Ile Arg Asp Tyr Val
865                 870                 875                 880
Asn Lys Glu Leu Ala Leu Arg Ile His Thr Asp Ile Asp Ser Gln Gly
                    885                 890                 895
Thr Phe Phe Thr Asp Leu Asn Gly Phe Gln Val Gln Pro Arg Lys Tyr
                    900                 905                 910
Leu Lys Lys Leu Pro Leu Gln Ala Asn Phe Tyr Pro Met Pro Val Met
                    915                 920                 925
Ala Tyr Ile Gln Asp Ser Gln Arg Arg Leu Thr Leu His Thr Ala Gln
930                 935                 940
Ala Leu Gly Val Ser Ser Leu Gly Asn Gly Gln Leu Glu Val Ile Leu
945                 950                 955                 960
Asp Arg Arg Leu Met Gln Asp Asn Arg Gly Leu Gly Gln Gly Leu
                    965                 970                 975
Lys Asp Asn Lys Ile Thr Cys Asn His Phe Arg Leu Leu Leu Glu Arg
                    980                 985                 990
Arg Thr Leu Met Ser Pro Glu Val  Gln Gln Glu Arg Ser  Thr Ser Tyr
                    995                 1000                1005
Pro Ser  Leu Leu Ser His Met  Thr Ser Met Tyr Leu  Asn Thr Pro
     1010                1015                1020
Pro Leu  Val Leu Pro Val Ala  Lys Arg Glu Ser Thr  Ser Pro Thr
     1025                1030                1035
Leu His  Ser Phe His Pro Leu  Ala Ser Pro Leu Pro  Cys Asp Phe
     1040                1045                1050
His Leu  Leu Asn Leu Arg Met  Leu Pro Ala Glu Val  Ser Val Pro
     1055                1060                1065
Val Arg  Ala Asn Pro His His  Gln Ala Glu Asp Thr  Leu Pro Ala
     1070                1075                1080
Ala Asp  Ala Ala Leu Ile Leu  His Arg Lys Gly Phe  Asp Cys Gly
     1085                1090                1095
Leu Glu  Ala Lys Asn Leu Gly  Phe Asn Cys Thr Thr  Ser Gln Gly
     1100                1105                1110
Lys Leu  Ala Leu Gly Ser Leu  Phe His Gly Leu Asp  Val Leu Phe
     1115                1120                1125
Leu Gln  Pro Thr Ser Leu Thr  Leu Leu Tyr Pro Leu  Ala Ser Pro
     1130                1135                1140
Ser Asn  Ser Thr Asp Ile Ser  Leu Glu Pro Met Glu  Ile Ser Thr
     1145                1150                1155
Phe Arg  Leu Arg Leu Gly
     1160
```

<210> SEQ ID NO 7
<211> LENGTH: 447
<212> TYPE: PRT
<213> ORGANISM: Homo sapiens

<400> SEQUENCE: 7

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Asn Glu Ala Leu Ala Pro Pro Leu Leu Asp Ala Glu Pro Ala Arg
        35                  40                  45

Gly Ala Gly Gly Arg Gly Gly Asp His Pro Ser Val Ala Val Gly Ile
    50                  55                  60

Arg Arg Val Ser Asn Val Ser Ala Ala Ser Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
            100                 105                 110

Trp Ala Pro Arg Glu Leu Val Leu Val Val Gln Val His Asn Arg Pro
        115                 120                 125

Glu Tyr Leu Arg Leu Leu Leu Asp Ser Leu Arg Lys Ala Gln Gly Ile
    130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Pro Lys Asn Ala Ala Leu Lys Leu
        195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Trp Lys Leu His Phe
225                 230                 235                 240

Val Trp Glu Arg Val Lys Ile Leu Arg Asp Tyr Ala Gly Leu Ile Leu
                245                 250                 255

Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
        275                 280                 285

Leu Ser Leu Gly Thr Tyr Ser Ala Ser Arg Ser Phe Tyr Gly Met Ala
    290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
        355                 360                 365

Ile Pro Arg Ile Phe His Ala Gly Asp Cys Gly Met His His Lys Lys

```
                    370                 375                 380
Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
                420                 425                 430

Asp Ile Arg Asp His Glu Leu Cys Lys Ser Tyr Arg Arg Leu Gln
                435                 440                 445

<210> SEQ ID NO 8
<211> LENGTH: 442
<212> TYPE: PRT
<213> ORGANISM: Rattus norvegicus

<400> SEQUENCE: 8

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
                20                  25                  30

Lys Asn Asp Ala Leu Ala Pro Pro Leu Leu Asp Ser Glu Pro Leu Arg
            35                  40                  45

Gly Ala Gly His Phe Ala Ala Ser Val Gly Ile Arg Arg Val Ser Asn
        50                  55                  60

Asp Ser Ala Ala Pro Leu Val Pro Ala Val Pro Arg Pro Glu Val Asp
65                  70                  75                  80

Asn Leu Thr Leu Arg Tyr Arg Ser Leu Val Tyr Gln Leu Asn Phe Asp
                85                  90                  95

Gln Met Leu Arg Asn Val Asp Lys Asp Gly Thr Trp Ser Pro Gly Glu
            100                 105                 110

Leu Val Leu Val Val Gln Val His Asn Arg Pro Glu Tyr Leu Arg Leu
        115                 120                 125

Leu Ile Asp Ser Leu Arg Lys Ala Gln Gly Ile Arg Glu Val Leu Val
    130                 135                 140

Ile Phe Ser His Asp Phe Trp Ser Ala Glu Ile Asn Ser Leu Ile Ser
145                 150                 155                 160

Ser Val Asp Phe Cys Pro Val Leu Gln Val Phe Phe Pro Phe Ser Ile
                165                 170                 175

Gln Leu Tyr Pro Ser Glu Phe Pro Gly Ser Asp Pro Arg Asp Cys Pro
            180                 185                 190

Arg Asp Leu Lys Lys Asn Ala Ala Leu Lys Leu Gly Cys Ile Asn Ala
        195                 200                 205

Glu Tyr Pro Asp Ser Phe Gly His Tyr Arg Glu Ala Lys Phe Ser Gln
    210                 215                 220

Thr Lys His His Trp Trp Trp Lys Leu His Phe Val Trp Glu Arg Val
225                 230                 235                 240

Lys Val Leu Gln Asp Tyr Thr Gly Leu Ile Leu Phe Leu Glu Glu Asp
                245                 250                 255

His Tyr Leu Ala Pro Asp Phe Tyr His Val Phe Lys Lys Met Trp Lys
            260                 265                 270

Leu Lys Gln Gln Glu Cys Pro Gly Cys Asp Val Leu Ser Leu Gly Thr
        275                 280                 285

Tyr Thr Thr Ile Arg Ser Phe Tyr Gly Ile Ala Asp Lys Val Asp Val
    290                 295                 300
```

```
Lys Thr Trp Lys Ser Thr Glu His Asn Met Gly Leu Ala Leu Thr Arg
305                 310                 315                 320

Asp Ala Tyr Gln Lys Leu Ile Glu Cys Thr Asp Thr Phe Cys Thr Tyr
                325                 330                 335

Asp Asp Tyr Asn Trp Asp Trp Thr Leu Gln Tyr Leu Thr Leu Ala Cys
            340                 345                 350

Leu Pro Lys Val Trp Lys Val Leu Val Pro Gln Ala Pro Arg Ile Phe
        355                 360                 365

His Ala Gly Asp Cys Gly Met His His Lys Lys Thr Cys Arg Pro Ser
370                 375                 380

Thr Gln Ser Ala Gln Ile Glu Ser Leu Leu Asn Asn Asn Lys Gln Tyr
385                 390                 395                 400

Leu Phe Pro Glu Thr Leu Val Ile Gly Glu Lys Phe Pro Met Ala Ala
                405                 410                 415

Ile Ser Pro Pro Arg Lys Asn Gly Gly Trp Gly Asp Ile Arg Asp His
            420                 425                 430

Glu Leu Cys Lys Ser Tyr Arg Arg Leu Gln
        435                 440

<210> SEQ ID NO 9
<211> LENGTH: 442
<212> TYPE: PRT
<213> ORGANISM: Mus musculus

<400> SEQUENCE: 9

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
                20                  25                  30

Lys Ser Asp Ala Leu Gly Pro Pro Leu Leu Asp Ala Glu Pro Val Arg
            35                  40                  45

Gly Ala Gly His Leu Ala Val Ser Val Gly Ile Arg Arg Val Ser Asn
        50                  55                  60

Glu Ser Ala Ala Pro Leu Val Pro Ala Val Pro Arg Pro Glu Val Asp
65                  70                  75                  80

Asn Leu Thr Leu Arg Tyr Arg Ser Leu Val Tyr Gln Leu Asn Phe Asp
                85                  90                  95

Gln Met Leu Arg Asn Val Gly Asn Asp Gly Thr Trp Ser Pro Gly Glu
            100                 105                 110

Leu Val Leu Val Val Gln Val His Asn Arg Pro Glu Tyr Leu Arg Leu
        115                 120                 125

Leu Ile Asp Ser Leu Arg Lys Ala Gln Gly Ile Gln Glu Val Leu Val
130                 135                 140

Ile Phe Ser His Asp Phe Trp Ser Ala Glu Ile Asn Ser Leu Ile Ser
145                 150                 155                 160

Arg Val Asp Phe Cys Pro Val Leu Gln Val Phe Phe Pro Phe Ser Ile
                165                 170                 175

Gln Leu Tyr Pro Asn Glu Phe Pro Gly Ser Asp Pro Arg Asp Cys Pro
            180                 185                 190

Arg Asp Leu Lys Lys Asn Ala Ala Leu Lys Leu Gly Cys Ile Asn Ala
        195                 200                 205

Glu Tyr Pro Asp Ser Phe Gly His Tyr Arg Glu Ala Lys Phe Ser Gln
210                 215                 220

Thr Lys His His Trp Trp Trp Lys Leu His Phe Val Trp Glu Arg Val
225                 230                 235                 240
```

Lys Val Leu Gln Asp Tyr Thr Gly Leu Ile Leu Phe Leu Glu Glu Asp
            245                 250                 255

His Tyr Leu Ala Pro Asp Phe Tyr His Val Phe Lys Lys Met Trp Lys
                260                 265                 270

Leu Lys Gln Gln Glu Cys Pro Gly Cys Asp Val Leu Ser Leu Gly Thr
                275                 280                 285

Tyr Thr Thr Ile Arg Ser Phe Tyr Gly Ile Ala Asp Lys Val Asp Val
            290                 295                 300

Lys Thr Trp Lys Ser Thr Glu His Asn Met Gly Leu Ala Leu Thr Arg
305                 310                 315                 320

Asp Ala Tyr Gln Lys Leu Ile Glu Cys Thr Asp Thr Phe Cys Thr Tyr
                325                 330                 335

Asp Asp Tyr Asn Trp Asp Trp Thr Leu Gln Tyr Leu Thr Leu Ala Cys
            340                 345                 350

Leu Pro Lys Ile Trp Lys Val Leu Val Pro Gln Ala Pro Arg Ile Phe
            355                 360                 365

His Ala Gly Asp Cys Gly Met His His Lys Lys Thr Cys Arg Pro Ser
        370                 375                 380

Thr Gln Ser Ala Gln Ile Glu Ser Leu Leu Asn Ser Asn Lys Gln Tyr
385                 390                 395                 400

Leu Phe Pro Glu Thr Leu Val Ile Gly Glu Lys Phe Pro Met Ala Ala
                405                 410                 415

Ile Ser Pro Pro Arg Lys Asn Gly Gly Trp Gly Asp Ile Arg Asp His
            420                 425                 430

Glu Leu Cys Lys Ser Tyr Arg Arg Leu Gln
        435                 440

<210> SEQ ID NO 10
<211> LENGTH: 442
<212> TYPE: PRT
<213> ORGANISM: Cricetulus griseus

<400> SEQUENCE: 10

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
                20                  25                  30

Lys Asn Asp Gly Leu Ala Pro Pro Leu Leu Asp Ala Glu Pro Pro Arg
            35                  40                  45

Gly Pro Gly His Leu Ala Val Ser Val Gly Ile Arg Arg Val Ser Asn
    50                  55                  60

Asp Ser Ala Pro Pro Val Val Pro Ala Ala Pro Arg Pro Glu Val Asp
65                  70                  75                  80

Asn Leu Thr Leu Arg Tyr Arg Ser Leu Val Tyr Gln Leu Asn Phe Asp
                85                  90                  95

Gln Met Leu Arg Asn Val Arg Asp Gly Thr Trp Arg Pro Gly Glu
            100                 105                 110

Leu Val Leu Val Val Gln Val His Asn Arg Pro Glu Tyr Leu Arg Leu
        115                 120                 125

Leu Leu Asp Ser Leu Arg Lys Ala Gln Gly Ile Asn Glu Val Leu Val
    130                 135                 140

Ile Phe Ser His Asp Phe Trp Ser Ala Glu Ile Asn His Met Ile Ala
145                 150                 155                 160

Ser Val Asn Phe Cys Pro Val Leu Gln Val Phe Phe Pro Phe Ser Ile

```
                        165                 170                 175
Gln Leu Tyr Pro Ser Glu Phe Pro Gly Ser Asp Pro Arg Asp Cys Pro
                180                 185                 190

Arg Asp Leu Lys Lys Asn Ala Ala Leu Lys Leu Gly Cys Ile Asn Ala
            195                 200                 205

Glu Tyr Pro Asp Ser Phe Gly His Tyr Arg Glu Ala Lys Phe Ser Gln
        210                 215                 220

Thr Lys His His Trp Trp Trp Lys Leu His Phe Val Trp Glu Arg Val
225                 230                 235                 240

Arg Val Leu Gln Asp Tyr Thr Gly Leu Ile Leu Phe Leu Glu Glu Asp
                245                 250                 255

His Tyr Leu Ala Pro Asp Phe Tyr His Val Phe Lys Lys Met Trp Lys
                260                 265                 270

Leu Lys Gln Gln Glu Cys Pro Gly Cys Asp Val Leu Ser Leu Gly Thr
            275                 280                 285

Tyr Thr Ala Ser Arg Ser Phe Tyr Gly Ile Ala Asp Lys Val Asp Val
        290                 295                 300

Lys Thr Trp Lys Ser Thr Glu His Asn Met Gly Leu Ala Leu Thr Arg
305                 310                 315                 320

Asp Ala Tyr Gln Lys Leu Ile Glu Cys Thr Asp Thr Phe Cys Thr Tyr
                325                 330                 335

Asp Asp Tyr Asn Trp Asp Trp Thr Leu Gln Tyr Leu Thr Val Ser Cys
                340                 345                 350

Leu Pro Lys Phe Trp Lys Val Leu Val Pro Gln Ala Pro Arg Ile Phe
            355                 360                 365

His Ala Gly Asp Cys Gly Met His His Lys Lys Thr Cys Arg Pro Ser
        370                 375                 380

Thr Gln Ser Ala Gln Ile Glu Ser Phe Leu Asn Asn Gln Gln Tyr
385                 390                 395                 400

Met Phe Pro Glu Thr Leu Val Ile Ser Glu Lys Phe Ser Met Ala Ala
                405                 410                 415

Ile Ser Pro Pro Arg Lys Asn Gly Gly Trp Gly Asp Ile Arg Asp His
                420                 425                 430

Glu Leu Cys Lys Ser Tyr Arg Arg Leu Gln
            435                 440

<210> SEQ ID NO 11
<211> LENGTH: 398
<212> TYPE: PRT
<213> ORGANISM: Homo sapiens

<400> SEQUENCE: 11

Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
                20                  25                  30

His Leu Gly Val Thr Leu Val Tyr Tyr Leu Ala Gly Arg Asp Leu Ser
            35                  40                  45

Arg Leu Pro Gln Leu Val Gly Val Ser Thr Pro Leu Gln Gly Gly Ser
        50                  55                  60

Asn Ser Ala Ala Ala Ile Gly Gln Ser Ser Gly Glu Leu Arg Thr Gly
65                  70                  75                  80

Gly Ala Arg Pro Pro Pro Pro Leu Gly Ala Ser Ser Gln Pro Arg Pro
                85                  90                  95
```

```
Gly Gly Asp Ser Ser Pro Val Val Asp Ser Gly Pro Gly Pro Ala Ser
            100                 105                 110

Asn Leu Thr Ser Val Pro Val Pro His Thr Thr Ala Leu Ser Leu Pro
        115                 120                 125

Ala Cys Pro Glu Glu Ser Pro Leu Leu Val Gly Pro Met Leu Ile Glu
    130                 135                 140

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
                165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
        195                 200                 205

Tyr Gly Ile Tyr Val Ile Asn Gln Ala Gly Asp Thr Ile Phe Asn Arg
    210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
            260                 265                 270

Met Asp Lys Phe Gly Phe Ser Leu Pro Tyr Val Gln Tyr Phe Gly Gly
        275                 280                 285

Val Ser Ala Leu Ser Lys Gln Gln Phe Leu Thr Ile Asn Gly Phe Pro
    290                 295                 300

Asn Asn Tyr Trp Gly Trp Gly Gly Glu Asp Asp Asp Ile Phe Asn Arg
305                 310                 315                 320

Leu Val Phe Arg Gly Met Ser Ile Ser Arg Pro Asn Ala Val Val Gly
                325                 330                 335

Arg Cys Arg Met Ile Arg His Ser Arg Asp Lys Lys Asn Glu Pro Asn
            340                 345                 350

Pro Gln Arg Phe Asp Arg Ile Ala His Thr Lys Glu Thr Met Leu Ser
        355                 360                 365

Asp Gly Leu Asn Ser Leu Thr Tyr Gln Val Leu Asp Val Gln Arg Tyr
    370                 375                 380

Pro Leu Tyr Thr Gln Ile Thr Val Asp Ile Gly Thr Pro Ser
385                 390                 395

<210> SEQ ID NO 12
<211> LENGTH: 399
<212> TYPE: PRT
<213> ORGANISM: Rattus norvegicus

<400> SEQUENCE: 12

Met Arg Phe Arg Glu Pro Phe Leu Gly Gly Ser Ala Ala Met Pro Gly
1               5                   10                  15

Ala Thr Leu Gln Arg Ala Cys Arg Leu Leu Val Ala Val Cys Ala Leu
            20                  25                  30

His Leu Gly Val Thr Leu Val Tyr Tyr Leu Ser Gly Arg Asp Leu Ser
        35                  40                  45

Arg Leu Pro Gln Leu Val Gly Val Ser Ser Leu Gln Gly Gly Thr
    50                  55                  60

Asn Gly Ala Ala Ala Ser Lys Gln Pro Ser Gly Glu Leu Arg Pro Arg
65                  70                  75                  80
```

```
Gly Ala Arg Pro Pro Pro Leu Gly Val Ser Pro Lys Pro Arg Pro
            85                  90                  95

Gly Ser Asp Ser Ser Pro Asp Ala Ala Ser Gly Pro Gly Leu Lys Ser
                100                 105                 110

Asn Leu Thr Ser Val Pro Met Pro Thr Ser Thr Gly Leu Leu Thr Leu
            115                 120                 125

Pro Ala Cys Pro Glu Glu Ser Pro Leu Leu Val Gly Pro Met Val Ile
130                 135                 140

Asp Phe Asn Ile Pro Val Asp Leu Glu Leu Leu Ala Lys Lys Asn Pro
145                 150                 155                 160

Glu Ile Lys Met Gly Gly Arg Tyr Phe Pro Lys Asp Cys Ile Ser Pro
                165                 170                 175

His Lys Val Ala Ile Ile Ile Pro Phe Arg Asn Arg Gln Glu His Leu
            180                 185                 190

Lys Tyr Trp Leu Tyr Tyr Leu His Pro Val Leu Gln Arg Gln Gln Leu
        195                 200                 205

Asp Tyr Gly Ile Tyr Val Ile Asn Gln Ala Gly Asp Thr Met Phe Asn
    210                 215                 220

Arg Ala Lys Leu Leu Asn Val Gly Phe Gln Glu Ala Leu Lys Asp Tyr
225                 230                 235                 240

Asp Tyr Asn Cys Phe Val Phe Ser Asp Val Asp Leu Ile Pro Met Asp
                245                 250                 255

Asp His Asn Ala Tyr Arg Cys Phe Ser Gln Pro Arg His Ile Ser Val
            260                 265                 270

Ala Met Asp Lys Phe Gly Phe Ser Leu Pro Tyr Val Gln Tyr Phe Gly
        275                 280                 285

Gly Val Ser Ala Leu Ser Lys Gln Gln Phe Leu Thr Ile Asn Gly Phe
    290                 295                 300

Pro Asn Asn Tyr Trp Gly Trp Gly Gly Glu Asp Asp Asp Ile Phe Asn
305                 310                 315                 320

Arg Leu Val His Lys Gly Met Ser Ile Ser Arg Pro Asn Ala Val Val
                325                 330                 335

Gly Arg Cys Arg Met Ile Arg His Ser Arg Asp Lys Lys Asn Glu Pro
            340                 345                 350

Asn Pro Gln Arg Phe Asp Arg Ile Ala His Thr Lys Glu Thr Met Arg
        355                 360                 365

Leu Asp Gly Leu Asn Ser Leu Thr Tyr Gln Val Leu Asp Ile Gln Arg
    370                 375                 380

Tyr Pro Leu Tyr Thr Lys Ile Thr Val Asp Ile Gly Thr Pro Arg
385                 390                 395

<210> SEQ ID NO 13
<211> LENGTH: 399
<212> TYPE: PRT
<213> ORGANISM: Mus musculus

<400> SEQUENCE: 13

Met Arg Phe Arg Glu Gln Phe Leu Gly Gly Ser Ala Ala Met Pro Gly
1               5                   10                  15

Ala Thr Leu Gln Arg Ala Cys Arg Leu Leu Val Ala Val Cys Ala Leu
            20                  25                  30

His Leu Gly Val Thr Leu Val Tyr Tyr Leu Ser Gly Arg Asp Leu Ser
        35                  40                  45

Arg Leu Pro Gln Leu Val Gly Val Ser Ser Thr Leu Gln Gly Gly Thr
```

Asn Gly Ala Ala Ala Ser Lys Gln Pro Pro Gly Glu Gln Arg Pro Arg
65                  70                  75                  80

Gly Ala Arg Pro Pro Pro Leu Gly Val Ser Pro Lys Pro Arg Pro
            85                  90                  95

Gly Leu Asp Ser Ser Pro Gly Ala Ala Ser Gly Pro Gly Leu Lys Ser
            100                 105                 110

Asn Leu Ser Ser Leu Pro Val Pro Thr Thr Thr Gly Leu Leu Ser Leu
            115                 120                 125

Pro Ala Cys Pro Glu Glu Ser Pro Leu Leu Val Gly Pro Met Leu Ile
130                 135                 140

Asp Phe Asn Ile Ala Val Asp Leu Glu Leu Leu Ala Lys Lys Asn Pro
145                 150                 155                 160

Glu Ile Lys Thr Gly Gly Arg Tyr Ser Pro Lys Asp Cys Val Ser Pro
            165                 170                 175

His Lys Val Ala Ile Ile Pro Phe Arg Asn Arg Gln Glu His Leu
            180                 185                 190

Lys Tyr Trp Leu Tyr Tyr Leu His Pro Ile Leu Gln Arg Gln Gln Leu
            195                 200                 205

Asp Tyr Gly Ile Tyr Val Ile Asn Gln Ala Gly Asp Thr Met Phe Asn
210                 215                 220

Arg Ala Lys Leu Leu Asn Ile Gly Phe Gln Glu Ala Leu Lys Asp Tyr
225                 230                 235                 240

Asp Tyr Asn Cys Phe Val Phe Ser Asp Val Asp Leu Ile Pro Met Asp
            245                 250                 255

Asp Arg Asn Ala Tyr Arg Cys Phe Ser Gln Pro Arg His Ile Ser Val
            260                 265                 270

Ala Met Asp Lys Phe Gly Phe Ser Leu Pro Tyr Val Gln Tyr Phe Gly
            275                 280                 285

Gly Val Ser Ala Leu Ser Lys Gln Gln Phe Leu Ala Ile Asn Gly Phe
290                 295                 300

Pro Asn Asn Tyr Trp Gly Trp Gly Gly Glu Asp Asp Asp Ile Phe Asn
305                 310                 315                 320

Arg Leu Val His Lys Gly Met Ser Ile Ser Arg Pro Asn Ala Val Val
            325                 330                 335

Gly Arg Cys Arg Met Ile Arg His Ser Arg Asp Lys Lys Asn Glu Pro
            340                 345                 350

Asn Pro Gln Arg Phe Asp Arg Ile Ala His Thr Lys Glu Thr Met Arg
            355                 360                 365

Phe Asp Gly Leu Asn Ser Leu Thr Tyr Lys Val Leu Asp Val Gln Arg
370                 375                 380

Tyr Pro Leu Tyr Thr Gln Ile Thr Val Asp Ile Gly Thr Pro Arg
385                 390                 395

<210> SEQ ID NO 14
<211> LENGTH: 393
<212> TYPE: PRT
<213> ORGANISM: Cricetulus griseus

<400> SEQUENCE: 14

Met Arg Phe Leu Arg Pro Val Leu Gly Gly Ser Ala Ala Met Pro Gly
1               5                   10                  15

Ala Thr Leu Gln Arg Ala Cys Arg Leu Leu Val Ala Val Cys Ala Leu
            20                  25                  30

His Leu Gly Val Thr Leu Val Tyr Leu Ser Gly Arg Asp Leu Ser
        35                  40                  45

Arg Leu Pro Gln Leu Val Gly Val Ser Ser Thr Leu Arg Ser Gly Thr
 50                  55                  60

Ile Gly Ala Thr Ala Asn Lys Gln Pro Pro Gly Ala Arg Pro Pro Pro
 65                  70                  75                  80

Pro Val Gly Val Ser Ser Lys Pro Arg Pro Gly Pro Asp Ser Ser Pro
                 85                  90                  95

Gly Thr Ala Phe Asp Pro Gly Leu Lys Ser Asn Trp Thr Ser Val Leu
                100                 105                 110

Val Pro Pro Thr Thr Ala Leu Leu Thr Leu Pro Ala Cys Pro Glu Glu
            115                 120                 125

Ser Pro Leu Leu Val Gly Pro Met Val Ile Asp Phe Asn Ile Ala Val
        130                 135                 140

Asp Leu Glu Leu Leu Ala Lys Lys Asn Pro Glu Ile Lys Met Gly Gly
145                 150                 155                 160

Arg Tyr Ser Pro Lys Asp Cys Ile Ser Pro His Lys Val Ala Ile Ile
                165                 170                 175

Ile Pro Phe Arg Asn Arg Gln Glu His Leu Lys Tyr Trp Leu Tyr Tyr
                180                 185                 190

Leu His Pro Val Leu Gln Arg Gln Gln Leu Asp Tyr Gly Ile Tyr Val
            195                 200                 205

Ile Asn Gln Ala Gly Asp Thr Met Phe Asn Arg Ala Lys Leu Leu Asn
        210                 215                 220

Ile Gly Phe Gln Glu Ala Leu Lys Asp His Asp Tyr Asn Cys Phe Val
225                 230                 235                 240

Phe Ser Asp Val Asp Leu Ile Pro Met Asp Asp His Asn Ala Tyr Arg
                245                 250                 255

Cys Phe Ser Gln Pro Arg His Ile Ser Val Ala Met Asp Lys Phe Gly
                260                 265                 270

Phe Ser Leu Pro Tyr Val Gln Tyr Phe Gly Gly Val Ser Ala Leu Ser
            275                 280                 285

Lys Gln Gln Phe Leu Ala Ile Asn Gly Phe Pro Asn Asn Tyr Trp Gly
290                 295                 300

Trp Gly Gly Glu Asp Asp Asp Ile Phe Asn Arg Ile Val His Lys Gly
305                 310                 315                 320

Met Ser Ile Ser Arg Pro Asn Ala Val Val Gly Arg Cys Arg Met Ile
                325                 330                 335

Arg His Ser Arg Asp Lys Lys Asn Glu Pro Asn Pro Gln Arg Phe Asp
                340                 345                 350

Arg Ile Ala His Thr Lys Glu Thr Met Arg Phe Asp Gly Leu Asn Ser
            355                 360                 365

Leu Thr Tyr Gln Val Leu Asn Val Glu Arg Tyr Pro Leu Tyr Thr Lys
        370                 375                 380

Ile Thr Val Asp Ile Gly Thr Pro Arg
385                 390

<210> SEQ ID NO 15
<211> LENGTH: 403
<212> TYPE: PRT
<213> ORGANISM: Rattus norvegicus

<400> SEQUENCE: 15

Met Ile His Thr Asn Leu Lys Lys Lys Phe Ser Leu Phe Ile Leu Val
 1               5                  10                  15

Phe Leu Leu Phe Ala Val Ile Cys Val Trp Lys Lys Gly Ser Asp Tyr
            20                  25                  30

Glu Ala Leu Thr Leu Gln Ala Lys Glu Phe Gln Met Pro Lys Ser Gln
        35                  40                  45

Glu Lys Val Ala Met Gly Ser Ala Ser Gln Val Val Phe Ser Asn Ser
 50                  55                  60

Lys Gln Asp Pro Lys Glu Asp Ile Pro Ile Leu Ser Tyr His Arg Val
 65                  70                  75                  80

Thr Ala Lys Val Lys Pro Gln Pro Ser Phe Gln Val Trp Asp Lys Asp
                85                  90                  95

Ser Thr Tyr Ser Lys Leu Asn Pro Arg Leu Leu Lys Ile Trp Arg Asn
            100                 105                 110

Tyr Leu Asn Met Asn Lys Tyr Lys Val Ser Tyr Lys Gly Pro Gly Pro
        115                 120                 125

Gly Val Lys Phe Ser Val Glu Ala Leu Arg Cys His Leu Arg Asp His
130                 135                 140

Val Asn Val Ser Met Ile Glu Ala Thr Asp Phe Pro Phe Asn Thr Thr
145                 150                 155                 160

Glu Trp Glu Gly Tyr Leu Pro Lys Glu Asn Phe Arg Thr Lys Val Gly
                165                 170                 175

Pro Trp Gln Arg Cys Ala Val Val Ser Ser Ala Gly Ser Leu Lys Asn
            180                 185                 190

Ser Gln Leu Gly Arg Glu Ile Asp Asn His Asp Ala Val Leu Arg Phe
        195                 200                 205

Asn Gly Ala Pro Thr Asp Asn Phe Gln Gln Asp Val Gly Ser Lys Thr
210                 215                 220

Thr Ile Arg Leu Met Asn Ser Gln Leu Val Thr Thr Glu Lys Arg Phe
225                 230                 235                 240

Leu Lys Asp Ser Leu Tyr Thr Glu Gly Ile Leu Ile Val Trp Asp Pro
                245                 250                 255

Ser Val Tyr His Ala Asp Ile Pro Lys Trp Tyr Gln Lys Pro Asp Tyr
            260                 265                 270

Asn Phe Phe Glu Thr Tyr Lys Ser Tyr Arg Arg Leu Asn Pro Ser Gln
        275                 280                 285

Pro Phe Tyr Ile Leu Lys Pro Gln Met Pro Trp Glu Leu Trp Asp Ile
290                 295                 300

Ile Gln Glu Ile Ser Ala Asp Leu Ile Gln Pro Asn Pro Pro Ser Ser
305                 310                 315                 320

Gly Met Leu Gly Ile Ile Met Met Thr Leu Cys Asp Gln Val Asp
                325                 330                 335

Ile Tyr Glu Phe Leu Pro Ser Lys Arg Lys Thr Asp Val Cys Tyr Tyr
            340                 345                 350

His Gln Lys Phe Phe Asp Ser Ala Cys Thr Met Gly Ala Tyr Asp Pro
        355                 360                 365

Leu Leu Phe Glu Lys Asn Met Val Lys His Leu Asn Glu Gly Thr Asp
370                 375                 380

Glu Asp Ile Tyr Leu Phe Gly Lys Ala Thr Leu Ser Gly Phe Arg Asn
385                 390                 395                 400

Ile Arg Cys

<210> SEQ ID NO 16
<211> LENGTH: 525
<212> TYPE: PRT

<213> ORGANISM: Rattus norvegicus

<400> SEQUENCE: 16

```
Met Lys Pro His Leu Lys Gln Trp Arg Gln Arg Met Leu Phe Ala Ile
1               5                   10                  15
Phe Val Trp Gly Leu Leu Phe Leu Ala Ile Phe Ile Tyr Phe Thr Asn
            20                  25                  30
Ser Asn Pro Ala Ala Pro Met Pro Ser Ser Phe Ser Phe Leu Glu Ser
        35                  40                  45
Arg Gly Leu Leu Pro Val Gln Gly Lys Gln Arg Val Ile Met Gly Ala
    50                  55                  60
Leu Gln Glu Pro Ser Leu Pro Arg Ser Leu Glu Pro Ser Lys Val Leu
65                  70                  75                  80
Met Asp Gly His Ser Ala Ser Pro Phe Asn Ser Trp Pro Gly Asp Pro
                85                  90                  95
Gln Lys Gly Asp Gln Ala Gln Asp Gly Phe Asp Asn Gly Asp Glu Phe
            100                 105                 110
Phe Thr Ser Gln Val Gly Arg Lys Ser Gln Ser Ala Phe Tyr Pro Glu
        115                 120                 125
Glu Asp Asn Tyr Phe Phe Val Ala Gly Gln Pro Gly Leu Tyr His His
    130                 135                 140
Arg Gln Gly Ala Leu Gly Leu Pro Ser Pro Gly Glu Ser Ser Trp Gln
145                 150                 155                 160
Ser Gly Pro Gly Gln Pro Lys Gln Glu Lys Leu Arg His Pro Arg Arg
                165                 170                 175
Gly Ser Leu Pro Glu Glu Ala Tyr Asp Ser Asp Met Leu Ser Thr Ser
            180                 185                 190
Met Ser Arg Ala Phe Leu Tyr Arg Leu Trp Lys Gly Thr Val Ser Ser
        195                 200                 205
Lys Met Leu Asn Pro Arg Leu Gln Lys Ala Met Arg Tyr Tyr Met Ser
    210                 215                 220
Phe Asn Lys His Gly Val Arg Phe Ser Arg Arg Gly Arg Arg Glu Ala
225                 230                 235                 240
Arg Arg Thr Gly Pro Glu Leu Leu Cys Glu Met Arg Lys Arg Val Arg
                245                 250                 255
Val Arg Thr Leu Asp Gly Lys Glu Ala Pro Phe Ser Gly Leu Gly Trp
            260                 265                 270
Arg Pro Leu Val Pro Gly Val Pro Leu Ser Gln Leu His Pro Arg Gly
        275                 280                 285
Leu Arg Ser Cys Ala Val Val Met Ser Ala Gly Ala Ile Leu Asn Ser
    290                 295                 300
Ser Leu Gly Glu Glu Ile Asp Ser His Asp Ala Val Leu Arg Phe Asn
305                 310                 315                 320
Ser Ala Pro Thr Arg Gly Tyr Glu Lys Asp Val Gly Asn Lys Thr Thr
                325                 330                 335
Val Arg Ile Ile Asn Ser Gln Ile Leu Ala Asn Pro Ser His His Phe
            340                 345                 350
Ile Asp Ser Ser Leu Tyr Lys Asp Val Ile Leu Val Ala Trp Asp Pro
        355                 360                 365
Ala Pro Tyr Ser Ala Asn Leu Asn Leu Trp Tyr Lys Lys Pro Asp Tyr
    370                 375                 380
Asn Leu Phe Thr Pro Tyr Ile Gln His Arg Leu Lys Tyr Pro Thr Gln
385                 390                 395                 400
```

```
Pro Phe Tyr Ile Leu His Pro Lys Phe Ile Trp Gln Leu Trp Asp Ile
                405                 410                 415

Ile Gln Glu Asn Thr Arg Glu Lys Ile Gln Pro Asn Pro Pro Ser Ser
            420                 425                 430

Gly Phe Ile Gly Ile Leu Val Met Met Ser Met Cys Gln Glu Val His
        435                 440                 445

Val Tyr Glu Tyr Ile Pro Ser Val Arg Gln Thr Glu Leu Cys His Tyr
    450                 455                 460

His Glu Leu Tyr Tyr Asp Ala Ala Cys Thr Leu Gly Ala Tyr His Pro
465                 470                 475                 480

Leu Leu Tyr Glu Lys Leu Leu Val Gln Arg Leu Asn Thr Gly Thr Gln
                485                 490                 495

Ala Asp Leu His His Lys Gly Lys Val Val Leu Pro Gly Phe Gln Thr
            500                 505                 510

Leu Arg Cys Pro Val Thr Arg Pro Asn Asn Thr Asn Thr
        515                 520                 525

<210> SEQ ID NO 17
<211> LENGTH: 406
<212> TYPE: PRT
<213> ORGANISM: Homo sapiens

<400> SEQUENCE: 17

Met Ile His Thr Asn Leu Lys Lys Lys Phe Ser Cys Cys Val Leu Val
1               5                   10                  15

Phe Leu Leu Phe Ala Val Ile Cys Val Trp Lys Glu Lys Lys Lys Gly
            20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Lys Asn Leu Ile Pro Arg Leu Gln Lys Ile
            100                 105                 110

Trp Lys Asn Tyr Leu Ser Met Asn Lys Tyr Lys Val Ser Tyr Lys Gly
        115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
            180                 185                 190

Leu Lys Ser Ser Gln Leu Gly Arg Glu Ile Asp Asp His Asp Ala Val
        195                 200                 205

Leu Arg Phe Asn Gly Ala Pro Thr Ala Asn Phe Gln Gln Asp Val Gly
    210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255
```

Trp Asp Pro Ser Val Tyr His Ser Asp Ile Pro Lys Trp Tyr Gln Asn
                260                 265                 270

Pro Asp Tyr Asn Phe Phe Asn Asn Tyr Lys Thr Tyr Arg Lys Leu His
            275                 280                 285

Pro Asn Gln Pro Phe Tyr Ile Leu Lys Pro Gln Met Pro Trp Glu Leu
        290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
                340                 345                 350

Cys Tyr Tyr Tyr Gln Lys Phe Phe Asp Ser Ala Cys Thr Met Gly Ala
            355                 360                 365

Tyr His Pro Leu Leu Tyr Glu Lys Asn Leu Val Lys His Leu Asn Gln
        370                 375                 380

Gly Thr Asp Glu Asp Ile Tyr Leu Leu Gly Lys Ala Thr Leu Pro Gly
385                 390                 395                 400

Phe Arg Thr Ile His Cys
                405

<210> SEQ ID NO 18
<211> LENGTH: 529
<212> TYPE: PRT
<213> ORGANISM: Homo sapiens

<400> SEQUENCE: 18

Met Lys Pro His Leu Lys Gln Trp Arg Gln Arg Met Leu Phe Gly Ile
1               5                   10                  15

Phe Ala Trp Gly Leu Leu Phe Leu Leu Ile Phe Ile Tyr Phe Thr Asp
                20                  25                  30

Ser Asn Pro Ala Glu Pro Val Pro Ser Ser Leu Ser Phe Leu Glu Thr
            35                  40                  45

Arg Arg Leu Leu Pro Val Gln Gly Lys Gln Arg Ala Ile Met Gly Ala
        50                  55                  60

Ala His Glu Pro Ser Pro Gly Gly Leu Asp Ala Arg Gln Ala Leu
65                  70                  75                  80

Pro Arg Ala His Pro Ala Gly Ser Phe His Ala Gly Pro Gly Asp Leu
                85                  90                  95

Gln Lys Trp Ala Gln Ser Gln Asp Gly Phe Glu His Lys Glu Phe Phe
            100                 105                 110

Ser Ser Gln Val Gly Arg Lys Ser Gln Ser Ala Phe Tyr Pro Glu Asp
        115                 120                 125

Asp Asp Tyr Phe Phe Ala Ala Gly Gln Pro Gly Trp His Ser His Thr
    130                 135                 140

Gln Gly Thr Leu Gly Phe Pro Ser Pro Gly Pro Gly Pro Arg Glu
145                 150                 155                 160

Gly Ala Phe Pro Ala Ala Gln Val Gln Arg Arg Val Lys Arg
                165                 170                 175

His Arg Arg Gln Arg Arg Ser His Val Leu Glu Glu Gly Asp Asp Gly
            180                 185                 190

Asp Arg Leu Tyr Ser Ser Met Ser Arg Ala Phe Leu Tyr Arg Leu Trp
        195                 200                 205

Lys Gly Asn Val Ser Ser Lys Met Leu Asn Pro Arg Leu Gln Lys Ala

```
                    210                 215                 220
Met Lys Asp Tyr Leu Thr Ala Asn Lys His Gly Val Arg Phe Arg Gly
225                 230                 235                 240

Lys Arg Glu Ala Gly Leu Ser Arg Ala Gln Leu Leu Cys Gln Leu Arg
                245                 250                 255

Ser Arg Ala Arg Val Arg Thr Leu Asp Gly Thr Glu Ala Pro Phe Ser
            260                 265                 270

Ala Leu Gly Trp Arg Arg Leu Val Pro Ala Val Pro Leu Ser Gln Leu
        275                 280                 285

His Pro Arg Gly Leu Arg Ser Cys Ala Val Val Met Ser Ala Gly Ala
    290                 295                 300

Ile Leu Asn Ser Ser Leu Gly Glu Glu Ile Asp Ser His Asp Ala Val
305                 310                 315                 320

Leu Arg Phe Asn Ser Ala Pro Thr Arg Gly Tyr Glu Lys Asp Val Gly
                325                 330                 335

Asn Lys Thr Thr Ile Arg Ile Ile Asn Ser Gln Ile Leu Thr Asn Pro
            340                 345                 350

Ser His His Phe Ile Asp Ser Ser Leu Tyr Lys Asp Val Ile Leu Val
        355                 360                 365

Ala Trp Asp Pro Ala Pro Tyr Ser Ala Asn Leu Asn Leu Trp Tyr Lys
370                 375                 380

Lys Pro Asp Tyr Asn Leu Phe Thr Pro Tyr Ile Gln His Arg Gln Arg
385                 390                 395                 400

Asn Pro Asn Gln Pro Phe Tyr Ile Leu His Pro Lys Phe Ile Trp Gln
                405                 410                 415

Leu Trp Asp Ile Ile Gln Glu Asn Thr Lys Glu Lys Ile Gln Pro Asn
            420                 425                 430

Pro Pro Ser Ser Gly Phe Ile Gly Ile Leu Ile Met Met Ser Met Cys
        435                 440                 445

Arg Glu Val His Val Tyr Glu Tyr Ile Pro Ser Val Arg Gln Thr Glu
    450                 455                 460

Leu Cys His Tyr His Glu Leu Tyr Tyr Asp Ala Ala Cys Thr Leu Gly
465                 470                 475                 480

Ala Tyr His Pro Leu Leu Tyr Glu Lys Leu Leu Val Gln Arg Leu Asn
                485                 490                 495

Met Gly Thr Gln Gly Asp Leu His Arg Lys Gly Lys Val Val Leu Pro
            500                 505                 510

Gly Phe Gln Ala Val His Cys Pro Ala Pro Ser Pro Val Ile Pro His
        515                 520                 525

Ser

<210> SEQ ID NO 19
<211> LENGTH: 403
<212> TYPE: PRT
<213> ORGANISM: Mus musculus

<400> SEQUENCE: 19

Met Ile His Thr Asn Leu Lys Arg Lys Phe Ser Cys Phe Val Leu Val
1               5                   10                  15

Phe Leu Leu Phe Ala Ile Ile Cys Val Trp Lys Lys Gly Ser Asp Tyr
                20                  25                  30

Glu Ala Leu Thr Leu Gln Ala Lys Val Phe Gln Met Pro Lys Ser Gln
            35                  40                  45

Glu Lys Val Ala Val Gly Pro Ala Pro Gln Ala Val Phe Ser Asn Ser
```

Lys Gln Asp Pro Lys Glu Gly Val Gln Ile Leu Ser Tyr Pro Arg Val
65                  70                  75                  80

Thr Ala Lys Val Lys Pro Gln Pro Ser Leu Gln Val Trp Asp Lys Asp
                85                  90                  95

Ser Thr Tyr Ser Lys Leu Asn Pro Arg Leu Leu Lys Ile Trp Arg Asn
            100                 105                 110

Tyr Leu Asn Met Asn Lys Tyr Lys Val Ser Tyr Lys Gly Pro Gly Pro
            115                 120                 125

Gly Val Lys Phe Ser Val Glu Ala Leu Arg Cys His Leu Arg Asp His
        130                 135                 140

Val Asn Val Ser Met Ile Glu Ala Thr Asp Phe Pro Phe Asn Thr Thr
145                 150                 155                 160

Glu Trp Glu Gly Tyr Leu Pro Lys Glu Asn Phe Arg Thr Lys Ala Gly
                165                 170                 175

Pro Trp His Lys Cys Ala Val Val Ser Ser Ala Gly Ser Leu Lys Asn
            180                 185                 190

Ser Gln Leu Gly Arg Glu Ile Asp Asn His Asp Ala Val Leu Arg Phe
            195                 200                 205

Asn Gly Ala Pro Thr Asp Asn Phe Gln Gln Asp Val Gly Thr Lys Thr
210                 215                 220

Thr Ile Arg Leu Val Asn Ser Gln Leu Val Thr Thr Glu Lys Arg Phe
225                 230                 235                 240

Leu Lys Asp Ser Leu Tyr Thr Glu Gly Ile Leu Ile Leu Trp Asp Pro
                245                 250                 255

Ser Val Tyr His Ala Asp Ile Pro Gln Trp Tyr Gln Lys Pro Asp Tyr
            260                 265                 270

Asn Phe Phe Glu Thr Tyr Lys Ser Tyr Arg Arg Leu His Pro Ser Gln
            275                 280                 285

Pro Phe Tyr Ile Leu Lys Pro Gln Met Pro Trp Glu Leu Trp Asp Ile
        290                 295                 300

Ile Gln Glu Ile Ser Pro Asp Leu Ile Gln Pro Asn Pro Pro Ser Ser
305                 310                 315                 320

Gly Met Leu Gly Ile Ile Met Met Thr Leu Cys Asp Gln Val Asp
                325                 330                 335

Ile Tyr Glu Phe Leu Pro Ser Lys Arg Lys Thr Asp Val Cys Tyr Tyr
            340                 345                 350

His Gln Lys Phe Phe Asp Ser Ala Cys Thr Met Gly Ala Tyr His Pro
            355                 360                 365

Leu Leu Phe Glu Lys Asn Met Val Lys His Leu Asn Glu Gly Thr Asp
        370                 375                 380

Glu Asp Ile Tyr Leu Phe Gly Lys Ala Thr Leu Ser Gly Phe Arg Asn
385                 390                 395                 400

Asn Arg Cys

<210> SEQ ID NO 20
<211> LENGTH: 524
<212> TYPE: PRT
<213> ORGANISM: Mus musculus

<400> SEQUENCE: 20

Met Lys Pro His Leu Lys Gln Trp Arg Gln Arg Met Leu Phe Gly Ile
1               5                   10                  15

Phe Val Trp Gly Leu Leu Phe Leu Ala Ile Phe Ile Tyr Phe Thr Asn

```
                    20                  25                  30
Ser Asn Pro Ala Ala Pro Met Pro Ser Ser Phe Ser Phe Leu Glu Arg
                35                  40                  45

Arg Gly Leu Leu Pro Leu Gln Gly Lys Gln Arg Val Ile Met Gly Ala
        50                  55                  60

Leu Gln Glu Pro Ser Leu Pro Arg Ser Leu Asp Ala Ser Lys Val Leu
65                  70                  75                  80

Leu Asp Ser His Pro Glu Asn Pro Phe His Pro Trp Pro Gly Asp Pro
                85                  90                  95

Gln Lys Trp Asp Gln Ala Pro Asn Gly Phe Asp Asn Gly Asp Glu Phe
            100                 105                 110

Phe Thr Ser Gln Val Gly Arg Lys Ser Gln Ser Ala Phe Tyr Pro Glu
        115                 120                 125

Glu Asp Ser Tyr Phe Phe Val Ala Asp Gln Pro Glu Leu Tyr His His
    130                 135                 140

Arg Gln Gly Ala Leu Glu Leu Pro Ser Pro Gly Glu Thr Ser Trp Arg
145                 150                 155                 160

Ser Gly Pro Val Gln Pro Lys Gln Lys Leu Leu His Pro Arg Arg Gly
                165                 170                 175

Ser Leu Pro Glu Glu Ala Tyr Asp Ser Asp Met Leu Ser Ala Ser Met
            180                 185                 190

Ser Arg Ala Phe Leu Tyr Arg Leu Trp Lys Gly Ala Val Ser Ser Lys
        195                 200                 205

Met Leu Asn Pro Arg Leu Gln Lys Ala Met Arg Tyr Tyr Met Ser Phe
    210                 215                 220

Asn Lys His Gly Val Arg Phe Arg Arg Gly Arg Arg Glu Ala Thr
225                 230                 235                 240

Arg Thr Gly Pro Glu Leu Leu Cys Glu Met Arg Arg Val Arg Val
                245                 250                 255

Arg Thr Leu Asp Gly Arg Glu Ala Pro Phe Ser Gly Leu Gly Trp Arg
            260                 265                 270

Pro Leu Val Pro Gly Val Pro Leu Ser Gln Leu His Pro Arg Gly Leu
        275                 280                 285

Ser Ser Cys Ala Val Val Met Ser Ala Gly Ala Ile Leu Asn Ser Ser
    290                 295                 300

Leu Gly Glu Glu Ile Asp Ser His Asp Ala Val Leu Arg Phe Asn Ser
305                 310                 315                 320

Ala Pro Thr Arg Gly Tyr Glu Lys Asp Val Gly Asn Lys Thr Thr Val
                325                 330                 335

Arg Ile Ile Asn Ser Gln Ile Leu Ala Asn Pro Ser His His Phe Ile
            340                 345                 350

Asp Ser Ala Leu Tyr Lys Asp Val Ile Leu Val Ala Trp Asp Pro Ala
        355                 360                 365

Pro Tyr Ser Ala Asn Leu Asn Leu Trp Tyr Lys Lys Pro Asp Tyr Asn
    370                 375                 380

Leu Phe Thr Pro Tyr Ile Gln His Arg Arg Lys Tyr Pro Thr Gln Pro
385                 390                 395                 400

Phe Tyr Ile Leu His Pro Lys Phe Ile Trp Gln Leu Trp Asp Ile Ile
                405                 410                 415

Gln Glu Asn Thr Arg Glu Lys Ile Gln Pro Asn Pro Pro Ser Ser Gly
            420                 425                 430

Phe Ile Gly Ile Leu Ile Met Met Ser Met Cys Lys Glu Val His Val
        435                 440                 445
```

Tyr Glu Tyr Ile Pro Ser Val Arg Gln Thr Glu Leu Cys His Tyr His
450 455 460

Glu Leu Tyr Tyr Asp Ala Ala Cys Thr Leu Gly Ala Tyr His Pro Leu
465 470 475 480

Leu Tyr Glu Lys Leu Leu Val Gln Arg Leu Asn Thr Gly Thr Gln Ala
485 490 495

Asp Leu His His Lys Gly Lys Val Val Leu Pro Gly Phe Gln Thr Leu
500 505 510

Arg Cys Pro Val Thr Ser Pro Asn Asn Thr His Ser
515 520

<210> SEQ ID NO 21
<211> LENGTH: 402
<212> TYPE: PRT
<213> ORGANISM: Cricetulus griseus

<400> SEQUENCE: 21

Met Ile His Thr Asn Leu Lys Lys Lys Phe Ser Tyr Phe Ile Leu Ala
1 5 10 15

Phe Leu Leu Phe Ala Leu Ile Cys Val Trp Lys Lys Gly Ser Tyr Glu
20 25 30

Ala Leu Lys Leu Gln Ala Lys Glu Phe Gln Val Thr Arg Ser Leu Glu
35 40 45

Lys Leu Ala Met Arg Ser Gly Ser Gln Ser Met Ser Ser Ser Ser Lys
50 55 60

Gln Asp Pro Lys Gln Asp Ser Gln Val Leu Ser His Ala Arg Val Thr
65 70 75 80

Ala Lys Val Lys Pro Gln Pro Ser Tyr Gln Val Trp Asp Lys Asn Ser
85 90 95

Ser Ser Lys Asn Leu Asn Pro Arg Leu Gln Lys Ile Leu Lys Asn Tyr
100 105 110

Leu Asn Met Asn Lys Tyr Lys Val Ser Tyr Lys Gly Pro Gly Pro Gly
115 120 125

Val Lys Phe Ser Ala Glu Ala Leu Arg Cys Arg Leu Arg Asp Arg Val
130 135 140

Asn Val Ser Met Ile Glu Ala Thr Asp Phe Pro Phe Asn Thr Thr Glu
145 150 155 160

Trp Ala Gly Tyr Leu Pro Lys Glu Asn Ile Arg Thr Lys Ala Gly Pro
165 170 175

Trp His Arg Cys Ala Val Val Ser Ser Ala Gly Ser Leu Lys Ser Ser
180 185 190

Gln Leu Gly Arg Glu Ile Asp Asn His Asp Ala Val Leu Arg Phe Asn
195 200 205

Gly Ala Pro Val Ala Asn Phe Gln Gln Asp Val Gly Thr Lys Thr Thr
210 215 220

Ile Arg Leu Met Asn Ser Gln Leu Ile Thr Thr Glu Lys Gln Phe Leu
225 230 235 240

Lys Asp Ser Leu Tyr Ser Glu Gly Ile Leu Ile Val Trp Asp Pro Ser
245 250 255

Leu Tyr His Ala Asp Ile Pro Ser Trp Tyr Gln Lys Pro Asp Tyr Asn
260 265 270

Phe Phe Glu Thr Tyr Lys Ser Tyr Arg Lys Leu Tyr Pro Asp Gln Pro
275 280 285

Phe Tyr Ile Leu Arg Pro Gln Met Pro Trp Glu Leu Trp Asp Ile Ile

```
            290                 295                 300
Gln Glu Ile Ala Pro Asp Arg Ile Gln Pro Asn Pro Ser Ser Gly
305                 310                 315                 320

Met Leu Gly Ile Met Ile Met Thr Leu Cys Asp Gln Val Asp Ile
                325                 330                 335

Tyr Glu Phe Leu Pro Ser Arg Arg Lys Thr Asp Val Cys Tyr His
                340                 345                 350

Gln Lys Phe Phe Asp Ser Ala Cys Thr Met Gly Ala Tyr His Pro Leu
                355                 360                 365

Leu Phe Glu Lys Asn Met Val Lys Gln Leu Asn Glu Gly Thr Asp Glu
                370                 375                 380

Asp Ile Tyr Ile Phe Gly Lys Ala Thr Leu Ser Gly Phe Arg Thr Ile
385                 390                 395                 400

His Cys

<210> SEQ ID NO 22
<211> LENGTH: 523
<212> TYPE: PRT
<213> ORGANISM: Cricetulus griseus
<220> FEATURE:
<221> NAME/KEY: misc_feature
<222> LOCATION: (307)..(307)
<223> OTHER INFORMATION: Xaa can be any naturally occurring amino acid

<400> SEQUENCE: 22

Met Lys Pro His Leu Lys Gln Trp Arg Gln Arg Met Leu Phe Gly Ile
1               5                   10                  15

Phe Val Trp Gly Leu Leu Phe Leu Ala Ile Phe Ile Tyr Phe Thr Asn
                20                  25                  30

Ser Asn Pro Ala Ser Pro Val Pro Ser Ser Phe Ser Phe Val Glu Asn
                35                  40                  45

Arg Gly Leu Leu Pro Val Gln Gly Lys Gln Arg Ala Ile Met Gly Ala
            50                  55                  60

Leu Gln Glu Ser Ser Leu Pro Arg Ser Leu Glu Ala Ser Lys Ala Leu
65              70                  75                  80

Pro Gly Ser His Pro Ala Ser Pro Phe His Gly Gly Pro Gly Asp Pro
                85                  90                  95

Gln Lys Trp Asp Gln Thr Gln Asp Gly Phe Asp Asn Gly Glu Glu Phe
                100                 105                 110

Phe Leu Pro Gln Val Gly Arg Lys Ser Gln Ser Ala Phe Tyr Pro Glu
                115                 120                 125

Glu Asp Ser Tyr Phe Phe Ala Ala Gly Gln Pro Gly Trp His Arg His
                130                 135                 140

Thr Gln Gly Ala Leu Gly Leu Pro Ser Pro Gly Glu Pro Ser Arg Arg
145                 150                 155                 160

Ala Gly Pro Val Gln His Lys Arg Glu Lys Leu His Arg Ala Arg Arg
                165                 170                 175

Ser Arg Val Pro Glu Asp Ala Tyr Asp Gly Asp Met Leu Ser Ala Ser
                180                 185                 190

Met Ser Arg Ala Phe Leu Tyr Arg Leu Trp Lys Gly Thr Val Ser Ser
                195                 200                 205

Lys Met Leu Asn Pro Arg Leu Gln Lys Ala Met Arg Tyr Tyr Met Ser
                210                 215                 220

Phe Asn Lys His Gly Val Arg Phe Arg Gly Arg Arg Glu Val Arg Arg
225                 230                 235                 240
```

```
Thr Gly Pro Glu Leu Leu Cys Glu Leu Arg Arg Val Arg Val Arg
            245                 250                 255

Thr Leu Asp Gly Lys Glu Pro Pro Phe Ser Ala Leu Gly Trp Arg Pro
        260                 265                 270

Leu Val Pro Gly Val Pro Leu Ser Gln Leu His Pro Arg Gly Leu Arg
        275                 280                 285

Thr Cys Ala Val Val Met Ser Ala Gly Ala Ile Leu Asn Ser Ser Leu
        290                 295                 300

Gly Glu Xaa Ile Asp Ser His Asp Ala Val Leu Arg Phe Asn Ser Ala
305                 310                 315                 320

Pro Thr Arg Gly Tyr Glu Lys Asp Val Gly Asn Lys Thr Thr Val Arg
                325                 330                 335

Ile Ile Asn Ser Gln Ile Leu Ala Asn Pro Ser His His Phe Ile Asp
            340                 345                 350

Ser Ser Leu Tyr Lys Asp Val Ile Leu Val Ala Trp Asp Pro Ala Pro
        355                 360                 365

Tyr Ser Ala Asn Leu Asn Leu Trp Tyr Lys Lys Pro Asp Tyr Asn Leu
        370                 375                 380

Phe Thr Pro Tyr Ile Gln His Arg Arg His Pro Thr Gln Pro Phe
385                 390                 395                 400

Tyr Ile Leu His Pro Lys Phe Ile Trp Gln Leu Trp Asp Ile Ile Gln
                405                 410                 415

Glu Asn Thr Arg Glu Lys Ile Gln Pro Asn Pro Pro Ser Ser Gly Phe
            420                 425                 430

Ile Gly Ile Leu Ile Met Lys Ser Met Cys Arg Glu Val His Val Tyr
        435                 440                 445

Glu Tyr Ile Pro Ser Val Arg Gln Thr Glu Leu Cys His Tyr His Glu
        450                 455                 460

Leu Tyr Tyr Asp Ala Ala Cys Thr Leu Gly Ala Tyr His Pro Leu Leu
465                 470                 475                 480

Tyr Glu Lys Leu Leu Val Gln Arg Leu Asn Met Gly Thr Gln Ala Asp
                485                 490                 495

Leu His His Lys Gly Lys Val Val Leu Pro Gly Phe Arg Ala Leu Arg
            500                 505                 510

Cys Pro Val Thr Ser Pro Asn Asn Thr Tyr Ser
        515                 520

<210> SEQ ID NO 23
<211> LENGTH: 350
<212> TYPE: PRT
<213> ORGANISM: Homo sapiens

<400> SEQUENCE: 23

Met Lys Cys Ser Leu Arg Val Trp Phe Leu Ser Val Ala Phe Leu Leu
1               5                   10                  15

Val Phe Ile Met Ser Leu Leu Phe Thr Tyr Ser His His Ser Met Ala
            20                  25                  30

Thr Leu Pro Tyr Leu Asp Ser Gly Ala Leu Asp Gly Thr His Arg Val
        35                  40                  45

Lys Leu Val Pro Gly Tyr Ala Gly Leu Gln Arg Leu Ser Lys Glu Arg
    50                  55                  60

Leu Ser Gly Lys Ser Cys Ala Cys Arg Arg Cys Met Gly Asp Ala Gly
65                  70                  75                  80

Ala Ser Asp Trp Phe Asp Ser His Phe Asp Gly Asn Ile Ser Pro Val
                85                  90                  95
```

```
Trp Thr Arg Glu Asn Met Asp Leu Pro Pro Asp Val Gln Arg Trp Trp
            100                 105                 110

Met Met Leu Gln Pro Gln Phe Lys Ser His Asn Thr Asn Glu Val Leu
            115                 120                 125

Glu Lys Leu Phe Gln Ile Val Pro Gly Glu Asn Pro Tyr Arg Phe Arg
            130                 135                 140

Asp Pro His Gln Cys Arg Arg Cys Ala Val Val Gly Asn Ser Gly Asn
145                 150                 155                 160

Leu Arg Gly Ser Gly Tyr Gly Gln Asp Val Asp Gly His Asn Phe Ile
                165                 170                 175

Met Arg Met Asn Gln Ala Pro Thr Val Gly Phe Glu Gln Asp Val Gly
            180                 185                 190

Ser Arg Thr Thr His His Phe Met Tyr Pro Glu Ser Ala Lys Asn Leu
            195                 200                 205

Pro Ala Asn Val Ser Phe Val Leu Val Pro Phe Lys Val Leu Asp Leu
            210                 215                 220

Leu Trp Ile Ala Ser Ala Leu Ser Thr Gly Gln Ile Arg Phe Thr Tyr
225                 230                 235                 240

Ala Pro Val Lys Ser Phe Leu Arg Val Asp Lys Glu Lys Val Gln Ile
                245                 250                 255

Tyr Asn Pro Ala Phe Phe Lys Tyr Ile His Asp Arg Trp Thr Glu His
            260                 265                 270

His Gly Arg Tyr Pro Ser Thr Gly Met Leu Val Leu Phe Phe Ala Leu
            275                 280                 285

His Val Cys Asp Glu Val Asn Val Tyr Gly Phe Gly Ala Asp Ser Arg
            290                 295                 300

Gly Asn Trp His His Tyr Trp Glu Asn Asn Arg Tyr Ala Gly Glu Phe
305                 310                 315                 320

Arg Lys Thr Gly Val His Asp Ala Asp Phe Glu Ala His Ile Ile Asp
                325                 330                 335

Met Leu Ala Lys Ala Ser Lys Ile Glu Val Tyr Arg Gly Asn
            340                 345                 350

<210> SEQ ID NO 24
<211> LENGTH: 333
<212> TYPE: PRT
<213> ORGANISM: Homo sapiens

<400> SEQUENCE: 24

Met Val Ser Lys Ser Arg Trp Lys Leu Leu Ala Met Leu Ala Leu Val
1               5                   10                  15

Leu Val Val Met Val Trp Tyr Ser Ile Ser Arg Glu Asp Arg Tyr Ile
            20                  25                  30

Glu Leu Phe Tyr Phe Pro Ile Pro Glu Lys Lys Glu Pro Cys Leu Gln
            35                  40                  45

Gly Glu Ala Glu Ser Lys Ala Ser Lys Leu Phe Gly Asn Tyr Ser Arg
        50                  55                  60

Asp Gln Pro Ile Phe Leu Arg Leu Glu Asp Tyr Phe Trp Val Lys Thr
65                  70                  75                  80

Pro Ser Ala Tyr Glu Leu Pro Tyr Gly Thr Lys Gly Ser Glu Asp Leu
                85                  90                  95

Leu Leu Arg Val Leu Ala Ile Thr Ser Ser Ile Pro Lys Asn Ile
            100                 105                 110

Gln Ser Leu Arg Cys Arg Arg Cys Val Val Val Gly Asn Gly His Arg
```

```
                115                 120                 125
Leu Arg Asn Ser Ser Leu Gly Asp Ala Ile Asn Lys Tyr Asp Val Val
    130                 135                 140

Ile Arg Leu Asn Asn Ala Pro Val Ala Gly Tyr Glu Gly Asp Val Gly
145                 150                 155                 160

Ser Lys Thr Thr Met Arg Leu Phe Tyr Pro Glu Ser Ala His Phe Asp
                165                 170                 175

Pro Lys Val Glu Asn Asn Pro Asp Thr Leu Leu Val Leu Val Ala Phe
            180                 185                 190

Lys Ala Met Asp Phe His Trp Ile Glu Thr Ile Leu Ser Asp Lys Lys
        195                 200                 205

Arg Val Arg Lys Gly Phe Trp Lys Gln Pro Pro Leu Ile Trp Asp Val
    210                 215                 220

Asn Pro Lys Gln Ile Arg Ile Leu Asn Pro Phe Phe Met Glu Ile Ala
225                 230                 235                 240

Ala Asp Lys Leu Leu Ser Leu Pro Met Gln Gln Pro Arg Lys Ile Lys
                245                 250                 255

Gln Lys Pro Thr Thr Gly Leu Leu Ala Ile Thr Leu Ala Leu His Leu
            260                 265                 270

Cys Asp Leu Val His Ile Ala Gly Phe Gly Tyr Pro Asp Ala Tyr Asn
        275                 280                 285

Lys Lys Gln Thr Ile His Tyr Tyr Glu Gln Ile Thr Leu Lys Ser Met
    290                 295                 300

Ala Gly Ser Gly His Asn Val Ser Gln Glu Ala Leu Ala Ile Lys Arg
305                 310                 315                 320

Met Leu Glu Met Gly Ala Ile Lys Asn Leu Thr Ser Phe
                325                 330

<210> SEQ ID NO 25
<211> LENGTH: 331
<212> TYPE: PRT
<213> ORGANISM: Homo sapiens

<400> SEQUENCE: 25

Met Arg Gly Tyr Leu Val Ala Ile Phe Leu Ser Ala Val Phe Leu Tyr
1               5                   10                  15

Tyr Val Leu His Cys Ile Leu Trp Gly Thr Asn Val Tyr Trp Val Ala
                20                  25                  30

Pro Val Glu Met Lys Arg Arg Asn Lys Ile Gln Pro Cys Leu Ser Lys
            35                  40                  45

Pro Ala Phe Ala Ser Leu Leu Arg Phe His Gln Phe His Pro Phe Leu
        50                  55                  60

Cys Ala Ala Asp Phe Arg Lys Ile Ala Ser Leu Tyr Gly Ser Asp Lys
65                  70                  75                  80

Phe Asp Leu Pro Tyr Gly Met Arg Thr Ser Ala Glu Tyr Phe Arg Leu
                85                  90                  95

Ala Leu Ser Lys Leu Gln Ser Cys Asp Leu Phe Asp Glu Phe Asp Asn
            100                 105                 110

Ile Pro Cys Lys Lys Cys Val Val Gly Asn Gly Gly Val Leu Lys
        115                 120                 125

Asn Lys Thr Leu Gly Glu Lys Ile Asp Ser Tyr Asp Val Ile Ile Arg
    130                 135                 140

Met Asn Asn Gly Pro Val Leu Gly His Glu Glu Val Gly Arg Arg
145                 150                 155                 160
```

```
Thr Thr Phe Arg Leu Phe Tyr Pro Glu Ser Val Phe Ser Asp Pro Ile
            165                 170                 175

His Asn Asp Pro Asn Thr Thr Val Ile Leu Thr Ala Phe Lys Pro His
            180                 185                 190

Asp Leu Arg Trp Leu Leu Glu Leu Leu Met Gly Asp Lys Ile Asn Thr
            195                 200                 205

Asn Gly Phe Trp Lys Lys Pro Ala Leu Asn Leu Ile Tyr Lys Pro Tyr
    210                 215                 220

Gln Ile Arg Ile Leu Asp Pro Phe Ile Ile Arg Thr Ala Ala Tyr Glu
225                 230                 235                 240

Leu Leu His Phe Pro Lys Val Phe Pro Lys Asn Gln Lys Pro Lys His
            245                 250                 255

Pro Thr Thr Gly Ile Ile Ala Ile Thr Leu Ala Phe Tyr Ile Cys His
            260                 265                 270

Glu Val His Leu Ala Gly Phe Lys Tyr Asn Phe Ser Asp Leu Lys Ser
        275                 280                 285

Pro Leu His Tyr Tyr Gly Asn Ala Thr Met Ser Leu Met Asn Lys Asn
    290                 295                 300

Ala Tyr His Asn Val Thr Ala Glu Gln Leu Phe Leu Lys Asp Ile Ile
305                 310                 315                 320

Glu Lys Asn Leu Val Ile Asn Leu Thr Gln Asp
                325                 330
```

GLYCOPROTEIN

This application is a National Stage Application of PCT/FI2012/051239, filed 13 Dec. 2012, which claims benefit of Ser. No. 20116264, filed 13 Dec. 2011 in Finland, Ser. No. 61/569,900, filed 13 Dec. 2011 in the United States and Ser. No. 61/569,906, filed 13 Dec. 2011 in the United States and which applications are incorporated herein by reference. To the extent appropriate, a claim of priority is made to each of the above disclosed applications.

FIELD OF THE INVENTION

The invention relates to a glycoprotein, a composition, a host cell and a method of producing the glycoprotein or composition.

BACKGROUND OF THE INVENTION

Glycoproteins mediate many essential functions in humans and other mammals, including signalling, cell-to-cell communication and molecular recognition and association. Antibodies or immunoglobulins are glycoproteins that play a central role in the humoral immune response and that are used increasingly as therapeutics. Antigen-specific recognition by antibodies results in the formation of immune complexes that may activate multiple effector mechanisms.

There are five major classes of immunoglobulins (Igs): IgA, IgD, IgE, IgG and IgM. Several of these may further be divided into subclasses (isotypes), e.g. IgG1, IgG2, IgG3 and IgG4. Papain digestion of antibodies produces two identical antigen binding fragments called Fab fragments and a residual Fc fragment. In human IgG molecules, the Fc region is generated by papain cleavage N-terminal to Cys 226. The Fc region is central to the effector function of the antibodies and interaction with various molecules, such as Fcγ receptors (FcγRI, FcγRIIa, FcγRIIb, FcγRIIc, FcγRIIIa and FcγRIIIb), rheumatoid factor (RF), Protein G and A, complement factors (C3b, C1q) and lectin receptors (MBL, MR, DC-SIGN (Dendritic Cell-Specific Intercellular adhesion molecule-3-Grabbing Non-integrin)). The interaction of antibodies and antibody-antigen complexes with cells of the immune system mediates a variety of responses, including antibody-dependent cell-mediated cytotoxicity (ADCC) and complement dependent cytotoxicity (CDC). In order to be useful in therapy, an antibody, or a fragment thereof, should therefore have suitable effector functions.

The Fc domain sequence of IgG comprises a single site for N-linked glycosylation within its $C_H2$ domain at an asparagine residue 297 (Asn297) numbered according to the EU index (Kabat et al., Sequences of proteins of immunological interest, $5^{th}$ ed., US Department of Health and Human Services, NIH Publication No. 91-3242). Typically the oligosaccharide structures attached to the Fc domain comprise biantennary chains with varying galactosylation.

It is known that the oligosaccharide structure attached to the Fc domain influences the binding of IgG to Fc receptors and other molecules that interact with the antibody molecule, such as C1q (Raju 2008, Curr Opin Immunol 20, 471-478). Thus variations in the oligosaccharide structure (i.e. different glycoforms) of the Fc domain influence ADCC and CDC activity. Subsequently, modification of said oligosaccharide structure may affect the therapeutic activity of an antibody or a fragment thereof. The ability to produce glycoproteins and compositions comprising thereof that are enriched for particular oligosaccharide structures is highly desirable.

Purpose of the Invention

The purpose of the present invention is to disclose novel glycoproteins comprising an Fc domain and oligosaccharide structures attached thereto that have increased cytotoxic potential due to increased affinity to Fc receptors. Another purpose of the present invention is to disclose said glycoproteins that have improved potency to activate leukocytes.

SUMMARY

The composition according to the present invention is characterized by what is presented in claim 1.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE INVENTION

Figure 1:
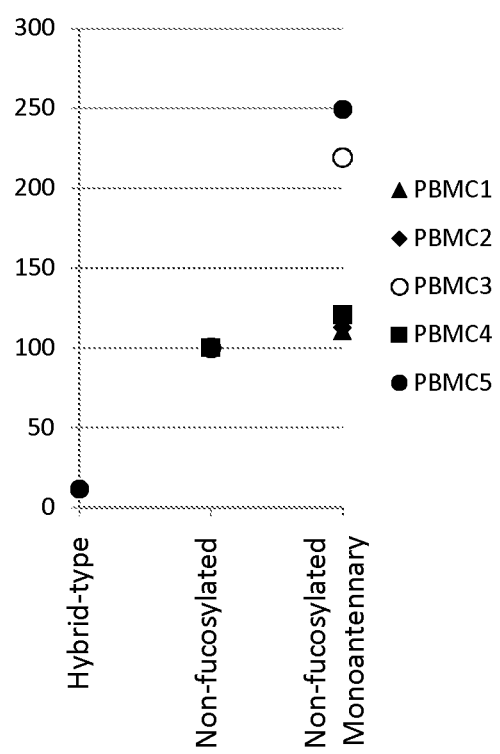
FIG. 1 shows TNF-α production assay with human peripheral blood mononuclear cells (PBMC) from five donors (PBMC1-5) incubated with humanized IgG1 antibody glycoform coated surfaces in 96-well plates; the TNF-α levels have been normalized for each donor relative to the non-fucosylated glycoform: index=100 for the non-fucosylated glycoform.

The present inventors have surprisingly found that a certain subset of oligosaccharide structures present in glycoproteins comprising an Fc domain or a fragment thereof mediate greatly improved cytotoxicity as compared to oligosaccharide structures typically present in said glycoproteins. This effect is due to e.g. improved ADCC and CDC activity and binding to molecules such as FcγRIIIa, FcγRIIa and C1q.

The present invention relates to a glycoprotein comprising the Fc domain of an antibody, or a fragment thereof, comprising an Asn (asparagine) residue and an oligosaccharide structure attached thereto, wherein said oligosaccharide structure has a structure according to formula I:

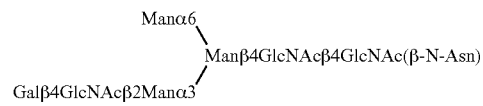

Formula I wherein
(β-N-Asn)=β-N linkage to Asn.

The glycoprotein of the invention comprises the Fc domain of an IgG molecule, or a fragment thereof, which comprises a site for N-linked glycosylation at an Asn residue.

In this context, the term "non-fucosylated monoantennary glycoform" should be understood as meaning a glycoprotein comprising the Fc domain of an antibody, or a fragment thereof, comprising an Asn (asparagine) residue and an oligosaccharide structure attached thereto, wherein said oligosaccharide structure has a structure according to formula I.

In this context, the term "Fc domain" should be understood as meaning a C-terminal region of an antibody or an immunoglobulin heavy chain ("antibody" and "immunoglobulin" are used herein interchangeably). Although the boundaries of the Fc domain of an immunoglobulin heavy chain might vary, the human IgG heavy chain Fc domain is usually defined to stretch from an amino acid residue at position Cys226 to the carboxyl-terminus thereof. The Fc domain generally comprises two constant domains, CH2 and CH3. The "CH2 domain" of a human IgG Fc domain usually extends from about amino acid 231 to about amino acid 340. The "CH3 domain" of a human IgG Fc domain usually extends from about amino acid 341 to about amino acid residue 447 of a human IgG (i.e. comprises the residues C-terminal to a CH2 domain). The term "Fc domain" is also intended to include naturally occurring allelic variants of the "Fc domain" as well as variants having alterations which produce substitutions, additions, or deletions but which do not decrease substantially the ability of the Fc domain to bind effector molecules such as Fc receptors or mediate antibody dependent cellular cytotoxicity. For example, one or more amino acids can be deleted from the N-terminus or C-terminus of the Fc domain of an immunoglobulin without substantial loss of biological function. Such variants, or fragments, of an Fc domain can be selected according to general rules known in the art (See, e.g., Bowie, J. U. et al., Science 247:1306-10 (1990).

In one embodiment of the invention, the Asn residue corresponds to asparagine at position 297 (Asn297) of human IgG wherein the numbering corresponds to the EU index according to Kabat. In this context, the term "according to Kabat" should be understood as meaning the numbering as described in Kabat et al., Sequences of proteins of immunological interest, 5$^{th}$ ed., US Department of Health and Human Services, NIH Publication No. 91-3242. A person skilled in the art can easily identify the amino acid residue corresponding to Asn297 by performing a sequence alignment. The amino acid residue corresponding to Asn297 will align with Asn297. While Asn297 is the N-glycosylation site typically found in murine and human IgG molecules, this site is not the only site that can be envisioned, nor does this site necessarily have to be maintained. Using known methods for mutagenesis, a skilled person can alter a DNA molecule encoding an Fc_domain of the present invention so that the N-glycosylation site at Asn297 is deleted, and can further alter the DNA molecule so that one or more N-glycosylation sites are created at other positions within the Fc_domain. It is preferred that N-glycosylation sites are created within the CH2 region of the antibody molecule.

In one embodiment of the present invention, the Fc domain comprises two heavy chain sequences each comprising at least one Asn residue. In one embodiment of the present invention, one or two of the Fc domain Asn residues are N-glycosylated with oligosaccharide structure according to the invention. In a preferred embodiment of the present invention, two Fc domain Asn residues are N-glycosylated with oligosaccharide structures according to the invention.

In one embodiment of the present invention, the glycoprotein is capable of interacting with at least one molecule selected from the group consisting of FcγRI, FcγRIIa, FcγRIIb, FcγRIIc, FcγRIIIa, FcγRIIIb, rheumatoid factor, Protein G, protein A, C3b, C1q, MBL, MR, and DC-SIGN.

In one embodiment of the present invention, the glycoprotein exhibits increased interaction with at least one molecule selected from the group consisting of FcγRI, FcγRIIa, FcγRIIc, FcγRIIIa, FcγRIIIb, C1q and C3b. In this context, the term "increased interaction" should be understood as meaning increased interaction as compared with a glycoprotein comprising a normal oligosaccharide structure attached thereto. In one embodiment a glycoprotein of the invention exhibits increased interaction with at least one effector molecule, as compared to the glycoprotein comprising normal oligosaccharide structure, where interaction is determined e.g. as disclosed in the Examples herein. In this context, the term "effector molecule" should be understood as meaning a molecule selected from the group consisting of FcγRI, FcγRIIa, FcγRIIc, FcγRIIIa, FcγRIIIb, C1q and C3b, as compared to the glycoprotein comprising normal oligosaccharide structure. In some embodiments, the interaction of the glycoprotein with an effector molecule is increased by about 1.20 fold to about 100 fold, or about 1.5 fold to about 50 fold, or about 2 fold to about 25 fold. In other embodiments, the interaction of the glycoprotein with an effector molecule is increased by at least about 1.10 fold, or at least about 1.20 fold, or at least about 1.30 fold, or at least about 1.4 fold, or at least about 1.5 fold, or at least about 1.6 fold, or at least about 1.70 fold, or at least about 1.8 fold, or at least about 1.9 fold, or at least about 2.0 fold, or at least about 2.5 fold, or at least about 3 fold, or at least about 3.5 fold, or at least about 4.0 fold, or at least about 4.5 fold, or at least about 5.0 fold, or at least about 5.5 fold, or at least about 6 fold, or at least about 7 fold, or at least about 8 fold, or at least about 10 fold, as compared to the glycoprotein comprising normal oligosaccharide structure, where effector molecule interaction is determined as disclosed in the Examples herein. In one embodiment, the effector molecule that the glycoprotein has increased interaction with is FcγRIIIa. In another embodiment, the effector molecule that glycoprotein has increased interaction with is FcγRI (as compared to glycoprotein comprising normal oligosaccharide structure). In still another embodiment, the effector molecule that the glycoprotein has increased interaction with is FcγRIIa. In still another embodiment, the effector molecule that the glycoprotein has increased interaction with is FcγRIIc. In still another embodiment, the effector molecule that the glycoprotein has increased interaction with is FcγRIIIb. In still another embodiment, the effector molecule that the glycoprotein has increased interaction with is C1q. In still another embodiment, the effector molecule that the glycoprotein has increased interaction with is C3b.

In this context, the term "normal oligosaccharide structure" should be understood as meaning an N-glycan structure commonly found attached to an Fc domain comprising the structure shown in the following formula:

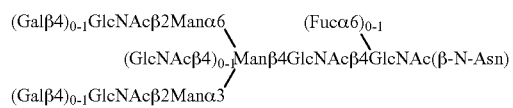

wherein
(β-N-Asn)=β-N linkage to Asn; and the notation 0-1 in e.g. (Galβ4)$_{0-1}$ should be understood as meaning either absent (0) or present (1); in other words, the notation (Galβ4)$_0$ means that the Gal residue is not present, and the notation (Galβ4)$_1$ means that one Gal residue is present. In this context, the term "normal glycoform" should be understood as meaning a glycoprotein comprising a normal oligosaccharide structure. Said normal oligosaccharide structure is present in the majority of antibodies and other glycoproteins comprising an Fc domain produced in mammalian cells.

In this context, the term "hybrid-type oligosaccharide structure" should be understood as meaning an N-glycan structure comprising the structure shown in the formula below:

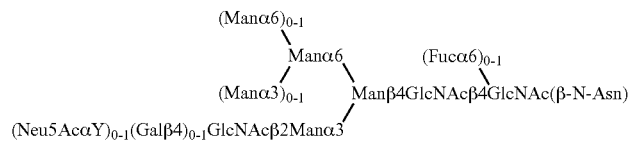

wherein Y=3 or 6; (β-N-Asn)=β-N linkage to Asn; and the notation 0-1 in e.g. (Galβ4)$_{0-1}$ should be understood as meaning either absent or present; when Neu5Ac is present also Gal is present; and at least one of the optional Manα6 and Manα3 groups is present; in other words, the notation (Galβ4)$_0$ means that the Gal residue is not present, and the notation (Galβ4)$_1$ means that one Gal residue is present. In this context, the term "hybrid-type glycoform" should be understood as meaning a glycoprotein comprising a hybrid-type oligosaccharide structure.

In this context, the term "monoantennary oligosaccharide structure" should be understood as meaning an N-glycan structure comprising a structure shown in the formula below:

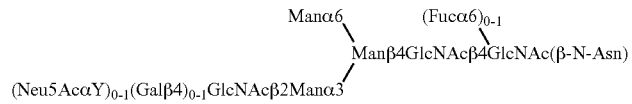

wherein Y=3 or 6; (β-N-Asn)=β-N linkage to Asn; and the notation 0-1 in e.g. (Galβ4)$_{0-1}$ should be understood as meaning either absent or present; when Neu5Ac is present also Gal is present; in other words, the notation (Galβ4)$_0$ means that the Gal residue is not present, and the notation (Galβ4)$_1$ means that one Gal residue is present. In this context, the term "monoantennary glycoform" should be understood as meaning a glycoprotein comprising a monoantennary oligosaccharide structure.

In one embodiment of the present invention, the glycoprotein exhibits improved interaction with C1q. In this context, the term "improved interaction" should be understood as meaning improved interaction as compared with a glycoprotein comprising normal oligosaccharide structure. This embodiment exhibits increased CDC.

In one embodiment of the present invention, the glycoprotein exhibits increased ADCC. In this context, the term "increased ADCC" should be understood as meaning increased ADCC as compared with a glycoprotein comprising normal oligosaccharide structure. This embodiment has increased cytotoxic activity. ADCC may be measured e.g. using the TNF-α production assay described in Example 3 or the ADCC assay described in Example 8. In certain embodiments, a glycoprotein of the invention has increased ADCC or CDC activity, as compared to the glycoprotein comprising normal oligosaccharide structure. In some embodiments, ADCC or CDC activity is increased by about 1.20 fold to about 100 fold, or about 1.5 fold to about 50 fold, or about 2 fold to about 25 fold, as compared to the glycoprotein comprising normal oligosaccharide structure. In other embodiments, the ADCC or CDC activity of a glycoprotein is increased by at least about 1.10 fold, 1.10 fold, or at least about 1.20 fold, or at least about 1.30 fold, or at least about 1.4 fold, or at least about 1.5 fold, or at least about 1.6 fold, or at least about 1.70 fold, or at least about 1.8 fold, or at least about 1.9 fold, or at least about 2.0 fold, or at least about 2.5 fold, or at least about 3 fold, or at least about 3.5 fold, or at least about 4.0 fold, or at least about 4.5 fold, or at least about 5.0 fold, or at least about 5.5 fold, or at least about 6 fold, or at least about 7 fold, or at least about 8 fold, or at least about 10 fold, or at least about 25 fold, as compared to the glycoprotein comprising normal oligosaccharide structure.

In this context, the term "oligosaccharide structure" should be understood as meaning glycan structure or portions thereof, which comprises sugar residues. Such sugar residues may comprise e.g. mannose, N-acetylglucosamine, glucose, galactose, sialic acid or fucose linked to each other through glycosidic bonds in a particular configuration.

In one embodiment of the present invention, the term "oligosaccharide structure" should be understood as meaning an N-glycan.

A person skilled in the art will appreciate that glycoproteins are typically produced in vivo and in vitro as a plurality of variants comprising a mixture of specific oligosaccharide structures attached thereto. In other words, glycoproteins are typically present as different glycoforms.

In this context, the term "glycoform" should be understood as meaning a glycoprotein of the invention comprising specific oligosaccharide structures sharing a common structural feature.

As known in the art (see e.g. "Essentials of Glycobiology", $2^{nd}$ edition, Ed. Varki, Cummings, Esko, Freeze, Stanley, Bertozzi, Hart & Etzler; Cold Spring Harbor Laboratory Press, 2009) and used herein, the term "glycan" should be understood to refer to homo- or heteropolymers of sugar residues, which may be linear or branched. "N-glycan", a term also well known in the art, refers to a glycan conjugated by a β-N-linkage (nitrogen linkage through a β-glycosidic bond) to an asparagine (Asn) residue of a protein. Carbohydrate nomenclature in this context is essentially according to recommendations by the IUPAC-IUB Commission on Biochemical Nomenclature (e.g. Carbohydrate Res. 1998, 312, 167; Carbohydrate Res. 1997, 297, 1; Eur. J. Biochem. 1998, 257, 293).

In this context, the abbreviation "Man" should be understood as meaning D-mannose; "GlcNAc" refers to N-acetyl-D-glucosamine (2-acetamido-2-deoxy-D-glucose); "Fuc" refers to L-fucose; "Gal" refers to D-galactose; terms "Neu5Ac", "NeuNAc" and "sialic acid" refer to N-acetyl-neuraminic acid; all monosaccharide residues are in pyranose form; all monosaccharides are D-sugars except for L-fucose; "Hex" refers to a hexose sugar; "HexNAc" refers to an N-acetylhexosamine sugar; and "dHex" refers to a deoxyhexose sugar. In one embodiment of the present invention, "sialic acid" may also refer to other sialic acids in addition to N-acetylneuraminic acid, such as N-glycolyl-neuraminic acid (Neu5Gc).

The notation of the oligosaccharide structure and the glycosidic bonds between the sugar residues comprised therein follows that commonly used in the art, e.g. "Manα2Man" should be understood as meaning two mannose residues linked by a covalent linkage between the first carbon atom of the first mannose residue to the second carbon atom of the second mannose residue linked by an oxygen atom in the alpha configuration. Furthermore, in this context, the notation of the oligosaccharide structure "Neu5AcαYGalβ" wherein Y=3 or 6 should be understood as meaning a structure comprising a N-acetylneuraminic acid residue linked to a galactose residue by a covalent linkage between the second carbon atom of the N-acetyl-neuraminic acid residue to either the third or the sixth carbon atom of the galactose residue linked by an oxygen atom in the alpha configuration.

In this context, the notation "Galβ4GlcNAcβ2Manα3 (Manα6)Manβ4GlcNAcβ4GlcNAc" should be understood as referring to an oligosaccharide structure according to formula I. In other words, brackets in the context of this type of notation indicate branches in the oligosaccharide structure.

In one embodiment of the present invention, the glycoprotein comprises an Fc domain which is a human Fc domain, or a fragment thereof.

In one embodiment of the present invention, the glycoprotein is a fusion protein comprising an Fc domain, or a fragment thereof. Said fusion protein may, in addition to the Fc domain, or a fragment thereof, comprise e.g. a receptor moiety having a different biological function. Fusion protein should also be understood as meaning antibody like molecules which combine the "binding domain" of a heterologous "adhesin" protein (e.g. a receptor, ligand or enzyme) with an Fc domain. Structurally, these immunoadhesins comprise a fusion of the adhesin amino acid sequence with the desired binding specificity which is other than the antigen recognition and binding site (antigen combining site) of an antibody (i.e. is "heterologous") and an Fc domain sequence. Examples of immunoadhesins include but are not limited to etanercept (available e.g. under the trade mark ENBREL®), which is a soluble TNF receptor 2 protein fused to the Fc region of human IgG1, carcionembryonic antigen-immunoglobulin Fc fusion protein (CEA-Fc) and factor IX-Fc fusion protein.

In one embodiment of the invention, the glycoprotein is a human antibody. In this context, the term "human antibody", as it is commonly used in the art, is to be understood as meaning antibodies having variable regions in which both the framework and complementary determining regions (CDRs) are derived from sequences of human origin.

In one embodiment of the invention, the glycoprotein is a humanized antibody. In this context, the term "humanized antibody", as it is commonly used in the art, is to be understood as meaning antibodies wherein residues from a CDR of an antibody of human origin are replaced by residues from a CDR of a nonhuman species (such as mouse, rat or rabbit) having the desired specificity, affinity and capacity.

In one embodiment of the invention, the glycoprotein is a chimeric antibody comprising a human Fc domain. In this context, the term "chimeric antibody", as it is commonly used in the art, is to be understood as meaning antibodies wherein residues in an antibody of human origin are replaced by residues from an antibody of a nonhuman species (such as mouse, rat or rabbit) having the desired specificity, affinity and capacity.

In this context, the terms "antibody" and "immunoglobulin", as commonly used in the art, should be understood as being used interchangeably.

In one embodiment of the invention, the glycoprotein is an IgG (immunoglobulin G) antibody.

In one embodiment of the invention, the glycoprotein is an IgG1, IgG2, IgG3 or IgG4 antibody.

In one embodiment of the present invention, the glycoprotein is a monoclonal antibody.

In one embodiment of the present invention, the glycoprotein is an antibody directed against human vascular endothelial growth factor (VEGF), epidermal growth factor receptor 1 (EGFR), tumor necrosis factor alpha (TNF-α), CD20, epidermal growth factor receptor 2 (HER2/neu), CD52, CD33, CD11a, glycoprotein IIb/IIIa, CD25, IgE, IL-2 receptor, or respiratory syncytial virus (RSV). However, these antibody targets are provided as examples only, to which the invention is not limited; a skilled person will appreciate that the glycoprotein of the invention is not limited to any particular antibody or form thereof.

In one embodiment of the present invention, the glycoprotein is the antibody bevacizumab (available e.g. under the trademark AVASTIN®), tositumomab (BEXXAR®), etanercept (ENBREL®), trastuzumab (HERCEPTIN®), adalimumab (HUMIRA®), alemtuzumab (CAMPATH®), gemtuzumab ozogamicin (MYLOTARG®), efalizumumab (RAPTIVE®), rituximab (RITUXAN®), infliximab (REMICADE®), abciximab (REOPRO®), baasiliximab (SIMULECT®), palivizumab (SYNAGIS®), omalizumab (XOLAIR®), daclizumab (ZENAPAX®), cetuximab (ERBITUX®), panitumumab (VECTIBIX®) or ibritumomab tiuxetan (ZEVALIN®). However, these antibodies are provided as examples only, to which the invention is not limited; a skilled person will appreciate that the glycoprotein of the invention is not limited to any particular antibody or form thereof.

Monoclonal antibodies to the target of interest may be prepared using any technique which provides for the production of antibody molecules by continuous cell lines in culture. These include, but are not limited to, the hybridoma technique originally described by Kohler and Milstein, 1975, Nature 256:495-497, the human B-cell hybridoma technique (Kosbor et al., 1983, Immunology Today 4:72; Cote et al., 1983, Proc. Natl. Acad. Sci. U.S.A. 80:2026-2030) and the EBV-hybridoma technique (Cole et al., 1985, Monoclonal Antibodies and Cancer Therapy, Alan R. Liss, Inc., pp. 77-96). In addition, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule of appropriate antigen specificity together with genes from a human antibody molecule of appropriate biological activity can be used. Alternatively, techniques described for the production of single chain antibodies (U.S.

Pat. No. 4,946,778) can be adapted to produce single chain antibodies having a desired specificity.

In one embodiment of the present invention, the glycoprotein further comprises a conjugated molecule selected from a group consisting of a detection-enabling molecule and a therapy-enabling molecule. Examples of detection-enabling molecules are molecules conveying affinity such as biotin or a His tag comprising at least five histidine (His) residues; molecules that have enzymatic activity such as horseradish peroxidase (HRP) or alkaline phosphatase (AP); various fluorescent molecules such as FITC, TRITC, and the Alexa and Cy dyes; gold; radioactive atoms or molecules comprising such; chemiluminescent or chromogenic molecules and the like, which molecules provide a signal for visualization or quantitation. A therapy-enabling molecule may be a molecule used for e.g. increasing valence, size, stability and/or prolonged circulation of antibodies and other therapeutic proteins, e.g. a polyethylene glycol (PEG) or poly(vinylpyrrolidone) (PVP) moiety, a radioactive atom or molecule comprising said atom to be used for radiotherapy, or e.g.a toxin or a prodrug activating enzyme.

The present invention also relates to a composition comprising the glycoprotein of the present invention.

In one embodiment of the invention, the composition further comprises a glycoprotein having a different oligosaccharide structure. In other words, the composition further comprises one or more glycoforms.

In one embodiment of the invention, at least 20% of the oligosaccharide structures attached to the glycoprotein in the composition consist of oligosaccharide structures according to formula I.

In one embodiment of the invention, at least 33% of the oligosaccharide structures attached to the glycoprotein in the composition consist of oligosaccharide structures according to formula I.

In one embodiment of the invention, at least 50% of the oligosaccharide structures attached to the glycoprotein in the composition consist of oligosaccharide structures according to formula I.

In one embodiment of the invention, at least 66.7% (⅔) of the oligosaccharide structures attached to the glycoprotein in the composition consist of oligosaccharide structures according to formula I.

In one embodiment of the invention, at least 90% of the oligosaccharide structures attached to the glycoprotein in the composition consist of oligosaccharide structures according to formula I.

In one embodiment of the invention, at least 95% of the oligosaccharide structures attached to the glycoprotein in the composition consist of oligosaccharide structures according to formula I.

In one embodiment of the invention, at least 99% of the oligosaccharide structures attached to the glycoprotein in the composition consist of oligosaccharide structures according to formula I.

In one embodiment of the present invention, the feature "at least 20% of the oligosaccharide structures attached to glycoprotein in the composition consist of oligosaccharide structures according to formula I" or any other feature indicating the percentage or the proportion of specific oligosaccharide structures should be understood as referring to a feature indicating that the indicated proportion, e.g. at least 20%, of all oligosaccharide structures attached to any glycoprotein in the composition, said any glycoprotein comprising a glycoprotein of the invention and optionally one or more other glycoproteins, consist of the specific oligosaccharide structures, e.g. those according to formula I. The percentage or proportion of oligosaccharide structures or portions thereof attached to glycoprotein or glycoproteins in the composition may be measured e.g. by releasing all oligosaccharide structures attached to any glycoprotein in the composition and determining the percentage or proportion of the specific oligosaccharide structures therein, as described e.g. in the Examples.

In one embodiment of the present invention, the feature "at least 20% of the oligosaccharide structures attached to glycoprotein in the composition consist of oligosaccharide structures according to formula I" or any other feature indicating the percentage or the proportion of specific oligosaccharide structures should be understood as referring to a feature indicating that the indicated proportion, e.g. at least 20%, of the Fc domain oligosaccharide structures attached to the Fc domains in the composition, said Fc domains comprised in a glycoprotein of the invention and optionally in one or more other glycoproteins, consist of the specific oligosaccharide structures, e.g. those according to formula I. The percentage or proportion of oligosaccharide structures or portions thereof attached to Fc domain or Fc domains in the composition may be measured e.g. by isolating the Fc domains or antibodies in the composition, releasing all oligosaccharide structures attached to the Fc domains and determining the percentage or proportion of the specific oligosaccharide structures therein, as described e.g. in the Examples.

In one embodiment of the invention, no more than 50% of the oligosaccharide structures attached to glycoprotein in the composition comprise α1,6-linked fucose (Fuc) residue.

Said Fuc residue, as shown in the hybrid-type and monoantennary glycan formulas above, is attached to the GlcNAc residue present in the core Manβ4GlcNAcβ4GlcNAc structure that is linked by a β-N linkage to Asn. In other words, no more than said proportion of the oligosaccharide structures attached to glycoprotein in the composition are core fucosylated.

In this context, the term "core fucosylated" should be understood as meaning an oligosaccharide structure wherein a α1,6-linked fucose (Fuc) residue, as shown in the hybrid-type and monoantennary glycan formulas above, is attached to the core GlcNAc residue present in the core Manβ4GlcNAcβ4GlcNAc structure that is linked by a β-N linkage to Asn.

In one embodiment of the invention, no more than 25% of the oligosaccharide structures attached to glycoprotein in the composition comprise the Fuc residue.

In one embodiment of the invention, no more than 10% of the oligosaccharide structures attached to glycoprotein in the composition comprise the Fuc residue.

In one embodiment of the invention, no more than 5% of the oligosaccharide structures attached to glycoprotein in the composition comprise the Fuc residue.

In one embodiment of the invention, no more than 1% of the oligosaccharide structures attached to glycoprotein in the composition comprise the Fuc residue.

In one embodiment of the invention, about 0% of the oligosaccharide structures attached to glycoprotein in the composition comprise α1,6-linked fucose (Fuc) residue.

In one embodiment of the present invention, the composition is a pharmaceutical composition.

In this context, the term "pharmaceutical composition" should be understood as a composition for administration to a patient, preferably a human patient.

In one embodiment of the present invention, the pharmaceutical composition comprises a composition for e.g. oral, parenteral, transdermal, intraluminal, intraarterial, intrathecal and/or intranasal administration or for direct injection into tissue. Administration of the pharmaceutical composition may be effected in different ways, e.g. by intravenous, intraperitoneal, subcutaneous, intramuscular, topical or intradermal administration. The pharmaceutical composition of the present invention may further comprise a pharmaceutically acceptable carrier. Examples of suitable pharmaceutically acceptable carriers are well known in the art and include e.g. phosphate buffered saline solutions, water, oil/water emulsions, wetting agents, and liposomes. Compositions comprising such carriers may be formulated by methods well known in the art. Dosages and dosage regimens, as known in the art, may vary depending on a number of factors and may be determined depending on e.g. the patient's age, size, the nature of the glycoprotein, and the administration route. The pharmaceutical composition may further comprise other components such as vehicles, additives, preservatives, other pharmaceutical compositions administrated concurrently, and the like.

The present invention further relates to the composition or glycoprotein according to the invention for use in therapy.

In one embodiment of the present invention, the glycoprotein is administered in a therapeutically effective amount to a human or animal.

The present invention further relates to the glycoprotein according to the invention for use in the treatment of cancer, autoimmune disease, inflammatory disorder, infection or any other disease where cytotoxic activity towards cells or tissues is desired.

In one embodiment of the present invention, the term "cytotoxic activity" should be understood as meaning improved ADCC. In this context, the term "improved ADCC" should be understood as meaning improved ADCC as compared with a glycoprotein comprising normal oligosaccharide structure.

In one embodiment of the present invention, the term "cytotoxic activity" should be understood as meaning improved CDC. In this context, the term "improved CDC" should be understood as meaning improved CDC as compared with a glycoprotein comprising normal oligosaccharide structure.

The present invention further relates to a host cell comprising a polynucleotide encoding the protein moiety of a glycoprotein according to the invention, wherein said host cell has reduced activity of mannosidase II and core fucosylation compared to the parent cell.

The present invention further relates to a host cell comprising a polynucleotide encoding the protein moiety of a glycoprotein according to the invention, wherein said host cell has reduced activity of GnTII β1,2-N-acetylglucosaminyltransferase and core fucosylation compared to the parent cell. In this context, the term "host cell" should be understood as meaning any cell suitable for producing the glycoprotein of the invention.

In this context, the term "protein moiety" should be understood as meaning the glycoprotein without the oligosaccharide structure attached.

In one embodiment of the present invention, the host cell produces the glycoprotein of the invention under the culturing conditions.

In one embodiment of the present invention, the host cell is a mammalian cell. Mammalian cells are particularly suitable hosts for production of glycoproteins, due to their capability to glycosylate proteins in the most compatible form for human application (Cumming et al., Glycobiology 1: 115-30 (1991); Jenkins et al., Nature Biotechnol. 14:975-81 (1996)).

In one embodiment of the present invention, the mammalian cell is a CHO cell, cell line CHO-K1 (ATCC CCL-61), cell line DUXB11 (ATCC CRL-9096) and cell line Pro-5 (ATCC CRL-1781) registered at ATCC, commercially available cell line CHO-S (Cat #11619 of Life Technologies)), a BHK cell (including the commercially available cell line ATCC accession no. CCL 10), a NS0 cell, NS0 cell line (RCB 0213) registered at RIKEN Cell Bank, The Institute of Physical and Chemical Research, subcell lines obtained by naturalizing these cell lines to media in which they can grow, and the like), a SP2/0 cell, a SP2/0-Ag14 cell, SP2/0-Ag14 cell (ATCC CRL-1581) registered at ATCC, sub-cell lines obtained by naturalizing these cell lines to media in which they can grow (ATCC CRL-1581.1), and the like), a YB2/0 cell, a PER cell, a PER.C6 cell, sub-cell lines obtained by naturalizing these cell lines to media in which they can grow, and the like, a rat myeloma cell line YB2/3HL.P2.G11.16Ag.20 cell (including cell lines established from Y3/Ag1.2.3 cell (ATCC CRL-1631), YB2/3HL.P2.G11.16Ag.20 cell, YB2/3HL.P2.G11.16Ag.20 cell (ATCC CRL-1662) registered at ATCC, sub-lines obtained by naturalizing these cell lines to media in which they can grow, and the like), a hybridoma cell, a human leukemic Namalwa cell, an embryonic stem cell, or a fertilized egg cell.

In one embodiment of the present invention, the activity of mannosidase II in the host cell is decreased by addition of a mannosidase II inhibitor. Mannosidase II (EC 3.2.1.114) refers to a mannosyl-oligosaccharide 1,3-1,6-alpha-mannosidase enzyme which hydrolyses the terminal (1->3)- and (1->6)-linked alpha-D-mannose residues in the mannosyl-oligosaccharide GlcNAcMan5GlcNAc2. In one embodiment of the invention, the mannosidase II enzyme is a mammalian enzyme. Examples of mannosidase II enzymes include human mannosidase II A1 (MAN2A1; Gene ID: 4124; Accession No. NM_002372, protein: NP_002363.2 (SEQ ID NO: 1)), human mannosidase II A2 (MAN2A2; Gene ID: 4122; Accession No. NM_006122, protein NP_006113 (SEQ ID NO: 2)), mouse MAN2A1 (Accession No. NM_008549, protein NP_032575.2 (SEQ ID NO: 3)), mouse MAN2A2 (Accession No. NM_172903, protein NP_766491.2 (SEQ ID NO: 4)), rat MAN2A1 (Accession No. NM_012979, protein NP_037111.2 (SEQ ID NO: 5)), and rat MAN2A2 (Accession No. NM_001107527, protein NP_001100997.1 (SEQ ID NO: 6)).

In one embodiment of the present invention, the mannosidase II inhibitor is swainsonine.

In one embodiment of the present invention, the activity of mannosidase II, GnTII or core fucosylation in the host cell is decreased by RNA interference (RNAi). RNAi refers to the introduction of homologous double stranded RNA to specifically target the transcription product of a gene, resulting in a null or hypomorphic phenotype. RNA interference requires an initiation step and an effector step. In the first step, input double-stranded (ds) RNA is processed into nucleotide 'guide sequences'. These may be single- or double-stranded. The guide RNAs are incorporated into a nuclease complex, called the RNA-induced silencing complex (RISC), which acts in the second effector step to destroy mRNAs that are recognized by the guide RNAs through base-pairing interactions. RNAI molecules are thus double stranded RNAs (dsRNAs) that are very potent in silencing the expression of the target gene. The invention provides dsRNAs complementary to the mannosidase II gene, GnTII gene and/or genes encoding enzymes involved in core fucosylation.

The ability of dsRNA to suppress the expression of a mannosidase II gene, GnTII gene and/or genes encoding enzymes involved in core fucosylation corresponding to its own sequence is also called post-transcriptional gene silencing or PTGS. The only RNA molecules normally found in the cytoplasm of a cell are molecules of single-stranded mRNA. If the cell finds molecules of double-stranded RNA, dsRNA, it uses an enzyme to cut them into fragments containing in general 21-base pairs (about 2 turns of a double helix). The two strands of each fragment then separate enough to expose the antisense strand so that it can bind to the complementary sense sequence on a molecule of mRNA. This triggers cutting the mRNA in that region thus destroying its ability to be translated into a polypeptide. Introducing dsRNA corresponding to a particular gene will knock out the cell's endogenous expression of that gene. A possible disadvantage of simply introducing dsRNA fragments into a cell is that gene expression is only temporarily reduced. However, a more permanent solution is provided by introducing into the cells a DNA vector that can continuously synthesize a dsRNA corresponding to the gene to be suppressed.

RNAi molecules are prepared by methods well known to the person skilled in the art. In general, an isolated nucleic acid sequence comprising a nucleotide sequence which is substantially homologous to the sequence of at least one of the mannosidase II gene, GnTII gene and/or genes encoding enzymes involved in core fucosylation and which is capable of forming one or more transcripts able to form a partially of fully double stranded (ds) RNA with (part of) the transcription product of said mannosidase II gene, GnTII gene and/or genes encoding enzymes involved in core fucosylation will function as an RNAi molecule. The double stranded region may be in the order of between 10-250, preferably 10-100, more preferably 20-50 nucleotides in length.

RNA interference (RNAi) is a method for regulating gene expression. For example, double-stranded RNA complementary to mannosidase II gene, GnTII gene and/or genes encoding enzymes involved in core fucosylation can decrease the amount of the enzyme expressed in an antibody expressing cell line, resulting in an increased level of glycoprotein of the invention. Unlike in gene knockouts, where the level of expression of the targeted gene is reduced to zero, by using different fragments of the particular gene, the amount of inhibition can vary, and a particular fragment may be employed to produce an optimal amount of the desired glycoprotein or composition thereof. An optimal level can be determined by methods well known in the art, including in vivo and in vitro assays for Fc receptor binding, effector function including ADCC, efficacy, and toxicity. The use of the RNAi knockdown approach, rather than a complete knockout, allows the fine tuning of the amount of glycan structures according to the invention to an optimal level, which may be of great benefit, if the production of glycoproteins bearing less than 100% of oligosaccharides according to Formula I is desirable.

In one embodiment of the present invention, the activity of mannosidase II, GnTII or core fucosylation in the host cell is decreased by gene disruption (knockout). A person skilled in the art can identify all necessary mannosidase II, GnTII and/or fucosylation genes in the host cell based on e.g. sequence similarity to the human genes described in the Examples. For example, all necessary genes encoding mannosidase II isoforms in a human cell are MAN2A1 (mannosidase II) and MAN2A2 (mannosidase IIx).

In one embodiment of the present invention, the host cell has reduced activity of GnTII compared to the parent cell. "Activity of GnTII" should be understood as meaning correlation between a level of GnTII enzyme activity to transfer a GlcNAc residue to the oligosaccharide structure according to Formula I attached to the glycoprotein of the invention and % portion of the GlcNAc's transferred to the oligosaccharide structures according to Formula I attached to glycoproteins in the composition of the invention. A host cell has "reduced or decreased activity of GnTII" when said cell produces lower % portion of the GlcNAc's transferred to the oligosaccharide structures according to Formula I attached to glycoproteins in the composition of the invention compared to parent cell without manipulations to decrease GnTII activity when cultured in similar or identical conditions. "GnTII" refers to mannosyl (alpha-1,6-)-glycoprotein-beta-1,2-N-acetylglucosaminyltransferase. The protein is a Golgi enzyme catalyzing an essential step in the conversion of oligomannose to complex N-glycans. The term preferably refers to the mammalian enzyme. Examples of GnTII enzymes include human GnTII (Gene ID: 4247; Accession Nos. NM_001015883, NM_002408, NP_001015883 and NP_002399 (SEQ ID NO: 7)), rat GnTII (GeneID: 94273 Accession Nos. NM_053604 and NP_446056 (SEQ ID NO: 8)), mouse (Accession No. NM_146035; protein Accession No. NP_666147 (SEQ ID NO: 9)), and Chinese hamster (Accession No. XM_003513994; protein Accession No. XP_003514042 (SEQ ID NO: 10); from CHO-K1 cells). The term "GNTII" refers to a gene or polynucleotide encoding a GnTII enzyme, including the coding region, non-coding region preceding (leader) and following coding regions, introns, and exons of a GNTII sequence. In particular, the GNTII gene includes the promoter.

In one embodiment of the present invention, the host cell has reduced activity of a fucosyltransferase.

In one embodiment of the present invention, the host cell has reduced activity of an enzyme involved in biosynthesis or intracellular transport of GDP-fucose.

In this context, the term "core fucosylation" should be understood as meaning any enzymatic activity capable of biosynthesis of GDP-fucose or of adding a Fuc residue to the core GlcNAc residue present in the core Manβ4GlcNAcβ4GlcNAc N-glycan structure that is linked by a β-N linkage to Asn, or proteins needed for intracellular transport or GDP-fucose.

In this context "reduced activity of core fucosylation" or "the activity of core fucosylation is decreased" means herein any method which results reduction or lack of core fucosylation of glycoproteins of the invention, preferably in a host cell. A host cell has "reduced activity of core fucosylation" or "the activity of core fucosylation is decreased" when said cell produces lower % portion of the fucose residues in the oligosaccharide structures according to Formula I attached to glycoproteins in the composition of the invention compared to parent cell without manipulations to decrease or reduce activity of core fucosylation when cultured in similar or identical conditions. In one embodiment of the present invention, reduction of core fucosylation is achieved by using Lec13 CHO host cell which is a lectin-resistant Chinese Hamster Ovary (CHO) mutant cell line displaying a defective fucose metabolism and therefore has a diminished ability to add fucose to complex carbohydrates. That cell line is described in Ripka and Stanley, Somatic Cell & Molec. Gen. 12(1):51-62 (1986); and Ripka et al. Arch. Biochem. Biophys. 249(2):533-545 (1986) and is available from the Albert Einstein College of Medicine of Yeshiva University, Bronx, N.Y. Lec13 cells are believed to lack the transcript for GDP-D-mannose-4,6-dehydratase, a key enzyme for fucose metabolism. Ohyama et al. J. Biol. Chem. 273(23):14582-14587 (1988). GDP-D-mannose-4,6-dehydratase generates GDP-mannose-4-keto-6-D-deoxymannose from GDP-mannose, which is then converted by the FX protein to GDP-L-fucose. Expression of fucosylated oligosaccharides is dependent on the GDP-L-fucose donor substrates and fucosyltransferase(s). In one embodiment of the present invention, Lec13 cells are manipulated to have reduced activity of GnTII. In one embodiment that can be combined with preceding embodiments Lec13 cells are manipulated to express optimized or increased levels of β4-galactosyltransferase activity, preferably by activating endogenous β4-galactosyltransferase or transfecting, for example, human β4-galactosyltransferase into said Lec13 cells.

Reduced activity of core fucosylation in a host cell is also achieved by reducing the activity of an enzyme relating to the synthesis of an intracellular sugar nucleotide, GDP-fucose. The enzymes include GMD (GDP-mannose 4,6-dehydratase); (b) Fx (GDP-keto-6-deoxymannose 3,5-epimerase, 4-reductase); (c) GFPP (GDP-beta-L-fucose pyrophosphorylase). Reduction of core fucosylation can also be achieved by reducing the activity of α-1,6-fucosyltransferase or FUT8. As the method for obtaining such cells, any technique can be used, so long as it can reduce or delete the activity of core fucosylation. Examples of the technique for reducing or deleting the enzyme activity include, a gene disruption technique targeting a gene encoding the enzyme, a technique for introducing a dominant negative mutant of a gene encoding the enzyme, a technique for introducing mutation into the enzyme, and a technique for inhibiting transcription and/or translation of a gene encoding the enzyme. Methods to reduce activity of core fucosylation in CHO cells are described in, inter alia, US patents U.S. Pat. No. 7,393,683 and U.S. Pat. No. 6,946,292 by Kyowa Hakko Kirin Co. Ltd.

In this context, the term "parent cell" should be understood as meaning a host cell before decreasing or deleting activity of the mannosidase II or GnTII, and core fucosylation in said cell.

The present invention further relates to a method for producing the glycoprotein according to the invention comprising the steps of
a) culturing the host cell comprising a polynucleotide encoding the protein moiety of a glycoprotein according to the invention in the presence of mannosidase II inhibitor and GDP-fucose synthesis inhibitor; and
b) contacting the product of step a) with an α-mannosidase; and, optionally
c) contacting the product of step b) with a sialidase and/or UDP-Gal and a β1,4-galactosyltransferase.

In one embodiment of the present invention, the α-mannosidase is Jack bean α-mannosidase.

In one embodiment of the present invention, the host cell is cultured in the presence of swainsonine in a concentration of at least 60 μM.

In one embodiment of the present invention, the host cell is cultured in the presence of swainsonine in a concentration of at least 100 μM.

In one embodiment of the present invention, the host cell is cultured in the presence of GDP-fucose synthesis inhibitor as described in Example 1.

In one embodiment of the present invention, the host cell has optimized activity of β1,4-galactosyltransferase compared to the parent cell.

In one embodiment of the present invention, the host cell is manipulated to express optimized levels of a β4-galactosyltransferase activity to generate glycoprotein composition of the invention. In one embodiment, the host cell is selected for the optimized level of a β4-galactosyltransferase activity to generate glycoprotein composition of the invention. In one embodiment, the host cell is manipulated to increase the activity of a β4-galactosyltransferase to generate glycoprotein composition of the invention.

Specifically, such host cell may be manipulated to comprise a recombinant nucleic acid molecule encoding a β4-galactosyltransferase activity operatively linked to a constitutive or regulated promoter system. In one embodiment, the host cell is transformed or transfected with a nucleic acid molecule comprising a gene encoding a β4-galactosyltransferase activity. In one embodiment, the host cell is manipulated such that an endogenous β4-galactosyltransferase has been activated by insertion of a regulated promoter element into the host cell chromosome. In one embodiment, the host cell has been manipulated such that an endogenous β4-galactosyltransferase activity has been activated by insertion of a constitutive promoter element, a transposon, or a retroviral element into the host cell chromosome.

Alternatively, a host cell may be employed that naturally produce, are induced to produce, and/or are selected to produce β4-galactosyltransferase, of increased levels of β4-galactosyltransferase activity. In one embodiment, the host cell has been selected in such way that an endogenous β4-galactosyltransferase is activated. For example, the host cell may be selected to carry a mutation triggering expression of an endogenous β4-galactosyltransferase activity.

In one embodiment, the activity of a β4-galactosyltransferase in the host cell is increased compared to the parent cell to generate glycoprotein composition of the invention. In this context, the term "parent cell" should be understood as meaning a host cell before increasing activity of a β4-galactosyltransferase in said cell.

"Activity of β4-galactosyltransferase" or "levels of β4-galactosyltransferase activity" should be understood as meaning correlation between a level of β4-galactosyltransferase enzyme activity to transfer a Gal residue in the oligosaccharide structure according to Formula I attached to the glycoprotein of the invention and % portion of the galactose residues in the oligosaccharide structures according to formula I attached to glycoproteins in the composition of the invention. A host cell has "increased activity of β4-galactosyltransferase" when said cell produces higher % portion of the galactose residues in the oligosaccharide structures according to Formula I attached to glycoproteins in the composition of the invention compared to parent cell without manipulations to increase β4-galactosyltransferase activity when cultured in similar or identical conditions. A host cell has "optimized activity of β4-galactosyltransferase" when said cell produces higher or lower % portion of the galactose residues in the oligosaccharide structures according to Formula I attached to glycoproteins in the composition of the invention compared to parent cell without manipulations to optimize β4-galactosyltransferase activity when cultured in similar or identical conditions. Optimal levels of β4-galactosyltransferase activity in a host cell depend on % portion of the galactose residues in the oligosaccharide structures according to Formula I attached to glycoproteins in the composition of the invention. Typically, host cell is manipulated to have increased levels of β4-galactosyltransferase activity compared to parent cell when cultured in similar or identical conditions.

β4-galactosyltransferase refers to β-1,4-galactosyl transferase I. In one embodiment, β4-galactosyltransferase is a mammalian enzyme. Examples of β4-galactosyltransferase include but are not limited to human β4-galactosyltransferase I (GENBANK (NIH genetic sequence database) Accession No. P15291; SEQ ID NO: 11), rat β4-galactosyltransferase (GENBANK Accession No. NP.sub.445739; SEQ ID NO: 12), mouse β4-galactosyltransferase (GENBANK Accession No. P15535; SEQ ID NO: 13), and Chinese hamster β4-galactosyltransferase I (GENBANK Accession No. NP.sub. 001233620; SEQ ID NO: 14). Other β4-galactosyltransferases include human B4GALT2(GENBANK Accession No. 060909), human B4GALT3 (GENBANK Accession No. 060512), human B4GALT4 GENBANK Accession No. 060513), and human B4GALT5 GENBANK Accession No. 043286) and their homologues in mouse, rat, and Chinese hamster.

The present invention further relates to a host cell comprising a polynucleotide encoding the protein moiety of a glycoprotein according to the invention, wherein said host cell has reduced activity of GnTII, reduced activity of core fucosylation, and optimized, or increased, levels of β4-galactosyltransferase activity compared to the parent cell.

In one embodiment, host cell has reduced activity of GnTII, reduced activity of core fucosylation, and the activity of a β4-galactosyltransferase is optimized or increased.

In one embodiment, the host cell is manipulated to express optimized levels of a β4-galactosyltransferase activity, has reduced activity of GnTII and reduced activity of core fucosylation to generate the glycoprotein composition of the invention. In one embodiment that may be combined with the preceding embodiments the host cell is essentially devoid of the activity of GnTII. In one embodiment that may be combined with the preceding embodiments the host cell lacks core fucosylation.

In one embodiment, heterogeneity of glycoprotein composition of the present invention is decreased by expressing optimized levels of a β4-galactosyltransferase in the host cell. In one embodiment, heterogeneity of glycoprotein composition of the present invention is decreased by decreasing the activity of one or more sialyltransferase in the host cell compared to the parent cell. In one embodiment, a sialyltransferase is an α2,6-sialyltransferase. α2,6-sialyltransferases include but are not limited to α2,6-sialyltransferases (GENBANK accession No. P13721, SEQ ID NO: 15 and GENBANK accession No. Q701R3, SEQ ID NO: 16), human α2,6-sialyltransferase I (GENBANK accession No. P15907; SEQ ID NO: 17) or human α2,6-sialyltransferase II (GENBANK accession No. Q96JF0; SEQ ID NO: 18), mouse α2,6-sialyltransferases (GENBANK accession No. NP.sub.666045; SEQ ID NO: 19 and GENBANK accession No. Q76K27; SEQ ID NO: 20) and Chinese hamster α2,6-sialyltransferases (GENBANK accession No. NP.sub.001233744; SEQ ID NO: 21 and GENBANK accession No. XP.sub.003499570; SEQ ID NO: 22) or their isoforms.

In one embodiment, the α2,3-sialyltransferase is a mammalian enzyme. In one embodiment of the present invention, the a2,3-sialyltransferase is a human ST3GAL2, ST3GAL4 and ST3GAL6 enzyme (GENBANK accession No. Q16842, SEQ ID NO: 23; GENBANK accession No. Q11206, SEQ ID NO: 24; and GENBANK accession No. Q9Y274, SEQ ID NO: 25) or their isoforms. In one embodiment of the present invention, the α2,3-sialyltransferase is a rat α2,3-sialyltransferase (GENBANK accession Nos. Q11205, P61131, and P61943), mouse α2,3-sialyltransferase (GENBANK accession Nos. Q11204, Q91Y74, and Q8VIB3) or Chinese hamster α2,3-sialyltransferase (GENBANK accession Nos. NP.sub.001233628, and XP.sub. 003509939) or their isoforms.

For example, in the case of CHO cells it is known that CHO derived recombinant glycoproteins have exclusively α2,3-linked sialic acids, since the CHO genome does not include a gene which codes for a functional α2,6-sialyltransferase. If a glycoprotein composition of the present invention is desired to be produced in CHO cell, the activity of GnTII is decreased, the activity of core fucosylation is decreased, and the activity of β4-galactosyltransferase is optimized or increased in said CHO cell. In one embodiment, the activity of an α-2,3-sialyltransferase in the CHO cell is decreased. In one embodiment that may be combined with the preceding embodiments the CHO cell is essentially devoid of the activity of a GnTII. In one embodiment that may be combined with the preceding embodiments the CHO cell is essentially devoid of the activity of an α2,3-sialyltransferase. In one embodiment that may be combined with the preceding embodiments the CHO cell lacks core fucosylation. In cells other than CHO cells, activities of α2,3-sialyltransferase and α2,6-sialyltransferase may be decreased. Methods to decrease activity of α2,3-sialyltransferase and α2,6-sialyltransferase include but are not limited to RNAi and knock-out techniques as described for GnTII and core fucosylation above.

"Activity of α2,3/6-sialyltransferase" or "level of α2,3/6-sialyltransferase activity" should be understood as meaning correlation between a level of α2,3/6-sialyltransferase enzyme activity to transfer a Neu5Ac residue in the oligosaccharide structure attached to the glycoprotein of the invention and % portion of the Neu5Ac residues in the oligosaccharide structures attached to glycoproteins in the composition of the invention. A host cell has "reduced or decreased activity of α2,3/6-sialyltransferase" or "decreased or reduced level α2,3/6-sialyltransferase of activity" when said cell produces lower % portion of the Neu5Ac residues in the oligosaccharide structures attached to glycoproteins in the composition of the invention compared to parent cell without manipulations to decreased α2,3/6-sialyltransferase activity when cultured in similar or identical conditions.

In one embodiment of the present invention, the host cell further has increased activity of a sialidase compared to the parent cell.

In one embodiment of the present invention, activity of a sialidase, especially a cytosolic sialidase activity is increased in the host cell compared to the parent cell. In one embodiment of the present invention, a host cell expressing β4-galactosyltransferase is selected so that activity of a sialidase is increased, the activity of a sialidase produced by the host cell being such that sialic acid residues in the carbohydrate side-chains of glycoprotein produced by the host cell are cleaved, or are cleaved to an extent which affects the function of the glycoprotein.

In one embodiment of the present invention, the host cell further has reduced activity of α2,3-sialyltransferase and/or reduced activity of α2,6-sialyltransferase compared to the parent cell.

Methods which are well known to those skilled in the art can be used to construct a polynucleotide encoding the protein moiety of a glycoprotein according to the invention, the coding sequence of a β4-galactosyltransferase, appropriate transcriptional/translational control signals, possible reporter genes as well as GnTII, enzymes involved in core fucosylation and α2,3/6-sialyltransferase knock-out or RNAi constructs. These methods include in vitro recombinant DNA techniques, synthetic techniques and in vivo recombination/genetic recombination.

Methods which are well known to those skilled in the art can be used to express a polynucleotide encoding the protein moiety of a glycoprotein according to the invention, nucleic acids encoding a β4-galactosyltransferase, and above deletion and RNAi constructs in a host cell. Nucleic acids may be expressed under the control constitutive promoters or using regulated expression systems such as a tetracycline-regulated expression system, a lac-switch expression system, and a metallothionein metal-inducible expression system. The optimal expression levels will be different for each protein of interest, and will be determined using routine experimentation. Expression levels are determined by methods generally known in the art, including Western blot analysis using a glycosyl transferase or a glycosyl hydrolase specific antibody, protein tag specific antibodies, Northern blot analysis using a glycosyl transferase or a glycosyl hydrolase specific nucleic acid probe, or measurement of enzymatic activity. Alternatively, a lectin may be employed which binds to glycans that are substrates or products of the glycosyl transferases or glycosyl hydrolases, for example, agglutinins from *Erythrina cristagalli* (ECA) and *Ricinus communis* (RCA) binding to Galβ1-4GlcNAc, *Sambucus nigra* (SNA) binding to α2,6-linked sialic acid, *Maackia amurensis* (MAA) binding to α2,3-linked sialic acid, *Galanthus nivalis* (GNA) and *Hippeastrum hybrid* (HHA) binding to α-mannose, *Lens culinaris* (LCA) binding to N-glycan core α1,6-linked fucose, and the like.

For the methods of this invention, stable expression is generally preferred to transient expression and also is more amenable to large scale production. Rather than using expression vectors which contain viral origins of replication, host cells can be transformed with the respective coding nucleic acids controlled by appropriate expression control elements and a selectable marker. Following the introduction of foreign DNA, a number of selection systems may be used, which are well known to those skilled in the art.

The host cell comprising a polynucleotide encoding the protein moiety of a glycoprotein according to the invention or producing the glycoprotein composition of the present invention may be identified, for example, by detection by immunoassay, by its biological activity, or by mass spectrometric means described below.

The glycoprotein or the glycoprotein composition produced by the host cell of the invention can be assessed immunologically, for example by Western blots, immunoassays such as radioimmuno-precipitation, enzyme-linked immunoassays and the like. In one embodiment, glycoprotein composition is assayed in in vitro or in vivo tests, for example, as described in Examples.

The present invention provides host cells for the producing composition comprising a glycoprotein comprising the Fc domain of an antibody, or a fragment thereof, comprising an Asn residue and an oligosaccharide structure attached thereto, and that the oligosaccharide structure has a structure according to Formula I. Generally, the host cell has been transformed to express nucleic acids encoding the protein moiety of the glycoprotein for which the production of glycoforms according to Formula I are desired, along with at least one nucleic acid encoding a RNAi, knock-out, or any other construct meant for decreasing the activity of mannosidase II, GnTII, core fucosylation, and/or α2,3/6-sialyltransferase, or nucleic acids encoding a β4-galactosyltransferase or sialidase to increase the activity of β4-galactosyltransferase and/or a sialidase. Typically, the transfected cells are selected to identify and isolate clones that express the any of the above nucleic acids as well as nucleic acids encoding the protein moiety of the glycoprotein. Transfected cells may be assayed with methods described above and Examples to identify and select host cells having optimized levels of β4-galactosyltransferase activity as well as decreased activity of mannosidase II, GnTII, α2,3/6-sialyltransferase and/or core fucosylation. Host cells transfected with nucleic acids encoding the protein moiety of the glycoprotein and cultured under conditions suitable for expression of the protein moiety of the glycoprotein may be assayed with methods described above and Examples to identify and select host cells having optimized levels of β4-galactosyltransferase activity and decreased activity of GnTII and core fucosylation. In one embodiment, the host cell has been selected for expression of endogenous β4-galactosyltransferase or non-expression of mannosidase II, GnTII, α2,3/6-sialyltransferase and/or core fucosylation activity.

For example, host cells may be selected carrying mutations which trigger expression of otherwise silent β4-galactosyltransferase activity. For example, host cells may be selected carrying mutations which inactivate expression of otherwise active mannosidase II, GnTII, α2,3/6-sialyltransferase or core fucosylation activity.

In one embodiment of the present invention, a method for the producing composition of the invention comprises the steps of a) transforming a host cell with vectors or constructs comprising nucleic acid molecules encoding a protein moiety of the glycoprotein of the invention, b) transforming the host cell with vectors or constructs comprising nucleic acid molecules reducing the activity of mannosidase II, GnTII, α2,3/6-sialyltransferase and/or core fucosylation, or culturing said cells in the presence of mannosidase II and GDP-fucose synthesis inhibitor, c) transforming the host cell with vectors or constructs comprising nucleic acid molecules encoding optimized levels of β4-galactosyltransferase activity, d) culturing the host cell under conditions that allow synthesis of said protein moiety of the glycoprotein and gene products of steps b) and c); and e) recovering said glycoprotein composition from said culture.

The method according to the invention may further comprise the step of recovering the glycoprotein from cell culture or from a reaction mixture. The glycoprotein composition may be recovered as crude, partially purified or highly purified fractions using any of the well-known techniques for obtaining glycoprotein from cell cultures. This step may be performed by e.g. precipitation, purification by using techniques such as lectin chromatography or contacting the glycoprotein with immobilized Fc receptor, carbohydrate-binding protein or protein G or A, or any other method that produces a preparation suitable for further use.

The methods of producing the glycoprotein according to the invention usually produce a mixture of glycoforms, i.e. a mixture of glycoprotein comprising the oligosaccharide structure according to the invention together with other glycoforms comprising related (sharing a common structural feature) oligosaccharide structures.

Therefore the present invention further relates to a method for producing the composition according to the invention comprising the steps of a) culturing the host cell comprising a polynucleotide encoding the protein moiety of a glycoprotein according to the invention in the presence of mannosidase II inhibitor and GDP-fucose synthesis inhibitor; and b) contacting the product of step a) with an α-mannosidase.

The present invention also relates to a method for producing the glycoprotein according to the invention or the composition according to the invention, comprising the steps of a) culturing a host cell according to the invention; and, optionally b) contacting the product of step a) with an α-mannosidase and/or or a sialidase, and/or with UDP-Gal and a β1,4-galactosyltransferase.

The method according to the invention may further comprise the step of recovering the composition from cell culture or from a reaction mixture. This step may be performed by e.g. precipitation, purification by using techniques such as lectin chromatography or any other method that produces a preparation suitable for further use.

The method according to the invention may further comprise the step of adding a pharmaceutical carrier or any other ingredients suitable for a pharmaceutical composition.

In one embodiment of the present invention, the method for producing the glycoprotein according to the invention or the composition according to the invention comprises the steps of a) culturing a host cell according to the invention; and b) contacting the product of step a) with α-mannosidase.

The glycoprotein or glycoprotein composition of any above step may be contacted in vitro with β4-galactosyltransferase in the presence of UDP-Gal, with a sialidase, and/or with an α-mannosidase.

The present invention further relates to a method of diagnosing or treating cancer, autoimmune disease, inflammatory disorder, infection or any other disease where cytotoxic activity towards cells or tissues is desired, wherein the composition according to the invention or the glycoprotein according to the invention is administered to a human or animal in an effective amount. The effective amount may vary depending on a number of factors and may be determined depending on e.g. the patient's age, size, the nature of the glycoprotein, and the administration route.

In this context, the term "treatment" should be understood as the administration of an effective amount of a therapeutically active compound of the present invention with the purpose of easing, ameliorating, alleviating, inhibiting, slowing down progression, or reduction of disease burden or eradicating (curing) symptoms of the disease or disorder in question. In one embodiment of the present invention, the term "treatment" should also be understood as meaning a prophylactive therapy meaning preventative therapy without meaning an absolute prevention or cure, but reduction of occurrence, or alleviation, inhibition, slowing down progression of the disease, or reduction of disease burden in the future partially in a patient.

The embodiments of the invention described hereinbefore may be used in any combination with each other. Several of the embodiments may be combined together to form a further embodiment of the invention. A product, or a use, or a method to which the invention is related, may comprise at least one of the embodiments of the invention described hereinbefore.

The glycoprotein of the invention has a number of advantages over glycoproteins comprising other oligosaccharide structures typically attached to said glycoproteins, such as normal oligosaccharide structures. The non-fucosylated monoantennary N-glycan structure according to formula I greatly increases the binding of the glycoprotein of the invention to Fcγ receptors, especially FcγRIIIa and FcγRIIa, and subsequently leads to improved ADCC and activation of immune effector cells; it also increases the binding of the glycoprotein of the invention to complement factors, especially C1q, and subsequently leads to improved CDC. Thus the glycoprotein of the invention leads to increased cytotoxic activity. Furthermore, the oligosaccharide structure according to formula I is relatively simple and does not significantly alter the stability of the glycoprotein. The glycoprotein of the invention is also relatively easy to produce in e.g. mammalian cell culture.

EXAMPLES

In the following, the present invention will be described in more detail. Reference will now be made in detail to the embodiments of the present invention, examples of which are illustrated in the accompanying drawings. The description below discloses some embodiments of the invention in such detail that a person skilled in the art is able to utilize the invention based on the disclosure. Not all steps of the embodiments are discussed in detail, as many of the steps will be obvious for the person skilled in the art based on this specification.

Example 1

Production of Humanized IgG1 Antibody Glycoforms in CHO Cells

Humanized anti-IL-8 IgG1 antibody producing cell line DP-12 (ATCC number CRL-12445) was grown in DMEM with 4 mM L-glutamine and adjusted with sodium bicarbonate and 4.5 g/L glucose and 200 nM methotrexate, trace elements A and B from Mediatech, 0.002 mg/ml rhInsulin and 10% fetal bovine serum. For antibody production, cells were grown for 3-4 days and the supernatant collected by centrifugation.

Glycosidase inhibitors were added to the culture medium to produce specific antibody glycoforms: hybrid-type glycoform, 10 µg/ml swainsonine (Cayman Chemical); non-fucosylated glycoform, 7.2 µg/ml AV39 (a GDP-fucose synthesis inhibitor; Glykos Finland Ltd., Helsinki, Finland); and non-fucosylated hybrid-type glycoform, 10 µg/ml swainsonine and 7.2 µg/ml AV39.

Antibody glycoforms were purified from cell culture supernatants by protein G affinity chromatography on a 1-mL HITRAP protein G column (protein G column) (GE Healthcare, Uppsala, Sweden) using single step pH gradient elution from 20 mM sodium phosphate, pH 7.0 to 0.1 M citric acid, pH 2.6. The eluted antibody fractions were neutralized immediately with 1 M Na2HPO4 and concentrated in Millipore AMICON ULTRACEL (cellulose membrane) 30K concentrators. The concentrations of antibody glycoforms were adjusted to 0.5 mgml with phosphate-neutralized 0.1 M citric acid.

Mass Spectrometric Analysis of Antibody Glycoforms

For N-glycan analysis antibody solution containing 10-20 µg antibody was applied to N-glycan release; optionally antibodies were first precipitated with 67% (v/v) ice-cold ethanol and pelleted by centrifugation; cells were collected, washed repeatedly with phosphate buffered saline and pelleted by centrifugation.

N-glycan release, purification for analysis, permethylation and MALDI-TOF mass spectrometric fragmentation analysis were performed essentially as described previously (Satomaa et al., Cancer Research 2009, 69, 5811-5819) with minor modifications. N-linked glycans were detached by enzymatic hydrolysis with N-glycosidase F (Glyko). N-glycans were first purified on HYPERSEP C-18 and then on HYPERSEP HYPERCARB 50 mg 96-well plates (Thermo Scientific). The neutral and acidic N-glycans were eluted together from Hypercarb with 0.05% trifluoroacetic acid in 25% acetonitrile in water. Matrix-assisted laser desorption-ionization time-of-light (MALDI-TOF) mass spectrometry was performed with a Bruker Ultraflex III instrument (Bruker Daltonics, Germany). Neutral and acidic N-glycans were detected in positive ion reflector mode as sodium adduct ions using 2,5-dihydroxybenzoic acid (DHB, Aldrich) as the matrix. Each of the steps in the glycan isolation procedure was validated with standard glycan mixtures and mass spectrometric analysis before and after purification step to ensure uniform glycan purification and quantitative detection of sialic acid residues in the analysis conditions. The method was optimized for glycan analysis in the used mz range. For the quantitative glycan profile analyses, mass spectrometric raw data were cleaned by carefully removing the effect of isotopic pattern overlapping, multiple alkali metal adduct signals, products of elimination of water from the reducing oligosaccharides, and other interfering mass spectrometric signals not arising from the original glycans in the sample. The resulting cleaned profiles were normalized to 100% to allow comparison between samples.

Preparation of Antibody Glycoforms: Normal and Hybrid-Type Glycoforms

CHO cell line DP-12 obtained from ATCC producing humanized IgG1 against IL-8 was cultured in normal conditions and with swainsonine. N-glycans were analyzed by mass spectrometric N-glycan profiling showing that the Fc domain N-glycans of the CHO cell supernatant-derived normal IgG glycoform were biantennary complex-type glycoform N-glycans with the major glycan signals at m/z 1485.6, 1647.6 and 1809.9 corresponding to the [M+Na]+ ions of Hex3HexNAc4dHex1, Hex4HexNAc4dHex1 and Hex5HexNAc4dHex1 oligosaccharides, respectively, while the IgG preparate produced with swainsonine (hybrid-type glycoform) was essentially completely (>99%) of the hybrid-type glycoform with the major (75% of total N-glycan signals) glycan signal at m/z 1768.7 corresponding to the [M+Na]+ ion of Hex6HexNAc3dHex1 oligosaccharide. The structure of the major product was the hybrid-type glycoform N-glycan Galβ4GlcNAcβ2Manα3[Manα3(Manα6)Manα6]Manβ4GlcNAcβ4(Fucα6)GlcNAc based on sensitivity to β1,4-galactosidase (recombinant *S. pneumoniae* galactosidase, Glyko) digestion and known structure of the mannosidase II inhibition product. Other major Fc-domain N-glycan forms were Neu5Acα3Galβ4GlcNAcβ2Manα3[Manα3(Manα6)Manα6]Manβ4GlcNAcβ4(Fucα6)GlcNAc at m/z 2081.7 for the [M-H+2Na]+ ion (19%) according to mass spectrometric analysis and sensitivity to specific α2,3-sialidase (recombinant *S. pneumoniae* sialidase, Calbiochem) and GlcNAcβ2Manα3[Manα3(Manα6)Manα6]Manβ4GlcNAcβ4(Fucα6)GlcNAc at m/z 1606.6 (6%). In the hybrid-type glycoform no non-fucosylated N-glycans were detected.

The non-fucosylated antibody glycoform produced in the presence of AV39 was similarly analyzed and the major N-glycan signals were the [M+Na]+ ions of Hex3HexNAc4, Hex4HexNAc4 and Hex5HexNAc4, while fucosylated N-glycans accounted for 10% of total signal intensity. The non-fucosylated hybrid-type glycoform produced in the presence of AV39 and swainsonine was similarly analyzed and the major N-glycan signal was the [M+Na]+ ion of Hex6HexNAc3 and no fucosylated glycans were detected.

Non-Fucosylated Monoantennary Glycoforms

The non-fucosylated hybrid-type glycoform produced in the presence of AV39 was subjected to Jack bean α-mannosidase (Sigma Aldrich) digestion in conditions similar to 50-65 U/ml enzyme for 2 days in mM sodium acetate buffer pH 5.5 at +37° C. and purified by protein G affinity chromatography to yield non-fucosylated monoantennary glycoform. Mass spectrometric analysis of this preparate showed that the major N-glycan structure was Galβ4GlcNAcβ2Manα3(Manα6)Manβ4GlcNAcβ4GlcNAc (>70% of total N-glycan signals) and further major Fc-domain N-glycan forms were Neu5Acα3Galβ4GlcNAcβ2Manα3(Manα6)Manβ4GlcNAcβ4GlcNAc and GlcNAcβ2Manα3(Manα6)Manβ4GlcNAcβ4GlcNAc.

Galactosylated Glycoforms

For galactosylation, antibodies were buffer-exchanged to 50 mM MOPS, pH 7.2, 20 mM MnCl2, using a NAP-5 (small scale purification, desalting and buffer exchange) column. 0.5mU/µl of Calbiochem bovine milk β1,4-galactosyltransferase and 5 mM UDP-Gal was added to 6.25 mgml of antibody. Reactions were incubated overnight at +37° C. N-glycans were analyzed as described above. In typical reaction N-glycan galactosylation degree was increased to over 90% of N-glycans and in continued reactions N-glycan galactosylation degree was increased over 99% to essentially completely galactosylated forms.

All the different antibody glycoforms were checked for structural integrity by protein G affinity chromatography as described above as well as polyacrylamide gel electrophoresis.

Example 2

Lectin Chromatography for Enrichment of Specific Glycoforms and Modifications Thereof Non-fucosylated glycoforms of anti-HER2 humanozed IgG1 antibody were enriched by lectin affinity chromatography using Lens culinaris agglutinin (LCA, Medicago) essentially as described in Tojo et al. (Bio. Pharm. Bull. 32 (9): 1604-1608, 2009) and Shinkawa et al. (J. Biol. Chem. 278: 3466-3473, 2003). LCA coupled to SEPHAROSE (crosslinked, beaded-form of agarose) (15 ml, 6.6 mg/ml, NHS-activated SEPHAROSE (crosslinked, beaded-form of agarose) 4 Fast Flow, GE Healthcare) was packed in TRICORN 10/200 HPLC column (GE Healthcare) and the column was installed in AKTAPURIFIER (protein purification system) HPLC system (GE Healthcare). 10 mg of antibody in 50 mM Tris-H2SO4, 1 mM MnCl2, 1 mM CaCl2, pH 7.4 (buffer A) was applied to the column equilibrated with buffer A and unbound sample was washed from the column 0.5 ml/min with buffer A. Bound antibody was eluted 1 ml/min with 50 mM Tris-H2SO4, 1 mM MnCl2, 1 mM CaCl2, 0.2 M methyl-alpha-D-mannopyranoside (Sigma) pH 7.4 (buffer B). Eluted peak was pooled and applied again to the column for a second round of chromatography. After two consecutive chromatographic steps the eluted peak (about 100-150 µg) contained less than about 10% fucosylated glycoforms.

Example 3

TNF-α Production Assay

TNF-α production assay was done essentially as described in Roda, J. M. et al. (The Journal of Immunology (2006), 177: 120-129). In short, wells of a 96-well flat-bottom plate were coated with glycoform antibodies 50, 100 or 200 µg/ml in PBS o/n at 4° C. and washed with cold PBS and warm RPMI-1640 medium. Peripheral blood mononuclear cells (PBMC) were isolated from healthy volunteers using VACUTAINER CPT (cell preparation tube) (BD), washed with PBS and RPMI-1640 medium and suspended 106 cells/ml in medium supplemented with 10% fetal calf serum, 100 U/ml penicillin, 100 µg/ml streptomycin and glutamine. PBMC were added to antibody coated wells 2×105 cells/well and the plates were incubated o/n 37° C. in humidified atmosphere and 5% CO2. TNF-α production was analyzed from cell culture supernatants using Human TNF-α Immunoassay kit (R&D Systems).

Results of a typical TNF-α production assay are shown in FIG. 1. The relative potencies of the antibody glycoforms to induce TNF-α production and thus mediate FcγRIIIa-dependent cellular cytotoxicity (Roda et al. 2006) were in the following order: non-fucosylated monoantennary>non-fucosylated>>normal IgG (data not shown)>hybrid-type.

Example 4

Receptor Binding Assays

Printing of arrays. Arrays were printed onto SCHOTT NEXTERION H MPX-16 slides (Schott Technical Glass Solutions GmbH, Jena, Germany). Antibody isoform and control protein samples were diluted to 0.5 mgml with a buffer that had been made by bringing 100 mM sodium citrate buffer pH 2.6 to pH 7 by adding 1 M Na2HPO4. The samples were printed at a volume of about 400 pL per spot using a Scienion SCIFLEXARRAYER S5 non-contact printer (Scienion AG, Berlin, Germany). For each sample concentration, 6 replicates were printed. 6 replicate spots of Cy3-labeled protein served as positive control and 6 replicate spots of printing buffer solution served as negative controls. In the arrays the distance between adjacent spots was approximately 380 µm. Arrays of up to 24 different isoforms and control substances were printed resulting in 144 spotsarray. The printed array slides were incubated in 75% humidity in room temperature overnight, allowed to dry in room temperature and stored until use in −20° C. in a desiccator.

Hybridization with Effector Molecules and Reading of Arrays

Preparation of binding proteins for assays. Recombinant human Fc gamma receptor IIa was from R&D Systems Inc. (USA) and C1q complement was from Quidel (San Diego, Calif., USA). These binding proteins were labeled with NETS-activated Cy3 or Cy5 (GE Healthcare, UK) according to manufacturer's instructions and purified from excess reagent by changing the buffer to phosphate buffered saline (PBS) in NAP-5 (small scale purification, desalting and buffer exchange) columns (GE Healthcare, UK).

Assay Procedure to Evaluate Fc Gamma Receptor IIa and C1q Binding Affinities.

Printed slides were blocked with 25 mM ethanolamine in 100 mM borate buffer, pH 8.5 for at least one hour in room temperature. Slides were rinsed three times with PBS-TWEEN (Polysorbate) (0.05-0.1% TWEEN), once with PBS and once with water. A SCHOTT NEXTERION (Microarray Glass Substrates) MPX superstructure (Schott Technical Glass Solutions GmbH, Jena, Germany) was attached to create wells. Arrays were incubated with various concentrations of labeled binding proteins in 60 µl volume of PBS buffer. Incubations were carried out for 2-2.5 h at room temperature, after which the slides were washed five times in PBS-TWEEN (Polysorbate), once with PBS, rinsed with water and dried using nitrogen gas stream. Arrays were imaged using Tecan's LS Reloaded laser scanner (Tecan Group Ltd., Switzerland) at excitation wavelengths of 532 and 633 nm and detection wavelengths of 575 and 692 nm for Cy3 and Cy5, respectively. The images were quantified using Array Pro software.

Figure 2:
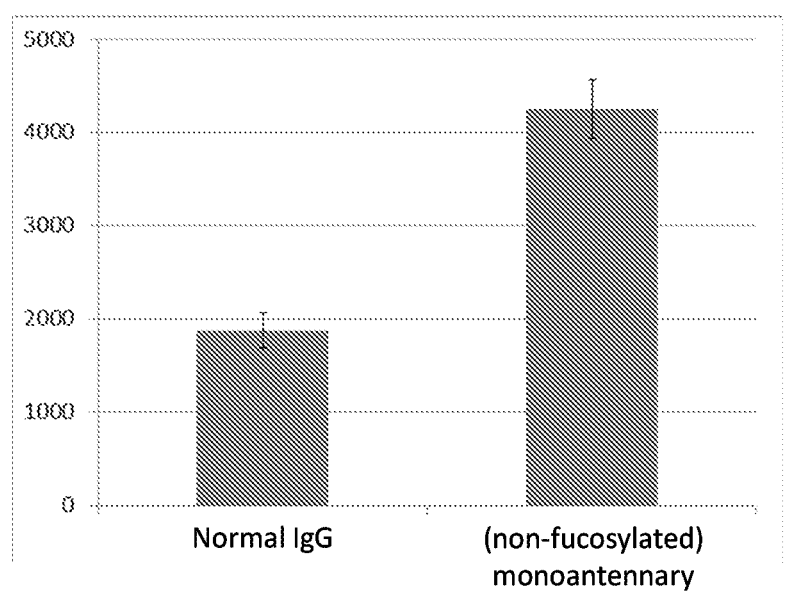
FIG. 2 demonstrates C1q binding results (relative affinity on the y-axis) of humanized IgG1 antibody glycoforms.

Results of a typical C1q-binding assay are shown in FIG. 2. The relative affinities of the antibody glycoforms to C1q were in the following order: monoantennary (comprising mixture of non-fucosylated and core fucosylated N-glycans) >normal IgG.

Figure 3:
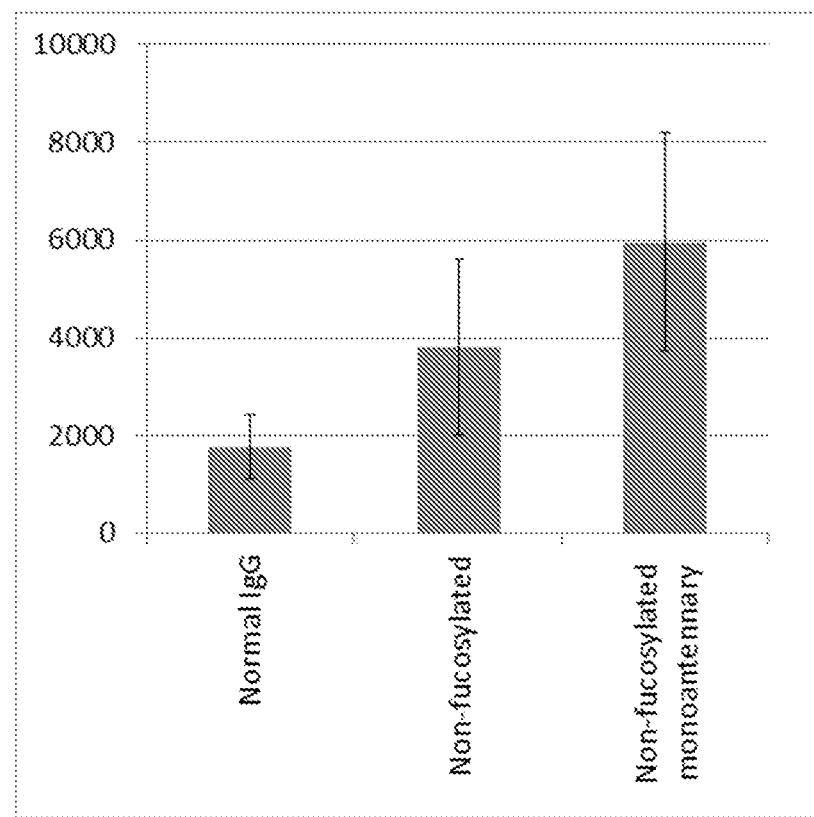
FIG. 3 shows FcγRIIa binding results (relative affinity on the y-axis) of humanized IgG1 antibody glycoforms.

Results of a typical FcγRIIa-binding assay are shown in FIG. 3. The relative affinities of the antibody glycoforms to FcγRIIa were in the following order: non-fucosylated monoantennary>non-fucosylated>normal IgG.

Example 5

Inhibition of Glycosylation Enzymes with Specific siRNAs in HEK-293 Cells

Glycosylation targeted siRNA probes were obtained from Qiagen. Human embryonal kidney HEK-293 cells were cultured in 384-well plates in standard culture conditions and transfected for 48 h with each siRNA in eight replicate experiments. After the transfection, cells were fixed and permeabilized, labelled with lectins PHA-L and AAL (EY Laboratories Inc., USA) labeled with Cy5 as described above and the amount of label was quantitated by image acquisition and analysis with Olympus scanR system. Fold changes were calculated as labeling intensity relative to control cells.

The utilized siRNA probes are identified by Qiagen SI codes as shown in Table 1:

TABLE 1

| Gene | Enzyme | Qiagen SI codes |
| --- | --- | --- |
| MGAT2 | GnTII | SI04248286, SI04308521, SI04314219, SI00630987 |
| MAN2A1 | mannosidase II | SI00036729, SI00036722, SI00036743, SI00036736 |
| MAN2A2 | mannosidase IIx | SI00084672, SI00084679, SI00084658, SI00084665 |
| GMDS | GDP-mannose 4,6-dehydratase (GMD) | SI00428645, SI00428638, SI00428624, SI03106327 |
| TSTA3 | GDP-4-keto-6-deoxy-D-mannose-3,5-epimerase-4-reductase (FX) | SI00050631, SI04437419, SI03026198, SI04437426, SI02665089, SI02665096 |
| FUT8 | N-glycan core α1,6-fucosyltransferase (FucTVIII) | SI03224669, SI03149118 |

One of the anti-MGAT siRNAs, SI04314219, inhibited branched complex-type N-glycan biosynthesis as judged by decreased labeling with PHA-L (labeling intensity fold change −0.66). This indicated that this siRNA had decreased the activity of GnTII in these cells, leading to increased amounts of monoantennary N-glycans.

Three of the anti-MAN2A1 siRNAs, SI00036729, SI00036722 and SI00036743, inhibited branched complex-type N-glycan biosynthesis as judged by decreased labeling with PHA-L (labeling intensity fold changes −0.20, −0.58 and −0.81, respectively). This indicated that these siRNAs had decreased the activity of mannosidase II in these cells, leading to increased amounts of hybrid-type N-glycans.

One of the anti-MAN2A2 siRNAs, SI00084679, inhibited branched complex-type N-glycan biosynthesis as judged by decreased labeling with PHA-L (labeling intensity fold change −0.34) and increased fucosylation as judged by increased labeling with AAL (labeling intensity fold change 0.37). This indicated that these siRNAs had decreased the activity of mannosidase IIx in these cells, leading to increased amounts of core-fucosylated hybrid-type N-glycans.

One of the anti-GMDS siRNAs, SI00428645, three of the anti-TSTA3 siRNAs, SI00050631, SI04437419 and SI03026198, as well as both anti-FUT8 siRNAs inhibited fucosylation as judged by decreased labeling with AAL (labeling intensity fold changes −1.13, −0.67, −0.05, −0.16, −0.52 and −0.19, respectively). This indicated that these siRNAs had decreased fucosylation activity in these cells, leading to decreased amounts of core-fucosylated N-glycans.

Example 6

In Vivo Half-Life of Humanized Antibody Glycoforms

The purpose of the study was to measure in vivo serum half-life of CHO-expressed anti-IL-8 humanized IgG1 antibody glycoforms in healthy mice following a single i.v. administered dose of antibody. N-glycans were isolated from the non-fucosylated monoantennary trastuzumab glycoform and analysed by MALDI-TOF mass spectrometry as described above. The major N-glycan signals were at m/z 1136.4 corresponding to the sodium adduct ion of GlNAcβ2Manα3(Manα6)Manβ4GlcNAcβ4 GlcNAc and at m/z 1298.5 corresponding to the sodium adduct ion of Galβ4GlNAcβ2Manα3(Manα6)Manβ4GlcNAcβ4GlcNAc; the molar ratios of these glycan components were about 40%:60%, respectively. The test animals were female FVB/N mice. Background serum samples (100 µl blood) were taken from all animals three days before the start of the experiment. Serum samples were obtained in serum isolation tubes by centrifuging the blood samples. 50 µg of antibody was injected i.v. via the tail vein in 110 µl phosphate-buffered saline at start of day 1 of the experiment. 100 µl blood samples were taken from all animals 10 min after dosing of test substances and on days 2, 3, 5, 8 and 15. The test substances contained 0.45 g/l anti-IL-8 antibody glycoforms in sterile-filtered phosphate-buffered saline. 100 µl blood samples were collected and serum was isolated. Human IgG concentrations in sera were analysed by anti-human IgG ELISA kit (RD-Biotech, Besancon, France). The rates of elimination from serum of both normal CHO-expressed anti-IL-8 humanized IgG1 antibody and its non-fucosylated monoantennary glycoform were essentially similar in mice: when 50 µg effective dose was administered at day 1, at day 15 the remaining serum concentration of both antibody forms was 2-3 µg/ml.

Example 7

Treatment of Established Ovarian Cancer Xenograft Tumors with Trastuzumab Glycoform Antibodies in Human Leukocyte Grafted Mice The purpose of the study was to test tumor treatment efficacy of trastuzumab glycoforms in comparison to non-treated animals. The study was performed with double xenograft mouse model of HER2 positive cancer. Immunodeficient mice were grafted with both human immune effector cells and tumor forming cancer cells. Tumors were allowed to grow to approximately 5 mm diameter before antibody treatment. Antibody treatment was given weekly i.v. for three weeks and tumor sizes were measured. The experiments were approved by the appropriate ethical committee and the blood donor gave an informed consent.

The test substance was non-fucosylated monoantennary trastuzumab glycoform as described in the preceding examples, produced transiently with FREESTYLE MAX (formulation for the transfection of plasmid DNA into eukarvotic cells) Expression System (Life Technologies) according to manufacturer's instructions. The trastuzumab amino acid sequences were according to the IMGT database (www.imgt.org) for the light chain (7637_L) and heavy chain (7367_H) sequences. Optimized nucleotide sequences encoding the heavy and light chain sequences with functional signal peptide sequences were purchased from GENEART (gene synthesis service) (Life Technologies) and cloned separately into pCEP4 expression vectors (Life Technologies). For antibody expression, the FREESTYLE CHO-S cells were transfected 1:1 with light chain and heavy chain vectors and cultured in the presence of 10 µg/ml swainsonine and 7.2 µg/ml AV39 as described in the preceding examples. The antibodies were then purified with protein G chromatography and treated with α-mannosidase as described above to produce the non-fucosylated monoantennary trastuzumab glycoform for the experiment. N-glycans were isolated and analysed by MALDI-TOF mass spectrometry as described above. In the non-fucosylated monoantennary trastuzumab glycoform, the major N-glycan signals were at mz 1136.4 corresponding to the sodium adduct ion of GlNAcβ2Manα3(Manα6)Manβ4GlcNAcβ4GlcNAc (50% of total glycan signal intensity) and at m/z 1298.5 corresponding to the sodium adduct ion of Galβ4GlNAcβ2Manα3(Manα6)Manβ4GlcNAcβ4GlcN- Ac β3% of total glycan signal intensity).

The test animals were female CIEA NOG mice (Taconic) that lack functional T, B and NK cells and have dysfunctional macrophages and dendritic cells as well as reduced complement activity. The mice were grafted i.v. on day 0 of the experiment with 5×10⁶ peripheral blood mononuclear cells (PBMC), freshly isolated from one human blood donor by gradient centrifugation with VACUTAINER CPT (cell preparation tube)(BD). On day 3 the mice were further grafted s.c. with 5×10⁶ human ovarian cancer SKOV-3i cells originating from ATCC cell line SKOV-3 (HTB-77). The cell line was derived at University of Turku from SKOV-3 xenograft tumors and it was confirmed to express HER2 on the cell surface by flow cytometry, to be susceptible to ADCC by trastuzumab and to form s.c. xenograft tumors to which i.v. administered trastuzumab localizes in vivo.

The first dosing of antibodies was given on day 13 when the tumors had grown to 4-8 mm diameter. The mice with different sized tumors were equally divided into the study groups so that the groups were as similar as possible: eight animals received no treatment and three animals received trastuzumab glycoform treatment. The test substances were prepared 0.5 g/l in sterile-filtered PBS. Antibody treatment was given once weekly for three weeks: i.v. 0.7 mg/kg on days 13, 20 and 27.

Tumor length (L) and width (W) were recorded in mm at various timepoints with ultrasound imaging and at the end of the experiment by direct measurement, and tumor volume (V) in mm³ was calculated according to the formula V=½LW². At the end of the experiment, on day 34, average tumor volumes were 197 mm³ in the treatment group (on average 45% growth in tumor volume between day 13 and day 34) and 232 mm³ in the non-treated group (on average 83% growth in tumor volume between day 13 and day 34), demonstrating that the non-fucosylated monoantennary trastuzumab glycoform was therapeutically effective and inhibited established tumor growth in HER2 positive ovarian cancer xenograft mice.

Example 8

Antibody-Dependent Cellular Cytotoxicity (ADCC) of Trastuzumab Glycoforms

The test substances: normal trastuzumab glycoform, non-fucosylated trastuzumab glycoform and non-fucosylated monoantennary trastuzumab glycoform were produced transiently with FREESTYLE MAX Expression System (Life Technologies) in CHO-S cells as described above. For non-fucosylated trastuzumab glycoform expression, the transfected cells were cultured in the presence of 7.2 µg/ml AV39. For non-fucosylated monoantennary trastuzumab glycoform expression, the transfected cells were cultured in the presence of 10 µg/ml swainsonine and 7.2 µg/ml AV39 and the isolated antibody was further treated with α-mannosidase as described above. The antibodies were purified with protein G chromatography. The humanized IgG1 monoclonal antibody omalizumab (Genentech/Novartis) was used as a negative control. N-glycans were isolated and analysed by MALDI-TOF mass spectrometry as described above. In the non-fucosylated monoantennary trastuzumab glycoform, the major N-glycan signals were at mz 1136.4 corresponding to the sodium adduct ion of GlNAcβ2Manα3(Manα6)Manβ4GlcNAcβ4GlcNAc and at m/z 1298.5 corresponding to the sodium adduct ion of Galβ4GlNAcβ2Manα3(Manα6)Manβ4GlcNAcβ4GlcN-Ac; the molar ratios of these glycan components were 80%:20%, respectively.

HER2 positive SKOV-3 ovarian cancer cells (ATCC) were cultured according to the manufacturer's recommendations and seeded in RPMI medium supplemented with 5% fetal calf serum (medium) into 96-well plates, 10 000 cells/well. Peripheral blood mononuclear cells (PBMCs) were isolated from healthy donor's blood with VACU-TAINER CPT (cell preparation tube) (BD) according to the manufacturer's instructions, washed with phosphate-buffered saline (PBS) and suspended into the medium. Antibodies were diluted into the medium as a 10-fold dilution series to achieve final antibody concentrations from 10 pg/ml to 1 µg/ml; antibodies were incubated in cell incubator at +37 C. for 1 hour before adding PBMCs. PBMCs were added to the 96-well plate 500 000 cells/well to achieve effector:target cell ratio of 50:1. Controls lacking all or some of the target cells, PBMCs or antibody were also prepared and each test was made in triplicate. Final volume in each well was 150 µL. The reactions were incubated for further 4 hours at +37 C.

Cytotoxicity was assayed with lactate dehydrogenase assay kit (Cytotoxicity detection kit plus, Roche) with absorbance determination at 492 nm. Cytotoxicity as ADCC % was calculated according to the formula:

$$ADCC\% = \frac{A492 \text{ nm}(assay) - A492 \text{ nm}(SKOV3) - A492 \text{ nm}(PBMC)}{A492 \text{ nm}(lysed\ cells) - A492 \text{ nm}(SKOV3)} \times 100\%$$

wherein "assay" is well with all SKOV-3 cells, antibody and PBMCs; "SKOV3" is well with only SKOV-3 cells; "PBMC" is well with only PBMCs; and "lysed cells" is well with SKOV-3 cells that have been lysed with lysing solution of the cytotoxicity kit.

The result was that non-fucosylated trastuzumab glycoform and non-fucosylated monoantennary trastuzumab glycoform had similar ADCC % and they both had higher ADCC % than normal trastuzumab glycoform; and over 10-fold smaller antibody concentration of either non-fucosylated trastuzumab glycoform or non-fucosylated monoantennary trastuzumab glycoform was needed to achieve same ADCC % than normal trastuzumab glycoform, indicating over 10-fold higher ADCC potency; while omalizumab had minimal ADCC activity.

As is clear for a person skilled in the art, the invention is not limited to the examples and embodiments described above, but the embodiments can freely vary within the scope of the claims.

The invention claimed is:

1. A pharmaceutical composition comprising a glycoprotein comprising the Fc domain of an antibody, or a fragment thereof, comprising an Asn residue and an oligosaccharide structure attached thereto and a pharmaceutically acceptable carrier, wherein the oligosaccharide structure consists of the structure according to formula I

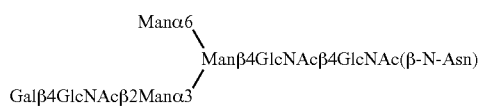

Formula I wherein (β-N-Asn)=β-N linkage to Asn;
wherein at least 50% of the oligosaccharide structures attached to glycoprotein in the composition consist of oligosaccharide structures according to formula I.

2. The pharmaceutical composition according to claim 1, wherein at least 66.7% at least 90%, at least 95%, or at least 99% of the oligosaccharide structures attached to the glycoprotein in the composition consist of oligosaccharide structures according to formula I.

3. The pharmaceutical composition according to claim 1, wherein the Asn residue corresponds to Asn297 of human IgG wherein the numbering corresponds to the EU index as in Kabat.

4. The pharmaceutical composition according to claim 1, wherein the Fc domain is a human Fc domain.

5. The pharmaceutical composition according to claim 1, wherein the glycoprotein is a fusion protein comprising an Fc domain.

6. The pharmaceutical composition according to claim 1, wherein the glycoprotein is a human antibody, a humanized antibody or a chimeric antibody comprising a human Fc domain.

7. The pharmaceutical composition according to claim 1, wherein the glycoprotein is an IgG antibody.

8. The pharmaceutical composition according to claim 1, wherein the glycoprotein is an IgG1 antibody.

9. The pharmaceutical composition according to claim 1, wherein the glycoprotein is an antibody directed against human vascular endothelial growth factor (VEGF), epidermal growth factor receptor 1 (EGFR), tumor necrosis factor alpha (TNF-α), CD20, epidermal growth factor receptor 2 (HER2/neu), CD52, CD33, CD11a, glycoprotein IIb/IIIa, CD25, IgE, interleukin-2 (IL-2) receptor, or respiratory syncytial virus (RSV).

10. The pharmaceutical composition according to claim 1, wherein the glycoprotein is an antibody that is bevacizumab, tositumomab, etanercept, trastuzumab, adalimumab, alemtuzumab, gemtuzumab ozogamicin, efalizumumab, rituximab, infliximab, abciximab, baasiliximab, palivizumab, omalizumab, daclizumab, cetuximab, panitumumab, or ibritumomab tiuxetan.

* * * * *